(12) United States Patent
Davis et al.

(10) Patent No.: US 11,279,751 B2
(45) Date of Patent: Mar. 22, 2022

(54) FIBRONECTIN BINDING DOMAINS WITH REDUCED IMMUNOGENICITY

(71) Applicant: Bristol-Myers Squibb Company, Princeton, NJ (US)

(72) Inventors: Jonathan Davis, Madison, WI (US); Dasa Lipovsek, Pepperell, MA (US); Ray Camphausen, Wayland, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 86 days.

(21) Appl. No.: 16/581,877

(22) Filed: Sep. 25, 2019

(65) Prior Publication Data

US 2020/0123229 A1   Apr. 23, 2020

Related U.S. Application Data

(60) Division of application No. 15/237,484, filed on Aug. 15, 2016, now Pat. No. 10,464,995, which is a
(Continued)

(51) Int. Cl.
*C40B 40/10* (2006.01)
*C07K 14/78* (2006.01)
(Continued)

(52) U.S. Cl.
CPC .............. *C07K 14/78* (2013.01); *C07K 14/47* (2013.01); *C07K 16/241* (2013.01);
(Continued)

(58) Field of Classification Search
None
See application file for complete search history.

(56) References Cited

U.S. PATENT DOCUMENTS

| 5,514,581 A | 5/1996 | Ferrari et al. |
| 5,545,620 A | 8/1996 | Wahl et al. |

(Continued)

FOREIGN PATENT DOCUMENTS

| CN | 1651575 A | 8/2005 |
| EP | 0098431 B1 | 11/1986 |

(Continued)

OTHER PUBLICATIONS

Ackermann, M. et al., "Anti-VEGFR2 and Anti-IGF-1R-adnectins Inhibit Ewing's Sarcoma A673-xenograft Growth and Normalize Tumor Vascular Architecture," Angiogenesis 15:685-695, Springer (Dec. 2012).

(Continued)

*Primary Examiner* — Christian C Boesen
(74) *Attorney, Agent, or Firm* — Sterne, Kessler, Goldstein & Fox P.L.L.C.

(57) ABSTRACT

Fibronectin type III ($^{10}$Fn3) binding domains having novel designs that are associated with reduced immunogenicity are provided. The application describes alternative $^{10}$Fn3 binding domains in which certain immunogenic regions are not modified when producing a binder in order to maintain recognition as a self antigen by the host organism. The application also describes $^{10}$Fn3 binding domains in which HLA anchor regions have been destroyed thereby reducing the immunogenic contribution of the adjoining region. Also provided are $^{10}$Fn3 domains having novel combinations of modified regions that can bind to a desired target with high affinity.

20 Claims, 16 Drawing Sheets

Specification includes a Sequence Listing.

Related U.S. Application Data division of application No. 13/757,664, filed on Feb. 1, 2013, now Pat. No. 9,416,170, and a division of application No. 13/757,668, filed on Feb. 1, 2013, now Pat. No. 9,765,132, said application No. 13/757,664 is a continuation of application No. 13/757,668, filed on Feb. 1, 2013, now Pat. No. 9,765,132, which is a continuation of application No. 13/757,664, filed on Feb. 1, 2013, now Pat. No. 9,416,170, which is a continuation of application No. PCT/US2012/062826, filed on Oct. 31, 2012, said application No. 13/757,668 is a continuation of application No. PCT/US2012/062826, filed on Oct. 31, 2012.

(60) Provisional application No. 61/553,878, filed on Oct. 31, 2011.

(51) Int. Cl.
    | | | |
    |---|---|---|
    | *C07K 16/24* | (2006.01) | |
    | *C07K 16/28* | (2006.01) | |
    | *C07K 14/47* | (2006.01) | |
    | *G01N 33/68* | (2006.01) | |
    | *C12N 15/10* | (2006.01) | |
    | *A61K 38/00* | (2006.01) | |

(52) U.S. Cl.
    CPC ............ *C07K 16/244* (2013.01); *C07K 16/28* (2013.01); *C07K 16/2833* (2013.01); *C07K 16/2857* (2013.01); *C12N 15/1062* (2013.01); *G01N 33/68* (2013.01); *G01N 33/6887* (2013.01); *A61K 38/00* (2013.01); *C07K 2317/92* (2013.01); *C07K 2318/20* (2013.01); *C40B 40/10* (2013.01)

(56) References Cited

U.S. PATENT DOCUMENTS

| | | |
|---|---|---|
| 5,641,648 A | 6/1997 | Ferrari et al. |
| 5,770,697 A | 6/1998 | Ferrari et al. |
| 5,792,742 A | 8/1998 | Gold et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,462,189 B1 | 10/2002 | Koide |
| 6,518,018 B1 | 2/2003 | Szostak et al. |
| 6,818,418 B1 | 11/2004 | Lipovsek et al. |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 9,416,170 B2 | 8/2016 | Davis et al. |
| 9,522,951 B2 | 12/2016 | Davis et al. |
| 9,765,132 B2 | 9/2017 | Davis et al. |
| 10,464,995 B2 | 11/2019 | Davis et al. |
| 10,604,556 B2 | 3/2020 | Davis et al. |
| 2002/0019517 A1 | 2/2002 | Koide |
| 2003/0170753 A1 | 9/2003 | Koide |
| 2003/0186385 A1 | 10/2003 | Koide |
| 2005/0038229 A1 | 2/2005 | Lipovsek et al. |
| 2005/0255548 A1 | 11/2005 | Lipovsek et al. |
| 2006/0210604 A1 | 9/2006 | Dadey et al. |
| 2006/0246059 A1 | 11/2006 | Lipovsek et al. |
| 2006/0270604 A1 | 11/2006 | Lipovsek et al. |
| 2007/0082365 A1 | 4/2007 | Lipovsek et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0220049 A1 | 9/2008 | Chen et al. |
| 2009/0176654 A1 | 7/2009 | Cappuccilli et al. |
| 2010/0081792 A1 | 4/2010 | Grant et al. |
| 2010/0144601 A1 | 6/2010 | Jacobs et al. |
| 2010/0152063 A1 | 6/2010 | Cappuccilli et al. |
| 2010/0273216 A1 | 10/2010 | Morin et al. |
| 2010/0278801 A1 | 11/2010 | Shepard et al. |
| 2010/0298541 A1 | 11/2010 | Wu et al. |
| 2010/0322930 A1 | 12/2010 | Kolbinger et al. |
| 2011/0021746 A1 | 1/2011 | Cappuccilli et al. |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0229406 A1 | 9/2011 | Hettmann et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0237684 A1 | 9/2013 | Koide |
| 2013/0245238 A1 | 9/2013 | Davis et al. |
| 2013/0267676 A1 | 10/2013 | Koide |
| 2014/0057807 A1 | 2/2014 | Loew et al. |
| 2015/0051149 A1 | 2/2015 | Davis et al. |
| 2017/0137494 A1 | 5/2017 | Davis et al. |
| 2020/0339662 A1 | 10/2020 | Davis et al. |

FOREIGN PATENT DOCUMENTS

| | | |
|---|---|---|
| EP | 1266025 B1 | 11/2006 |
| EP | 1137941 B1 | 8/2009 |
| EP | 2141243 A2 | 1/2010 |
| EP | 2154535 A1 | 2/2010 |
| EP | 2385067 A1 | 11/2011 |
| EP | 2439212 A1 | 4/2012 |
| EP | 2379718 B1 | 3/2013 |
| WO | WO-9831700 A1 | 7/1998 |
| WO | WO-9856915 A2 | 12/1998 |
| WO | WO-9951773 A1 | 10/1999 |
| WO | WO-0034784 A1 | 6/2000 |
| WO | WO-0164942 A1 | 9/2001 |
| WO | WO-0204523 A2 | 1/2002 |
| WO | WO-0232925 A2 | 4/2002 |
| WO | WO-02081497 A2 | 10/2002 |
| WO | WO-03104418 A2 | 12/2003 |
| WO | WO-2005056764 A2 | 6/2005 |
| WO | WO-2007077028 A2 | 7/2007 |
| WO | WO-2007146959 A2 | 12/2007 |
| WO | WO-2008031098 A1 | 3/2008 |
| WO | WO-2008066752 A2 | 6/2008 |
| WO | WO-2008097497 A2 | 8/2008 |
| WO | WO-2009023184 A2 | 2/2009 |
| WO | WO-2009023266 A1 | 2/2009 |
| WO | WO-2009025806 A2 | 2/2009 |
| WO | WO-2009058379 A2 | 5/2009 |
| WO | WO-2009073115 A1 | 6/2009 |
| WO | WO-2009083804 A2 | 7/2009 |
| WO | WO-2009086116 A2 | 7/2009 |
| WO | WO-2009102421 A2 | 8/2009 |
| WO | WO-2009133208 A1 | 11/2009 |
| WO | WO-2009142773 A2 | 11/2009 |
| WO | WO-2010051274 A2 | 5/2010 |
| WO | WO-2010051310 A2 | 5/2010 |
| WO | WO-2010060095 A1 | 5/2010 |
| WO | WO-2010069913 A1 | 6/2010 |
| WO | WO-2010093627 A2 | 8/2010 |
| WO | WO-2010093771 A1 | 8/2010 |
| WO | WO-2011020033 A2 | 2/2011 |
| WO | WO-2011035202 A2 | 3/2011 |

(56) References Cited

FOREIGN PATENT DOCUMENTS

| WO | WO-2011051333 A1 | 5/2011 |
|---|---|---|
| WO | WO-2011051466 A1 | 5/2011 |
| WO | WO-2011092233 A1 | 8/2011 |
| WO | WO-2011100700 A2 | 8/2011 |
| WO | WO-2011103105 A1 | 8/2011 |
| WO | WO-2011130324 A1 | 10/2011 |
| WO | WO-2011130328 A1 | 10/2011 |
| WO | WO-2011130354 A1 | 10/2011 |
| WO | WO-2011137319 A2 | 11/2011 |
| WO | WO-2011140086 A2 | 11/2011 |
| WO | WO-2011140086 A9 | 12/2011 |
| WO | WO-2011150133 A2 | 12/2011 |
| WO | WO-2012016245 A2 | 2/2012 |
| WO | WO-2012088006 A1 | 6/2012 |
| WO | WO-2012094653 A2 | 7/2012 |
| WO | WO-2012142515 A2 | 10/2012 |
| WO | WO-2012158678 A1 | 11/2012 |
| WO | WO-2012158739 A1 | 11/2012 |
| WO | WO-2012158818 A2 | 11/2012 |
| WO | WO-2012162418 A1 | 11/2012 |
| WO | WO-2012162426 A1 | 11/2012 |
| WO | WO-2013049275 A1 | 4/2013 |
| WO | WO-2013067029 A2 | 5/2013 |

OTHER PUBLICATIONS

Amodeo, P., et al., "Modularity and Homology: Modeling of the Titin Type I Modules and their Interfaces," Journal of Molecular Biology 311:283-296, Academic Press Ltd. (Aug. 2001).
Annex to communication pursuant to Rule 115(1) EPC, mailed Sep. 15, 2015, Summons to Attend Oral Proceedings for European Patent No. EP 2274331, European Patent Office, Germany, 8 pages.
Baron, M., et al., "HNMR Assignment and Secondary Structure of the Cell Adhesion Type III Module of Fibronectin," Biochemistry 31:2068-2073, American Chemical Society, United States (Feb. 1992).
Batori, V., et al., "Exploring the Potential of the Monobody Scaffold: Effects of Loop Elongation on the Stability of a Fibronectin Type III Domain," Protein Engineering 15:1015-1020, Oxford University Press (Dec. 2002).
Bazan, J.F., "Structural Design and Molecular Evolution of a Cytokine Receptor Superfamily," Proceedings of the National Academy of Sciences USA 87:6934-6938 (Sep. 1990).
Campbell, I. D. and Spitzfaden, C., "Building Proteins with Fibronectin Type III Modules, Fibronectin Type III Modules are Versatile Components of Many Proteins. Recent Structures of Module Pairs Show how these Modules are Joined Together," Structure 2:333-337, Current Biology Ltd. (May 1994).
Chen, C.H., et al., "Inhibition of Heregulin Signaling by an Aptamer that Preferentially Binds to the Oligomeric Form of Human Epidermal Growth Factor Receptor-3," Proceedings of the National Academy of Sciences USA 100(16):9226-9231, National Academy of Sciences, United States (Aug. 2003).
Cho, H.S. and Leahy, D.J., "Structure of the Extracellular Region of HER3 Reveals an Interdomain Tether," Science 297(5585):1330-1333, American Association for the Advancement of Science, United States (Aug. 2002).
Clarke, J., et al., "Folding and Stability of a Fibronectin Type III Domain of Human Tenascin," Journal of Molecular Biology 270:771-778, Academic Press Limited (Aug. 1997).
Connelly, R.J., et al., "Mitogenic Properties of a Bispecific Single-chain Fv-Ig Fusion Generated from CD2-specific mAb to Distinct Epitopes," International Immunology 10:1863-1872, Japanese Society for Immunology (Dec. 1998).
Copie, V., et al., "Solution Structure and Dynamics of Linked Cell Attachment Modules of Mouse Fibronectin Containing the RGD and Synergy Regions: Comparison with the Human Fibronectin Crystal Structure," Journal of Molecular Biology 277:663-682, Academic Press Ltd (Apr. 1998).

Cota, E., et al., "Folding of beta-sandwich Proteins: Three-state Transition of a Fibronectin Type III Module," Protein Science 9:112-120, Cambridge University Press (Jan. 2000).
Cota, E., et al., "Two Proteins with the Same Structure Respond Very Differently to Mutation: The Role of Plasticity in Protein Stability," Journal of Molecular Biology 302:713-725, Academic Press (Sep. 2000).
Dickinson, C. D., et al., "Crystal Structure of the Tenth Type III Cell Adheesion Module of Human Fibronectin," Journal of Molecular Biology 236: 1079-1092, Academic Press (Mar. 1994).
Dickinson, C. D., et al., "Crystals of the Cell-binding Module Module of Fibronectin Obtained from a Series of Recombinant Fragments Differing in Length," Journal of Molecular Biology 238:123-127, Academic Press (Apr. 1994).
Dutta, S., et al., "High Affinity Fragment Complementation of a Fibronectin Type III Domain and its Application to Stability Enhancement," Protein Science 14:2838-2848, Cold Spring Harbor Laboratory Press (Nov. 2005).
Dutta, S., et al., "High-throughput Analysis of the Protein Sequence-stability Landscape Using a Quantitative 'Yeast Surface Two-hybrid System' and Fragment Reconstitution," Journal of Molecular Biology 382:721 -733, Academic Press (Oct. 2008).
Ely, K.R., et al., "Common Molecular Scaffold for Two Unrelated RGD Molecules," Protein Engineering 8:823-827, Oxford University Press (Aug. 1995).
Emanuel. S.L., et al. ."Functional activity of a bispecific Adnectin inhibitor to EGFR and IGFR," Abstract No. 2813, IGF-IR and PI3K Pathways, 2009 AACR Annual Meeting, Denver, Colorado, Apr. 18-22, 2 pages (2009).
Fiedler M. and Skerra, A., "Non-Antibody Scaffolds," in Handbook of Therapeutic Antibodies, vol. 2, Dubel, S., ed., pp. 467-499, Wiley-VCH Verlag GmbH & KGaA, Weinheim, Germany (2007).
Garrett, T.P., et al.,"Crystal Structure of a Truncated Epidermal Growth Factor Receptor Extracellular Domain Bound to Transforming Growth Factor alpha," Cell 110(6):763-773, Cell Press, United States (Sep. 2002).
Getmanova, E., et al., "Antagonists to Human and Mouse Vascular Endothelial Growth Factor Receptor 2 Generated by Directed Protein Evolution in Vitro," Chemistry & Biology 13:549-556, Elsevier Ltd, The Netherlands (May 2006).
Gilbreth, R.N., et al., "A Dominant Conformational Role for Amino Acid Diversity in Minimalist Protein-protein Interfaces," Journal of Molecular Biology 381:407-418, Academic Press (Aug. 2008).
Gilbreth, R.N., et al., "Isoform-specific Monobody Inhibitors of Small Ubiquitin-related Modifiers Engineered Using Structure-guided Library Design," Proceedings of the National Academy of Sciences USA 108:7751-7756 (May 10, 2011).
Grebien, F., et al., "Targeting the SH2-Kinase Interface in Bcr-Abl Inhibits Leukemogenesis," Cell 147: 306-319, Elsevier Inc., The Netherlands (Oct. 14, 2011).
Hackel, B.J., et al., "Picomolar Affinity Fibronectin Domains Engineered Utilizing Loop Length Diversity, Recursive Mutagenesis, and Loop Shuffling," Journal of Molecular Biology 381:1238-1252, Academic Press (Sep. 2008).
Hackel, B.J., et al., "The Full Amino Acid Repertoire is Superior to Serine/tyrosine for Selection of High Affinity Immunoglobulin G Binders from the Fibronectin Scaffold," Protein Engineering, Design & Selection 23:211-219, Oxford University Press (Published online Jan. 12, 2010).
Hansen, C.K., "Fibronectin Type III-like Sequences and a New Domain Type in Prokaryotic Depolymerases with Insoluble Substrates," FEBS 305:91-96, Elsevier Science Publishers B.V. (Jun. 1992).
Huang, J., et al., "Conformation-specific Affinity Purification of Proteins using Engineered Binding Proteins: Application to the Estrogen Receptor," Protein Expression and Purification 47:348-354, Elsevier, The Netherlands (Jun. 2006).
International Preliminary Report on Patentability for International Application No. PCT/US2012/062826, International Bureau of WIPO, Switzerland, dated May 6, 2014, 21 pages.
International Search Report for International Application No. PCT/US2012/062826, European Patent Office, The Netherlands, dated Jul. 2, 2013, 11 pages.

(56) References Cited

OTHER PUBLICATIONS

Jacobs, S.A., et al., "Design of Novel FN3 Domains with High Stability by a Consensus Sequence Approach," Protein Engineering, Design & Selection 25:107-117, Oxford University Press (Jan. 12, 2012).
Jacobs, S.A., et al., "FN3 Domain Engineering," in Protein Engineering Prof. Pravin Kaumaya (Ed.), ISBN: 978-953-51-0037-9, InTech, Available from http://www.intechoopen.com/books/;protein-engineering/fn3-domain engineering (Feb. 2012).
Johansson, S., et al., "Fibronectin-integrin Interactions," Frontiers in Bioscience 2:d126-146, Frontiers in Bioscience Publications, United States (Mar. 1997).
Kani, K., et al., "Oligomers of ERBB3 have Two Distinct Interfaces that Differ in their Sensitivity to Disruption by Heregulin," The Journal of Biological Chemistry 280(9):8238-8247, American Society for Bioehemistry and Molecular Biology, United States (Mar. 2005).
Karatan, E., et al., "Molecular Recognition Properties of FN3 Monobodies that Bind the Src SH3 Domain," Chemistry & Biology 11:835-844, Elsevier Ltd., The Netherlands (Jun. 2004).
King, C.A., et al., "DNA Vaccines with Single-chain Fv Fused to Fragment C of Tetanus Toxin Induce Protective Immunity against Lymphoma and Myeloma," Nature Medicine 4:1281-1286, Nature America, Inc., United States (Nov. 1998).
Koide, A., et al., "Accelerating Phage-display Library Selection by Reversible and Site-specific Biotinylation," Protein Engineering Design & Selection 22:685-690, Oxford University Press (Nov. 2009).
Koide, A., et al., "High-affinity Single-domain Binding Proteins with a Binary-code Interface," Proceedings of the National Academy of Sciences 104:6632-6637 (Apr. 2007).
Koide, A., et al., "Probing Protein Conformational Changes in Living Cells by using Designer Binding Proteins: Application to the Estrogen Receptor," Proceedings of the National Academy of Sciences USA 99:1253-1258 (Feb. 2002).
Koide, A., et al., "Stabilization of a Fibronectin Type III Domain by the Removal of Unfavorable Electrostatic Interactions on the Protein Surface," Biochemistry 40:10326-10333, American Chemical Society, United States (Aug. 2001).
Koide, A., et al., "Teaching an Old Scaffold New Tricks: Monobodies Constructed using Alternative Surfaces of the FN3 Scaffold," Journal of Molecular Biology 415:393-405, Elsevier, The Netherlands (Published online Dec. 16, 2012).
Koide, S., "Engineering of Recombinant Crystallization Chaperones," Current Opinion in Structural Biology 19: 449-457, Elsevier, The Netherlands (Aug. May 2009).
Koide, S., et al., "Directed Evolution of Fibronectin Type III Domain to Novel Ligand Binding Proteins," FASEB J. 11:A 1155, Abstract No. 1739, Federation for American Societies for Experimental Biology, United States (1997).
Koide, S., et al., "Directed Evolution of Fibronectin Type III Domain to Novel Ligand Binding Proteins," FASEB J. 11:A837, Abstract No. M40, Federation for American Societies for Experimental Biology, United States (1997).
Koide, S., et al., "Target-Binding Proteins Based on the 10th Human Fibronectin Type III Domain (10Fn3)," in Methods in Enzymol. 503: 135-156, Elsevier Inc., The Netherlands (Jan. 2012).
Kornblihtt, A.R., et al., "Isolation and Characterizations of cDNA Clones for Human and Bovine Fibronectins," Proceedings of the National Academy of Sciences USA 80:3218-3222 (Jun. 1983).
Leahy, D.J., et al., "2.0 a Crystal Structure of a Four-domain Segment of Human Fibronectin Encompassing the RGD Loop and Synergy Region," Cell 84:155-164, Cell Press USA, United States (Jan. 1996).
Leahy, D.J., et al., "Structure of a Fibronectin Type III Domain from Tenascin Phased by MAD Analysis of the Selenomethionyl Protein," Science 258:987-991, American Association for the Advancement of Science, United States (Nov. 1992).

Li, L., et al., "Mechanical Unfolding Intermediates Observed by Single-molecule Force Spectroscopy in a Fibronectin Type III Module," Journal of Molecular Biology 345:817-826, Elsevier, The Netherlands (Jan. 2005).
Liao, H., et al., "mRNA Display Design of Fibronectin-based Intrabodies that Detect and Inhibit Severe Acute Respiratory Syndrome Coronavirus Nucleocapsid Protein," Journal of Molecular Biology 284:17512-17520, Elsevier, The Netherlands (Jun. 26, 2009).
Lipovsek, Dasa et al., "Evolution of an Interloop Disulfide Bond in High-affinity Antibody Mimics Based on Fibronectin Type III Domain and Selected by Yeast Surface Display: Molecular Convergence with Single-Domain Camelid and Shark Antibodies," Journal of Molecular Biology 368:1024-1041 (May 2007).
Lipovsek, D., "Adnectins: Engineered Target-Binding Protein Therapeutics" Protein Engineering, Design & Selection 24: 3-9, Oxford University Press, (Nov. 10, 2009).
Lipovsek, D., et al., "In-vitro Protein Evolution by Ribosome Display and mRNA Display," Journal of Immunological Methods 290:51-67, Elsevier, The Netherlands (Jul. 2004).
Litvinovich, S.V., and Ingham, K.C., "Interactions Between Type III Domains in the 110 kDa Cell-binding Fragment of Fibronectin," Journal of Molecular Biology 248:611-626, Academic Press Ltd (May 1995).
Lombardo, A., et al., "Conformational Flexibility and Crystallization of Tandemly Linked Type III Modules of Human Fibronectin," Protein Science 5:1934-1938, Cambridge University Press (Sep. 1996).
Main, A. L., et al., "The Three-Dimensional Structure of the Tenth Type III Module of Fibronectin: An Insight into RGD-mediated Interactions," Cell 71:671-678, Cell Press USA, United States (Nov. 1992).
Mamluk, R., et al., "Anti-tumor Effect of CT-322 as an Adnectin Inhibitor of Vascular Endothelial Growth Factor Receptor-2," mAbs 2:199-208, Landes Biosceince (Mar./Apr. 2010).
Mao, Y., et al., "Fibronectin Fibrillogenesis, a Cell-mediated Matrix Assembly Process," Matrix Biology 24:389-399, Elsevier B.V., The Netherlands (Sep. 2005).
NCBI Entrez, GenBank Accession No. CAA26536, Kornblihtt, A.R., Apr. 21, 1993.
NCBI Entrez, GenBank Accession No. X02761, Kornblihtt, A.R., Apr. 21, 1993.
NCBI Entrez, GenBank Report, Accession No. AAC48614.1, MacLeod, J.N., Apr. 18, 1996.
NCBI Entrez, GenBank Report, Accession No. P07589, Elsik, C.G., Dec. 19, 2008.
Notice of Opposition mailed Aug. 6, 2014, in EP Patent No. EP 2274331, Bristol Myers Squibb Company, filed May 4, 2009, 29 pages.
Office Action dated Oct. 20, 2015 in U.S. Appl. No. 13/757,664, Davis, et al., filed Feb. 1, 2013.
Office Action dated Sep. 2, 2016 in U.S. Appl. No. 13/757,668, Davis, et al., filed Feb. 1, 2013.
Office Action dated Mar. 24, 2016 in U.S. Appl. No. 13/757,668, Davis, et al., filed Feb. 1, 2013.
Office Action dated Oct. 20, 2015 in U.S. Appl. No. 13/757,668, Davis, et al., filed Feb. 1, 2013.
Office Action dated Mar. 29, 2016 in U.S. Appl. No. 14/355,155, Davis, et al., filed Apr. 29, 2014.
Office Action dated Oct. 26, 2015 in U.S. Appl. No. 14/355,155, Davis, et al. filed Apr. 29, 2014.
Ogiso, H., et al., "Crystal Structure of the Complex of Human Epidermal Growth Factor and Receptor Extracellular Domains," Cell 110(6):775-787, Cell Press, United States (Sep. 2002).
Olson, C., et al., "Design, Expression and Stability of a Diverse Protein Library Based on the Human Fibronectin Type III Domain," Protein Science 16:476-484, Cold Spring Harbor Laboratory Press (Mar. 2007).
Parker, M.H., et al. "Antibody Mimics Based on Human Fibronectin Type Three Domain Engineered for Thermostability and High-Affinity Binding to Vascular Endothelial Growth Factor Receptor Two," Protein Engineering, Design & Selection 18: 435-444, Oxford University Press (Sep. 2005).

(56) References Cited

OTHER PUBLICATIONS

Plaxco, K.W., et al., "A Comparison of the Folding Kinetics and Thermodynamics of Two Homologous Fibronectin Type III Modules," Journal of Molecular Biology 270:763-770, Academic Press Ltd (Aug. 1997).
Plaxco, K.W., et al., "Rapid Refolding of a Proline-rich All-beta-sheet Fibronectin Type III Module," Proceedings of the National Academy of Sciences USA 93:10703-10706 (Oct. 1996).
Potts, J.R. and Campbell, I.D., "Fibronectin Structure and Assembly," Current Opinion in Cell Biology 6:648-655, Current Biology Ltd. (Oct. 1994).
Potts, J.R., et al., "Structure and Function of Fibronectin Modules," Matrix Biology 15:313-320, Gustav Fischer Verlag, Germany (Nov. 1996).
Proprietor's Submission and Amended Claims mailed Mar. 11, 2015, in EP Patent No. EP2274331, Novartis AG, filed May 4, 2009, 40 pages.
Ramamurthy, V., et al., "Structures of Adnectin/Protein Complexes Reveal an Expanded Binding Footprint," Structure 20:259-269, Elsevier Science Ltd., The Netherlands (Feb. 8, 2012).
Response to Proprietor's Submission mailed Jul. 10, 2015, in European Patent No. EP 2274331, Bristol-Myers Squibb Company, filed May 4, 2009, 6 pages.
Richards, J., et al., "Engineered Fibronectin Type III Domain with a RGDWXE Sequence Binds with Enhanced Affinity and Specificity to Human alphavbeta3 Integrin," Journal of Molecular Biology 326:1475-1488, Elsevier Science Ltd (Mar. 2003).
Sequence alignment comparing fibronectins from different species, 10 pages, submitted with Opposition to European Patent No. EP 2274331 on Aug. 6, 2014.
Sequence alignment comparing the human 9th and 10th Fn3 domains with the coresponding domains in fibronectins from other species, 2 pages, submitted with opposition to European Patent No. EP 2274331 on Aug. 6, 2014.
Skerra, A., "Alternative Non-antibody Scaffolds for Molecular Recognition," Current Opinion in Biotechnology 18(4):295-304, Elsevier, England (Aug. 2007).
Tolcher, A.W., et al., "Phase I and Pharmacokinetic Study of CT-322 (BMS-844203), a Targeted Adnectin Inhibitor of VEGFR-2 Based on a Domain of Human Fibronectin," Clinical Cancer Research 17:363-371, American Association for the Advancement of Science, United States (Jan. 11, 2011).
UniProtKB/Swiss-Prot. entry for bovine fibronectin. published Apr. 8, 2008, 4 pages, submitted with Opposition to European Patent No. EP 2274331 on Aug. 6, 2014.
UniProtKB/Swiss-Prot. entry for chicken fibronectin. published Apr. 8, 2008, 3 pages, submitted with Opposition to European Patent No. EP 2274331 on Aug. 6, 2014.
UniProtKB/Swiss-Prot. entry for human fibronectin. published Apr. 29, 2008, 16 pages, submitted with Opposition to European Patent No. EP 2274331 on Aug. 6, 2014.
UniProtKB/Swiss-Prot. entry for mouse fibronectin. published Apr. 8, 2008, 6 pages, submitted with Opposition to European Patent No. EP 2274331 on Aug. 6, 2014.
UniProtKB/Swiss-Prot. entry for rat fibronectin. published Apr. 8, 2008, 5 pages, submitted with Opposition to European Patent No. EP 2274331 on Aug. 6, 2014.
UniProtKB/Swiss-Prot. entry for Xenopus fibronectin. published Apr. 8, 2008, 3 pages, submitted with Opposition to European Patent No. EP 2274331 on Aug. 6, 2014.
Vuento, M. and Vaheri, A., "Purification of Fibronectin from Human Plasma by Affinity Chromatography Under Non-denaturing Conditions," Biochemical Journal 183:331-337 (Nov. 1979).
Wright, C.F., et al., "The Importance of Sequence Diversity in the Aggregation and Evolution of Proteins," (including Supplementary Data) Nature 438(7069):878-881, Nature Publishing Group, England (Dec. 2005).
Xu, L., et al., "Directed Evolution of High-affinity Antibody Mimics Using mRNA Display," Chemistry & Biology 9: 933-942, Elsevier Science Ltd., The Netherlands (Aug. 2002).
Office Action dated Feb. 28, 2019 in U.S. Appl. No. 15/237,484, Davis, et al., filed Aug. 15, 2016, 11 pages.
Office Action dated Oct. 19, 2018 in U.S. Appl. No. 15/237,484, Davis, et al., filed Aug. 15, 2016, 10 pages.
Office Action dated Aug. 7, 2019, 2019 in U.S. Appl. No. 15/341,623, Davis, et al., filed Nov. 2, 2016, 7 pages.
Office Action dated Feb. 26, 2019, 2019 in U.S. Appl. No. 15/341,623, Davis, et al., filed Nov. 2, 2016, 9 pages.
Koide, A et al., "The Fibronectin Type III domain as a Scaffold for Novel Binding Proteins," 284:1141-1151, Academic Press, United States (1998).

```
         0         1         2         3         4         5         6         7         8         9        10
         0....:....1....:....2....:....3....:....4....:....5....:....6....:....7....:....8....:....9....:....0....:....1
         ........:....:....:....:....:....:....:....:....:....:....:....:....:....:....:....:....:....:....:....:....:
VSDVPRD.LEVVAA.TPTS.LLISW.DAPAVTVRY.YRITY.GETGGNSPVQE.FTV.PGSKST.ATISGL.KPGVD.YTITVYA.VTGRGDSPASSKP.ISINY.RTEIDKPSQ
         ---A---  ---B---       ---C---              ---D--      ---E---       ---F----              ---G---
           AB       BC            CD                   DE           EF            FG
```

Fig. 1

A: NorthWest Binder

```
         0    1    2          3     3          4   5      5      6     6     7            8    9    10
         0    1    4    2     3     3          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

B: NorthEast Binder

```
         0    1    2          3     3          4   5      5      6     6     7            8    9    10
         1    8    4    2     3     2          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

C: West Side Binder

```
         0    1    2          3     3          4   5      5      6     6     7            8    9    10
         1    8    4    2     3     2          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

D: South-Front Binder

```
         0    1    2          3     3          4   5      5      6     6     7            8    9    10
         1    8    4    2     3     7          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

E: AG Strand Binder

```
         0    1    2          3     3          4   5      5      6     6     7            8    9    10
         1    8    4    2     3     7          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

F: SouthWest Binder

```
         0    1    2          3     3          4   5      5      6     6     7            8    9    10
         1    8    4    2     3     7          8   1      7      3     8     5     8      8    3    1
VSDVERD LFVVAA TPTS LLISW DAPAVTVRY YRITY GETGGNSPVQE FTV PGSKST ATISGL KPGVD YTITVYA VTGRGDSPASSKP ISINY RTELDKPSQ
         --A--      --B--             --C--         -D-         --E--         --F--              --G--
```

Fig. 2

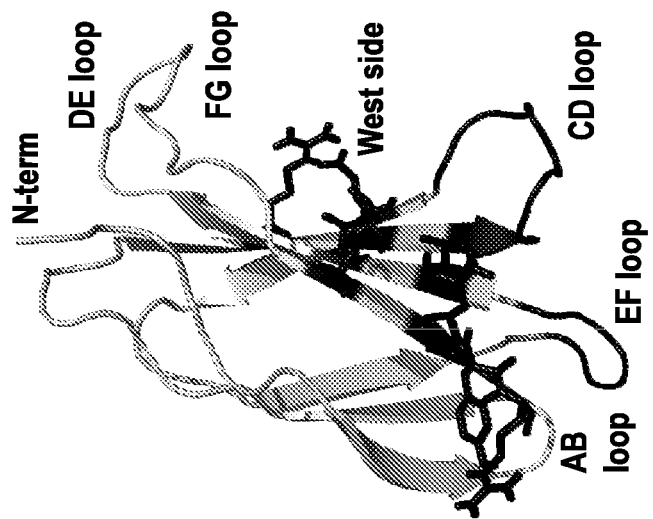
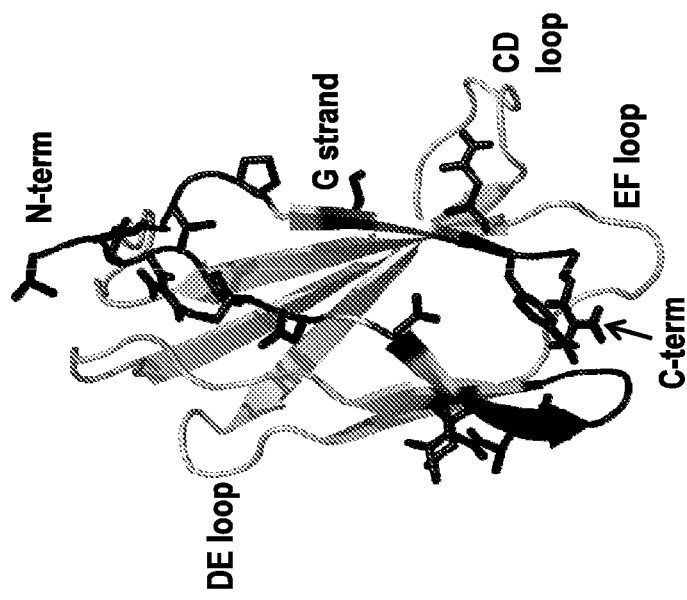
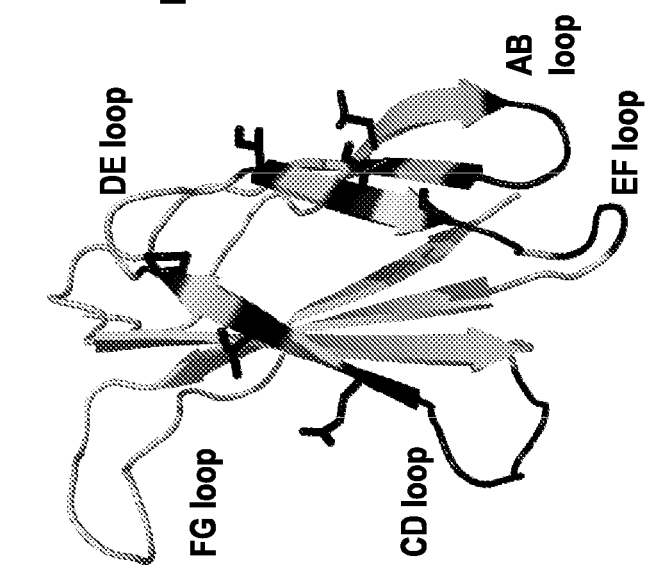
Fig. 3F
Fig. 3E
Fig. 3D

| Region | SEQ ID NO | Sequence | Allele | | | | |
|---|---|---|---|---|---|---|---|
| | | | DRB*0101 | DRB*0301 | DRB*0401 | DRB*0701 | DRB*1501 |
| BC Loop | 58 | PTSLLISWDAPAVTVRYYRITYG | Non-binder | 25.0 | 19.3 | 1.0 | <1 |
| DE Loop | 51 | PVQEFTVPGSKSTATISGLK | Non-binder | Non-binder | 63.7 | >200 | 65.7 |
| FG Loop | 52 | TITVYAVTGRGDSPASSKPISINYRT | Non-binder | Non-binder | Non-binder | 115.5 | 8.8 |
| N-terminal to BC Loop | 53 | MGEVVAATPTSLLIS | 6.0 | 1.0 | 41.5 | 0.5 | <0.1 |
| C-terminal to BC Loop | 54 | PHFPTRYYRITYGETGGNS | 16.1 | Non-binder | 16.7 | 4.4 | 50.0 |

Strong Binders (IC50 value of ≤25 μM)
Moderate Binders (IC50 values between 25 and 100 μM)
Weak Binders (IC50 values >100 μM)
Non-Binder (no concentration-dependent inhibition)

*Fig. 4*

|  | 0 0 1 1 2 2 3 3 3 4 4 5 5 5 6 6 6 7 7 8 8 9 10 |
|---|---|
|  | 1 8 4 AB 8 3 BC 2 7 CD 8 1 DE 7 3 EF 9 5 FG 8 3 1 |
| WT 10Fn3 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
|  | --A-- --B-- --C-- --D-- --E-- --F-- --G-- |
| Classic NP | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| WS1 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| WS2 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| WS3 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| Front1 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| Front2 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| Back1 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| Back2 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| SP1 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| SP2 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| SP3 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| LI-3 (a) | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |
| WS-LI1 | VSDVPRD LEVVAA TPTS LLISW DAPAVTVRY YRITY GETGGNSPVQE FTV PGSKST ATISGL KPGVD YTITVYA VTGRDSPASSKP ISINY RTEIDKPSQ |

Fig. 9A

|  | 0 | 0 | 1 | 1 | 2 | 3 | 3 | 4 | 5 | 5 | 6 | 6 | 7 | 7 | 8 | 9 | 10 |
|---|---|---|---|---|---|---|---|---|---|---|---|---|---|---|---|---|---|
|  | 1 | 8 | 4 AB 8 | 1 | 3 BC | 2 | 7 CD | 8 1 DE | 5 | 7 | 3 EF 8 | 6 | 5 FG | 5 | 8 | 3 | 1 |
| WT 10Fn3 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
|  |  | —A— |  | —B— |  | —C— |  | —D— |  | —E— |  | —F— |  | —G— |  |
| Classic NP | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| LI-S9 | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| SouthFront | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| AG Strand | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| SouthWest | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| WS2' | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| WS2' -CD | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| Front3 | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| Back3 | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| LI-S8 | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |
| CD1-loop | VSDVPRD | LEVVAA | TPTS | LLISW | DAPAVTVRY | YRITY | GETGGNSPVQE | FTV | PGSKST | ATISGL | KPGVD | YTITVYA | VTGRGESPASSKP | ISINY | RTEIDKPSQ |

WT10Fn3         VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
                        —A—         —B—          —C—              —D—     —E—          —F—                        —G—

Classic NP      VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-3 (b)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-1 (a)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-1 (b)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-1 (c)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-2 (a)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
LI-2 (b)        VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
NW3             VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
NP6-2           VSDVPRD LEVVAA TPTS LLISW DAPAVTVRY YRITY GETGGNSPVQE FTV PGSKST ATISGL KPGVD YTITVYA VTGRGDSPASSKP ISINY RTEIDKPSQ
```

*Fig. 9B*

|  | 0 1 | 0 8 | 1 4 AB | 1 8 | 2 3 | 2 8 BC | 3 2 | 3 7 CD | 4 8 | 5 1 DE | 5 7 | 6 3 EF | 6 8 | 7 5 | 7 FG | 8 8 | 8 9 | 10 1 |
|---|---|---|---|---|---|---|---|---|---|---|---|---|---|---|---|---|---|---|
| WT 10Fn3 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
|  | —A— | | —B— | | | —C— | | —D— | | —E— | | —F— | | | —G— | | |
| Classic NP | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP1 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NE1 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP4-5 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP6-1 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NW2 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP1' | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NE1' | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP4 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP4-FG | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP5 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |
| NP6-3 | VSDVPRD | LEVVAA | TPTS | LLISW | DAPAVTVRY | YRITY | GETGGNSPVQE | FTV | PGSKST | ATISGL | KPGVD | YTITVYA | VTGRGDSPASSKP | ISINY | RTEIDKPSQ |

Fig. 9C

FIBRONECTIN BINDING DOMAINS WITH REDUCED IMMUNOGENICITY

CROSS-REFERENCE TO RELATED APPLICATIONS

This application is a divisional application of U.S. application Ser. No. 15/237,484, filed Aug. 15, 2016 (now issued as U.S. Pat. No. 10,464,995), which is a divisional application of both U.S. application Ser. No. 13/757,664, filed Feb. 1, 2013 (now issued as U.S. Pat. No. 9,416,170), and U.S. application Ser. No. 13/757,668, filed Feb. 1, 2013 (now issued as U.S. Pat. No. 9,765,132). U.S. application Ser. No. 13/757,664 is a continuation of U.S. application Ser. No. 13/757,668. U.S. application Ser. No. 13/757,668 is a continuation of U.S. application Ser. No. 13/757,664. Both U.S. application Ser. No. 13/757,664 and U.S. application Ser. No. 13/757,668 are continuations of International Appl. No. PCT/US2012/062826, filed Oct. 31, 2012, which claims benefit to U.S. Prov. Appl. No. 61/553,878, filed Oct. 31, 2011. The entire disclosure of the above-listed applications are hereby incorporated by reference in their entireties.

REFERENCE TO SEQUENCE LISTING SUBMITTED ELECTRONICALLY VIA EFS-WEB

The content of the electronically submitted sequence listing (Name: 3338_0010005_Seqlisting.ST25.txt; Size: 145,716 bytes; Date of Creation: Sep. 24, 2019) submitted in this application is incorporated herein by reference in its entirety.

INTRODUCTION

Fibronectin is a large protein which plays essential roles in the formation of extracellular matrix and cell-cell interactions; it consists of many repeats of three types (types I, II, and III) of small domains. Fibronectin type III domains (Fn3) are a large subfamily, members of which are frequently found as portions of cell adhesion molecules, cell surface hormone and cytokine receptors, chaperones, and carbohydrate-binding domains. For reviews see Bork & Doolittle, *Proc Natl Acad Sci USA* 89(19):8990-4 (1992); Bork et al., *J Mol Biol.* 242(4):309-20 (1994); Campbell & Spitzfaden, Structure 2(5):333-7 (1994); Harpez & Chothia, *J Mol Biol.* 238(4):528-39 (1994)).

Fibronectin based scaffolds are a family of proteins having an immunoglobulin like fold. These proteins, which generally make use of a scaffold derived from a fibronectin type III (Fn3) or Fn3-like domain, function in a manner characteristic of natural or engineered antibodies (that is, polyclonal, monoclonal, or single-chain antibodies) and, in addition, possess structural advantages. Specifically, the structures of these antibody mimics have frequently been optimized for optimal folding, stability, and solubility, even under conditions that normally lead to the loss of structure and function in antibodies. An example of fibronectin-based scaffold proteins are Adnectins™ (Adnexus, a wholly owned subsidiary of Bristol-Myers Squibb). It has been shown that the CDR-like loop regions of the fibronectin based scaffolds can be modified to evolve a protein capable of binding to any compound of interest. For example, U.S. Pat. No. 7,115,396 describes Fn3 domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders.

Protein pharmaceuticals are often associated with some degree of immunogenicity in a patient. These immunogenicity issues may result in reduction in efficacy of the protein therapeutic as well as potentially harmful immune responses in a patient. Accordingly, it would be advantageous to obtain improved fibronectin domain scaffold proteins that are associated with reduced immunogenicity and that can be used for both therapeutic and diagnostic purposes.

SUMMARY

One aspect of the application provides for fibronectin based scaffold polypeptides comprising novel combinations of modified loops and scaffold regions, e.g., the β-strands that are associated with improved target binding. Another aspect of the application provides for novel fibronectin based scaffold polypeptides that are associated with reduced immunogenicity.

In some embodiments, the polypeptides provided herein comprise a human fibronectin type 3 tenth ($^{10}$Fn3) domain, wherein the $^{10}$Fn3 domain comprises (i) a modification in the amino acid sequence of at least one north pole loop selected from the BC, DE and FG loops relative to the corresponding loop of the wild-type human $^{10}$Fn3 domain (SEQ ID NO: 1 or 6), and (ii) a modification in the amino acid sequence of at least one south pole loop selected from the AB, CD and EF loops relative to the corresponding loop of the wild-type human $^{10}$Fn3 domain (SEQ ID NO: 1 or 6), wherein the at least one modified north pole loop and the at least one modified south pole loop contribute to binding the same target. In some embodiments, at least one of the north pole loops or at least one of the south pole loops of the polypeptide has the amino acid sequence of the corresponding loop of the wild-type human $^{10}$Fn3 domain (SEQ ID NO: 1 or 6).

In some embodiments, the polypeptides provided herein comprise a human fibronectin type 3 tenth ($^{10}$Fn3) domain, wherein the $^{10}$Fn3 domain comprises (i) a modification in the amino acid sequence of at least one of loops AB, BC, CD, DE, EF, or FG relative to the corresponding loop of the wild-type human $^{10}$Fn3 domain (SEQ ID NO: 1 or 6), and (ii) a modification in the amino acid sequence of at least one β-strand relative to the corresponding β-strand of the wild-type human $^{10}$Fn3 domain (SEQ ID NO: 1 or 6), wherein the at least one modified loop and the at least one modified β-strand contribute to binding the same target. In some embodiments, the polypeptides may comprise modified amino acid sequences in at least one β-strand and at least two loops. In some embodiments, at least one modified loop of the polypeptide is a north pole loop selected from the BC, DE and FG loops and at least one modified loop is a south pole loop selected from the AB, CD and EF loops and both loops contribute to binding to the target. In some embodiments, at least one loop is not modified, i.e., at least one loop has the amino acid sequence of the corresponding loop of the wild-type human $^{10}$Fn3 domain (SEQ ID NO: 1 or 6).

In some embodiments, the polypeptides provided herein comprise a human fibronectin type 3 tenth ($^{10}$Fn3) domain, wherein the $^{10}$Fn3 domain comprises modifications in the amino acid sequences of the CD and FG loops relative to the sequences of the corresponding loops of the wild-type human $^{10}$Fn3 domain (SEQ ID NO: 1 or 6), and wherein the CD and FG loops contribute to binding to the same target. In some embodiments, at least 3, 4, 5, 6, 7, 8, 9, 10 or 11 of the amino acids of the CD loop are modified relative to the sequence of the CD loop of the wild type human ¹⁰Fn3 domain (SEQ ID NO: 1 or 6). In some embodiments, one or more amino acid residues of the CD loop corresponding to amino acid residues 46 or 47 of the wild-type human ¹⁰Fn3 domain (SEQ ID NO: 1 or 6) are the same as the wild-type amino acids at those positions. In some embodiments, at least 3, 4, 5, 6, 7, 8, 9, 10, 11, 12 or 13 of the amino acids of the FG loop are modified relative to the sequence of the FG loop of the wild-type human ¹⁰Fn3 domain (SEQ ID NO: 1 or 6). In some embodiments, one or more amino acid residues of the FG loop corresponding to amino acid residues 75 or 87 of the wild-type human ¹⁰Fn3 domain (SEQ ID NO: 1 or 6) are the same as the wild-type amino acids at those positions. In some embodiments, the amino acid sequence of the CD loop, the FG loop, or both are extended in length or reduced in length relative to the amino acid sequence of the corresponding loop of the wild-type human ¹⁰Fn3 domain (SEQ ID NO: 1 or 6). Combinations thereof are also contemplated. For example, the amino acid sequence of at least one of the CD and FG loops may be extended in length relative to the corresponding loop of the wild-type human ¹⁰Fn3 domain (SEQ ID NO: 1 or 6) and the amino acid sequence of at least one of the CD and FG loops may be reduced in length relative to the corresponding loop of the wild-type human ¹⁰Fn3 domain (SEQ ID NO: 1 or 6). In some embodiments, polypeptides comprising ¹⁰Fn3 domains having modified CD and FG loops, may further comprise amino acid sequence modifications in one or more of β-strand C, and β-strand D, β-strand F and/or β-strand G relative to the sequences of the corresponding β-strands of the wild-type human ¹⁰Fn3 domain (SEQ ID NO: 1 or 6). In some embodiments, the polypeptides having modified CD and FG loops may further comprise an amino acid sequence modification in at least a portion of the BC loop, such as, for example, modifications in one or more amino acid residues of the BC loop corresponding to amino acid residues 30 and 31 of the wild-type human ¹⁰Fn3 domain (SEQ ID NO: 1 or 6). In some embodiments, one or more of the modified β-strands, together with the modified loops, contribute to binding to the same target. In some embodiments, one or more of the AB, DE and EF loops are not modified, i.e., the loops have the amino acid sequence of the corresponding loop of the wild type human ¹⁰Fn3 domain (SEQ ID NO: 1 or 6).

In some embodiments, the polypeptides provided herein comprise a human fibronectin type 3 tenth (¹⁰Fn3) domain, wherein the ¹⁰Fn3 domain comprises modifications in the amino acid sequences of the CD and DE loops relative to the sequences of the corresponding loops of the wild-type human ¹⁰Fn3 domain (SEQ ID NO: 1 or 6), and wherein the CD and DE loops contribute to binding to the same target. The polypeptide may further comprise modifications in the amino acid sequences of one or more of the EF loop, β-strand C, β-strand D, and/or β-strand F, and such additional modification may contribute to binding to the same target together with the CD and DE loops. In some embodiments, at least 10, 15, 16, 18, 20, 21, 22, 23, 24, 25, 26, 27, 28, 29, 30 or all 31 of the residues between the amino acids corresponding to residues 36 through 66 of the wild-type human ¹⁰Fn3 domain (SEQ ID NO: 1 or 6) have been modified relative to the corresponding residues in the wild-type sequence. In some embodiments, the CD loop is extended in length or reduced in length relative to the CD loop of the wild-type human ¹⁰Fn3 domain (SEQ ID NO: 1 or 6).

In some embodiments, the polypeptides provided herein comprise a human fibronectin type 3 tenth (¹⁰Fn3) domain, wherein the ¹⁰Fn3 domain comprises modifications in the amino acid sequences of the EF and FG loops relative to the sequences of the corresponding loops of the wild-type human ¹⁰Fn3 domain (SEQ ID NO: 1 or 6), and wherein the EF and FG loops contribute to binding to the same target. In some embodiments, the polypeptides may further comprise amino acid sequence modifications in one or more of the AB loop, β-strand A and/or β-strand G, and such additional modifications may contribute to binding to the target together with the EF and FG loops. In some embodiments, the polypeptides may further comprise sequence modifications in the N-terminus and/or C-terminus. In particular, the amino acid sequence of the first 7 amino acids or the amino acid sequence of the amino acids corresponding to residues 93 through 97 of the wild-type human ¹⁰Fn3 domain (SEQ ID NO: 1 or 6) may be modified relative to the corresponding residues in the wild-type sequence. These additional modifications at the termini may also contribute to binding to the target along with the other sequence modifications. In some embodiments, at least 2, 3, 4, 5, 6, 7, 8, 9, 10, 11, 12, 13, 14 or all 15 of the first 15 amino acid residues of the ¹⁰Fn3 domain may be modified relative to the corresponding residues in the wild-type human ¹⁰Fn3 domain (SEQ ID NO: 1 or 6). In some embodiments, at least 3, 4 or 5 of the amino acid residues of the EF loop may be modified relative to the corresponding residues in the wild-type human ¹⁰Fn3 domain (SEQ ID NO: 1 or 6). In some embodiments, at least 2, 3, 4, 5, 6, 7, 8, 9, 10, 11, 12, 13, 14, 15, 16, 17 or all 18 of the residues between the amino acids corresponding to residues 80 through 97 of the wild-type human ¹⁰Fn3 domain (SEQ ID NO: 1 or 6) may be modified relative to the corresponding residues in the wild-type sequence. In some embodiments, the amino acid sequence of the FG loop is extended in length or reduced in length relative to the FG loop of the wild type human ¹⁰Fn3 domain (SEQ ID NO: 1 or 6).

In some embodiments, the polypeptides provided herein comprise a human fibronectin type 3 tenth (¹⁰Fn3) domain, wherein the ¹⁰Fn3 domain comprises modifications in the amino acid sequences of β-strand A, loop AB, β-strand B, loop CD, β-strand E, loop EF, and β-strand F relative to the sequences of the corresponding β-strands and loops of the wild-type human ¹⁰Fn3 domain (SEQ ID NO: 1 or 6), and wherein the modified loops and strands contribute to binding to the same target. In some embodiments, the amino acid sequence of the CD loop is extended in length or reduced in length relative to the CD loop of the wild-type human ¹⁰Fn3 domain (SEQ ID NO: 1 or 6). In some embodiments, the polypeptides may further comprise a modification in the amino acid sequence of β-strand G and/or the C terminal tail.

In some embodiments, the polypeptides provided herein comprise a human fibronectin type 3 tenth (¹⁰Fn3) domain, wherein the ¹⁰Fn3 domain comprises a sequence modification in the FG loop relative to the sequence of amino acid residues 77-83 of loop FG of the wild-type human ¹⁰Fn3 domain (SEQ ID NO: 1 or 6), and wherein the ¹⁰Fn3 binds to a target with a $K_d$ of less than 500 nM. In some embodiments, the portion of the FG loop corresponding to amino acid residues 77-83 of the wild-type human ¹⁰Fn3 domain (SEQ ID NO: 1 or 6) is extended in length or reduced in length relative to the sequence of amino acid residues 77-83 of the wild-type FG loop. In some embodiments, the FG loop alone mediates binding to the target. In some embodiments, one of more of the AB, BC, CD, DE or EF loops has the sequence of the corresponding loop of the wild-type human ¹⁰Fn3 domain (SEQ ID NO: 1 or 6).

In some embodiments, the polypeptides provided herein comprise a human fibronectin type 3 tenth ($^{10}$Fn3) domain, wherein the $^{10}$Fn3 domain comprises a sequence modification in the BC loop and at least one of β-strand B or β-strand C relative to the sequences of the corresponding loop and β-strands of the wild-type human $^{10}$Fn3 domain (SEQ ID NO: 1 or 6), and wherein the $^{10}$Fn3 domain has reduced immunogenicity relative to an equivalent $^{10}$Fn3 domain that does not have a sequence modification in at least one of β-strand B or β-strand C relative to wild-type. In some embodiments, the amino acid sequence of the BC loop is extended in length or reduced in length relative to the amino acid sequence of the BC loop of the wild-type human $^{10}$Fn3 domain (SEQ ID NO: 1 or 6). In some embodiments, the $^{10}$Fn3 domain further comprises a modification in the amino acid sequence of the first 7 amino acid residues relative to the amino acid sequence of the first 7 amino acid residues of the wild-type human $^{10}$Fn3 domain (SEQ ID NO: 1 or 6). In some embodiments, the $^{10}$Fn3 domain further comprises a modification in the DE loop, the FG loop, or both, relative to the sequences of the corresponding loops of the wild-type human $^{10}$Fn3 domain (SEQ ID NO: 1 or 6). In some embodiments, the amino acid sequence of the DE loop is extended in length or reduced in length relative to the amino acid sequence of the DE loop of the wild-type human $^{10}$Fn3 domain (SEQ ID NO: 1 or 6). In some embodiments, the amino acid sequence of the FG loop is extended in length or reduced in length relative to the amino acid sequence of the FG loop of the wild-type human $^{10}$Fn3 domain (SEQ ID NO: 1 or 6). In some embodiments, the $^{10}$Fn3 domain comprises a sequence modification in the DE loop, and further comprises a sequence modification in β-strand D, β-strand E, or both, relative to the sequences of the corresponding β-strands of the wild-type human $^{10}$Fn3 domain (SEQ ID NO: 1 or 6). In some embodiments, the $^{10}$Fn3 domain comprises a sequence modification in the FG loop, and further comprises a sequence modification in β-strand F, β-strand G, or both, relative to the sequences of the corresponding β-strands of the wild-type human $^{10}$Fn3 domain (SEQ ID NO: 1 or 6).

In some embodiments, at least a portion of the BC loop of the polypeptides provided herein have the amino acid sequence of the corresponding loop of the wild-type human $^{10}$Fn3 domain (SEQ ID NO: 1 or 6). For example, the first 1, 2, 3, 4, 5, 6, 7 or 8 residues of the BC loop may be the same as the corresponding residues in the BC loop of the wild type human $^{10}$Fn3 domain (SEQ ID NO: 1 or 6). In still other embodiments, the entire BC loop has the amino acid sequence of the corresponding loop of the wild type human $^{10}$Fn3 domain (SEQ ID NO: 1 or 6). In some embodiments, polypeptides having at least a portion of the BC loop with the wild-type sequence have reduced immunogenicity relative to an equivalent polypeptide having additional modifications in the BC loop.

In particular embodiments, the polypeptides provided herein comprise a human fibronectin type 3 tenth ($^{10}$Fn3) domain, wherein the $^{10}$Fn3 domain comprises a sequence modification in a portion of the BC loop and a portion of the FG loop relative to the sequence of the corresponding loops of the wild-type human $^{10}$Fn3 domain (SEQ ID NO: 1 or 6), and wherein the $^{10}$Fn3 domain has reduced immunogenicity relative to an equivalent $^{10}$Fn3 domain having a greater portion of the BC loop modified relative to the wild-type BC loop. In some embodiments, the portion of the BC loop that is modified may correspond to residues 28-29, 27-29, 26-29, 25-29, or 24-29 of the BC loop of the wild-type human $^{10}$Fn3 domain (SEQ ID NO: 1 or 6). In some embodiments, the portion of the FG loop that is modified may corresponds to residues 77-79, 77-80, 77-81, 77-82, 77-83, 77-84, 77-85, or 77-86 of the FG loop of the wild-type human $^{10}$Fn3 domain (SEQ ID NO: 1 or 6). In some embodiments, the portion of the FG loop that is modified has an insertion or deletion relative to the corresponding portion of the FG loop of the wild-type human $^{10}$Fn3 domain (SEQ ID NO: 1 or 6). In some embodiments, the BC and FG loop contribute to binding to the target. In some embodiments, the $^{10}$Fn3 domain further comprises a sequence modification in a portion of the DE loop relative to the sequence of the DE loop of the wild-type human $^{10}$Fn3 domain (SEQ ID NO: 1 or 6). In some embodiments, the portion of the DE loop that is modified corresponds to residues 52 and 53 of the BC loop of the wild-type human $^{10}$Fn3 domain (SEQ ID NO: 1). In some embodiments, the $^{10}$Fn3 domain has reduced immunogenicity relative to an equivalent $^{10}$Fn3 domain further comprising modifications in one or more of amino acid residues 23-27, relative to the corresponding positions in the wild-type BC loop. In some embodiments, the $^{10}$Fn3 domain binds to a target with a $K_d$ of less than 500 nM.

In some embodiments, the FG loop of the polypeptides provided herein does not contain an RGD integrin binding site.

In some embodiments, the hydrophobic core residues of the polypeptides provided herein have not been modified relative to the wild type human $^{10}$Fn3 domain (SEQ ID NO: 1 or 6).

In some embodiments, the amino acid sequence of at least one of the modified loops of the polypeptides provided herein has been extended in length relative to the amino acid sequence of the corresponding loop of the wild-type human $^{10}$Fn3 domain (SEQ ID NO: 1 or 6). In other embodiments, the amino acid sequence of at least one of the modified loops has been reduced in length relative to the amino acid sequence of the corresponding loop of the wild-type human $^{10}$Fn3 domain (SEQ ID NO: 1 or 6).

In some embodiments, the amino acid sequence of the C terminal tail of the polypeptides provided herein is modified relative to the amino acid sequence of the C-terminal tail of the wild-type human $^{10}$Fn3 domain (SEQ ID NO: 1 or 6). In some embodiments, the amino acid sequence of the first 7 amino acid residues is modified relative to the amino acid sequence of the first 7 amino acid residues of the wild type human $^{10}$Fn3 domain (SEQ ID NO: 1 or 6). In other embodiments, the polypeptide has from 1-7 amino acids truncated from the N-terminus relative to the wild-type human $^{10}$Fn3 domain (SEQ ID NO: 1 or 6), from 1-9 amino acids truncated from the C-terminus relative to the wild-type human $^{10}$Fn3 domain (SEQ ID NO: 1), or both.

In some embodiments, the polypeptides provided herein have at least 50% identity to the amino acid sequence of the wild-type human $^{10}$Fn3 domain (SEQ ID NO: 1, 2, 60 or 6). In other embodiments, the polypeptide has at least 65% identity to the amino acid sequence of the wild-type human $^{10}$Fn3 domain (SEQ ID NO: 1, 2, 60 or 6). In certain embodiments, the $^{10}$Fn3 domains comprise an amino acid sequence that is at least 60, 70, 80 or 90% identical to the naturally occurring human $^{10}$Fn3 domain represented by SEQ ID NO: 1, 2, 60 or 6.

In some embodiments, the polypeptides provided herein comprise a fibronectin type III tenth ($^{10}$Fn3) domain, wherein the $^{10}$Fn3 domain comprises an amino acid sequence having at least 60% identity to SEQ ID NO: 2 or 60 and binds to a target molecule with a $K_d$ of less than 100 nM, and wherein the $^{10}$Fn3 domain further comprises a C-terminal tail that does not contain a DK sequence. In some embodiments, the C-terminal tail comprises the amino acid sequence of SEQ ID NO: 7. In some embodiments, the C-terminal tail further comprises a cysteine residue. In other embodiments, the C-terminal tail comprises the sequence of SEQ ID NO:8. In other embodiments, the C-terminal tail may comprise the sequence of any one of SEQ ID NOs: 23-31.

In certain embodiments, the fibronectin based scaffold proteins bind to a target that is not bound by a wild-type $^{10}$Fn3 domain.

In some embodiments, the $^{10}$Fn3 domains of the fibronectin based scaffold protein further comprises an N-terminal extension comprising from 1-10 amino acids. In certain embodiments, the $^{10}$Fn3 domain comprises an M, MG or G N-terminal to first amino acid of SEQ ID NO: 1 or 6. In other embodiments, the amino acid residues corresponding to amino acids 1-8 of SEQ ID NO:1 or 6 are replaced with any one of SEQ ID NOs: 9-11 or 16-21.

In some embodiments, the fibronectin based scaffold proteins further comprise one or more pharmacokinetic (PK) moieties selected from: a polyoxyalkylene moiety, a human serum albumin binding protein, sialic acid, human serum albumin, transferrin, IgG, an IgG binding protein, and an Fc fragment. In some embodiments, the PK moiety is the polyoxyalkylene moiety and said polyoxyalkylene moiety is polyethylene glycol (PEG). In some embodiments, the PEG moiety is covalently linked to the fibronectin based scaffold protein via a Cys or Lys amino acid. In some embodiments, the PEG is between about 0.5 kDa and about 100 kDa.

In certain embodiments, the application provides pharmaceutically acceptable compositions comprising the novel $^{10}$Fn3 domains described herein. In some embodiments, the composition is essentially pyrogen free. In some embodiments, the composition is substantially free of microbial contamination making it suitable for in vivo administration. The composition may be formulated, for example, for intravenous (IV), intraperitoneal (IP) or subcutaneous (SubQ) administration. In some embodiments, the composition comprises a physiologically acceptable carrier. In some embodiments, the pH of the composition is between 4.0-6.5, between 4.0-5.5, or is equal to 4.0, 4.5, 5.0 or 5.5. In some embodiments, the concentration of the fibronectin based scaffold protein is 5 mg/ml in the composition.

In certain embodiments, the application provides a nucleic acid encoding the novel $^{10}$Fn3 domains as described herein. Vectors containing polynucleotides for such proteins are included as well. Suitable vectors include, for example, expression vectors. A further aspect of the application provides for a cell, comprising a polynucleotide, vector, or expression vector, encoding a $^{10}$Fn3 domain. Sequences are preferably optimized to maximize expression in the cell type used. In some embodiments, expression is in a bacterial cell, such as E. coli. In other embodiments, expression is in a mammalian cell. In one embodiment, the cell expresses a protein comprising a $^{10}$Fn3 domain as described herein. In certain embodiments, the polynucleotides encoding a $^{10}$Fn3 domain are codon optimized for expression in the selected cell type. Also provided are methods for producing a $^{10}$Fn3 domain as described herein, comprising culturing a host cell comprising a nucleic acid, vector, or expression vector encoding a $^{10}$Fn3 domain and recovering the expressed protein from the culture.

In certain embodiments, the application provides libraries of the fibronectin based scaffold proteins described herein. The libraries provided herein may comprise, for example, at least $10^5$, $10^6$, $10^7$, $10^8$, $10^9$, $10^{10}$, $10^{12}$, $10^{13}$, or $10^{14}$, or more members. Also provided are methods for isolating a fibronectin based scaffold protein that specifically binds to a target of interest from one of the libraries described herein. For example, a library isolation method may comprise, for example, contacting a library of fibronectin based scaffold proteins with a target of interest, and isolating members of the library that bind to the target (e.g., with a particular affinity or under suitable wash conditions). The isolation step may be carried out using any suitable method, such as phage display or mRNA display. Similarly, target binding may be conducted using any suitable method such as immobilizing the target on a solid support (e.g., a column, chip, bead, etc.) and mixing the immobilized target with the library under conditions suitable to allow protein binding. The bound library members may then be separated from unbound library members to yield an isolated fibronectin based scaffold protein that binds to the target. In certain embodiments, the isolation method may involve repeated rounds of target binding and isolation steps.

BRIEF DESCRIPTION OF THE FIGURES

FIG. 1: The wildtype $^{10}$Fn3 amino acid sequence (SEQ ID NO: 1) in which the hydrophobic core amino acid residues are indicated. The beta-strands are in bold, loop regions are designated by letter pairs, and the hydrophobic core residues are underlined in bold. Amino acids 95-101 correspond to a tail, which when absent from a $^{10}$Fn3 molecule having SEQ ID NO: 1 forms a 10Fn3 molecule having SEQ ID NO: 6.

FIG. 2: Wildtype $^{10}$Fn3 amino acid sequences (SEQ ID NO: 1 or 6) in which amino acid positions that may be mutated to provide a representative modified $^{10}$Fn3 polypeptide patch library are indicated in the full-length sequence (SEQ ID NO: 1). Potential positions that may be modified to generate each of the respective classes of patch library $^{10}$Fn3 polypeptides are in bold and underlined. Any one of, or combination of, the positions indicated may be mutated to generate either Northwest Binders (SEQ ID NO 73), Northeast Binders (SEQ ID NO: 74), West Side Binders (SEQ ID NO: 75), South-Front Binders (SEQ ID NO: 76), AG Strand Binders (SEQ ID NO: 77), and SouthWest Binders (SEQ ID NO: 78).

FIGS. 3A, 3B, 3C, 3D, 3E, and 3F: Crystal structures of the wildtype $^{10}$Fn3 domain, in which views of different possible binding interfaces are shown. Residues that may be varied from wild-type are shown in black. Sticks are added to varied residues that are not members of one of the six loops. Crystal structure views of the Northwest binding interface (FIG. 3A), Northeast binding interface (FIG. 3B), West Side binding interface (FIG. 3C), South-Front binding interface (FIG. 3D), AG Strand binding interface (FIG. 3E) and SouthWest binding interface (FIG. 3F) of the wildtype $^{10}$Fn3 domain are shown.

FIG. 4: HLA-binding data showing the IC$_{50}$ binding affinity (µM) of five different HLA allele proteins to five different peptide segments of the $^{10}$Fn3 polypeptide. SEQ ID NOs: 58, 51 and 52 are loop region clusters of the BC, DE and FG loops, respectively, with loop region residues underlined. SEQ ID NOs: 53 and 54 are a wildtype and modified scaffold region segment of the $^{10}$Fn3 polypeptide, respectively. As indicated, the BC loop region cluster (SEQ ID NO: 58) and the two scaffold region peptide segments tested (SEQ ID NOs: 53 and 54) were strong binders (<25 µM) of most of the HLA allele proteins tested. The predicted immunodominant regions of the scaffold region peptide segments (SEQ ID NOs: 53 and 54) are underlined.

Figure 6:
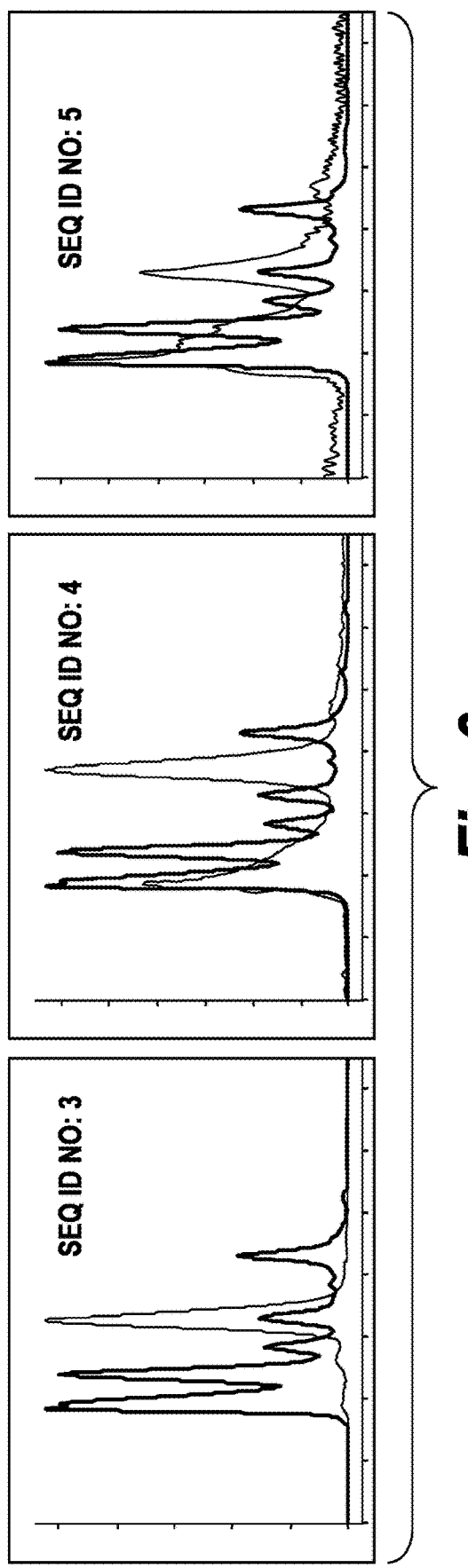

FIG. 6: Size Exclusion Chromatography results showing that the WS-LI1 binder of SEQ ID NO: 3 was predominantly monomeric, while the WS-LI1 binders of SEQ ID NOs: 4 and 5 contained a mixture of monomeric and aggregated proteins. Bold traces correspond to the WS-LI1 binder tested, and non-bold traces correspond to molecular weight markers, with the expected elution of the WS-LI1 binder monomers to be eluted between the $3^{rd}$ and $5^{th}$ marker peaks.

Figure 7:
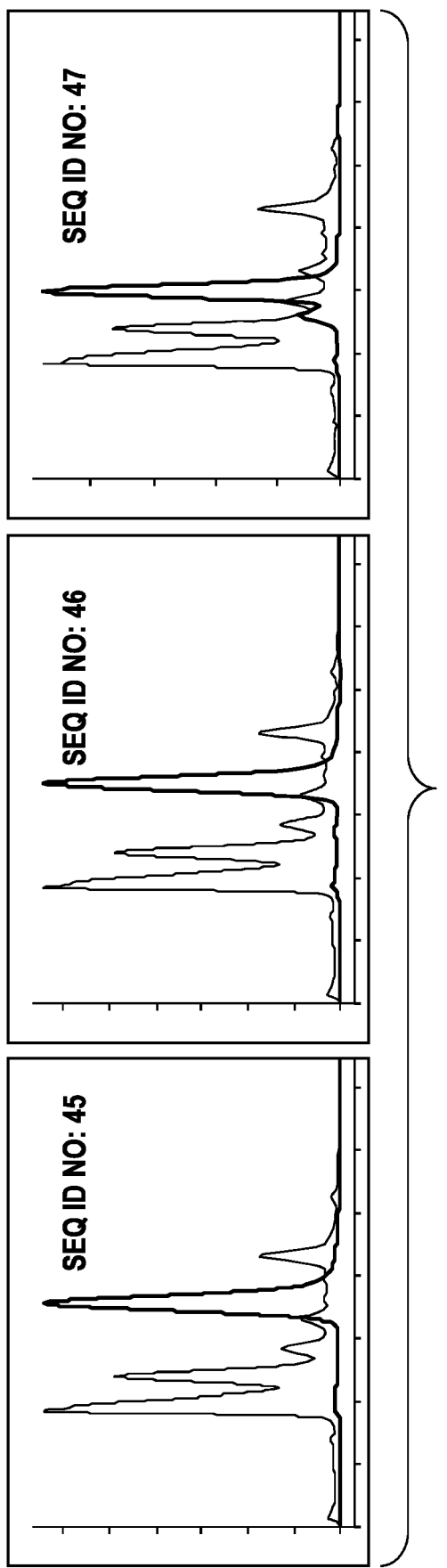

FIG. 7: Size Exclusion Chromatography results showing that the WS-LI1 binders of SEQ ID NOs: 45-47 were predominantly monomeric. Bold traces correspond to the WS-LI1 binders tested, and non-bold traces correspond to molecular weight markers, with the expected elution of the WS-LI1 binder monomers to be eluted between the $3^{rd}$ and $5^{th}$ marker peaks.

Figure 8:
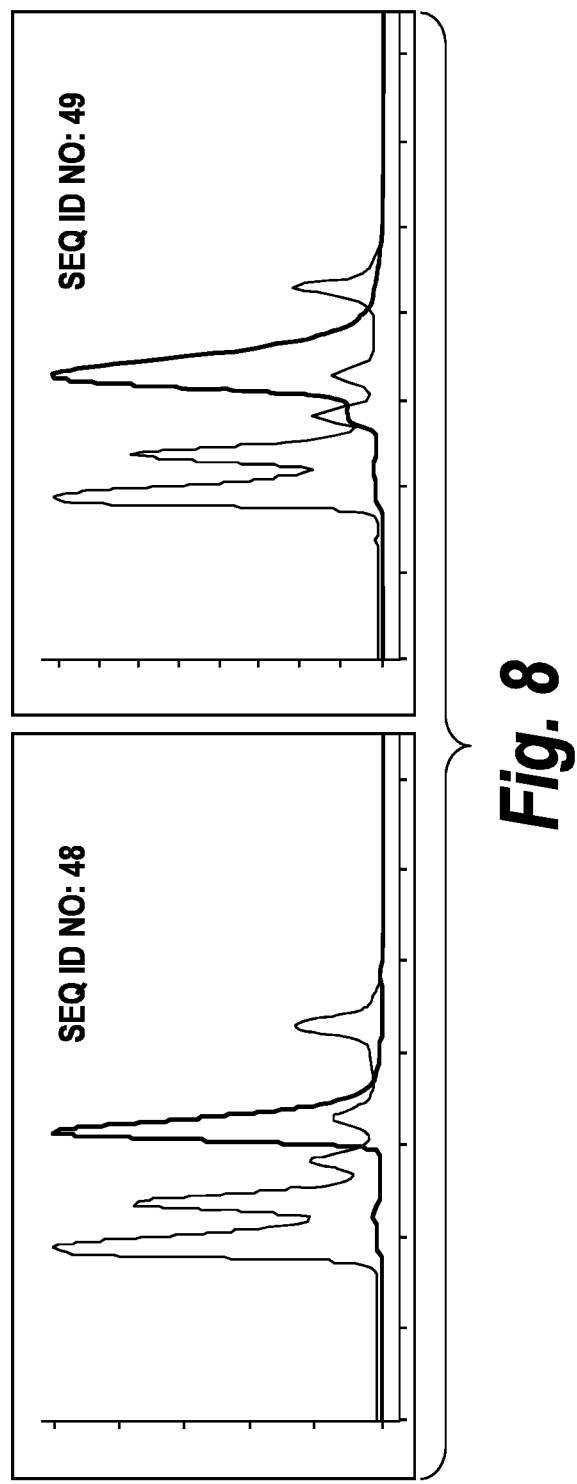

FIG. 8: Size Exclusion Chromatography results showing that the WS1 binders of SEQ ID NOs: 48-49 were predominantly monomeric. Bold traces correspond to the WS1 binders tested, and non-bold traces correspond to molecular weight markers, with the expected elution of the WS1 binder monomers to be eluted between the $3^{rd}$ and $5^{th}$ marker peaks.

FIGS. 9A, 9B, and 9C: Library designs for non-traditional $^{10}$Fn3 binders. FIG. 9A shows library designs in which the BC loop is substantially or completely unmodified (i.e., all or most of the BC loop is left as the wild-type sequence). All of the CD and FG loops of the libraries depicted in FIG. 9A may be varied in size, in particular, loop CD of SP1, WS2', WS2'-CD, Front3 and CD1-loop may be varied in length. Loop FG of Back3 may also be varied in size, and the first three amino acids of CD1-loop (i.e., VSD) may be deleted. FIG. 9B shows library designs in which varying portions of the N-terminus of the BC loop have been left as wild-type. FIG. 9C shows library designs in which the BC loop and one or both of the β-strand regions flanking the BC loop are modified. Library NP-6 may also be constructed by keeping the threonine at position 71 constant and/or by keeping the length of amino acids 1-7 constant. Library NP4-5 may also be constructed by keeping the threonine at position 71 constant, and/or by keeping the length of amino acids 1-7 constants, and/or by keeping loop BC constant. In each of FIGS. 9A, 9B, and 9C, the full-length wild type $^{10}$Fn3 domain (SEQ ID NO: 1) is shown at the top with numbering from amino acid 1 to amino acid 101 and markings indicating the loop and strand regions. Below the depiction of the $^{10}$Fn3 wild-type domain is a depiction of a classic north pole library design (i.e., with the BC, DE and FG loops modified) (SEQ ID NO: 79). The non-traditional library designs are shown below the classic north pole library design. Positions that may be modified by substitution are indicated in bold and underlined, regions that may be modified by substitution, insertion and/or deletion are in bold and boxed, and amino acid residues that are non-wild-type are shaded. In FIG. 9B, all sequences are based on SEQ ID NO: 1. The library designs shown in FIG. 9B include: LI-3(b) (SEQ ID NO: 102), LI-1(a) (SEQ ID NO: 103), LI-1(b) (SEQ ID NO: 104), LI-1(c) (SEQ ID NO: 105), LI-2(a) (SEQ ID NO: 106), LI-2(b) (SEQ ID NO: 107), NW3 (SEQ ID NO: 108), and NP6-2 (SEQ ID NO: 109). In FIG. 9C, the WT $^{10}$Fn3 (SEQ ID NO: 1), Classic NP (SEQ ID NO: 79), NP1 (SEQ ID NO: 110), NE1 (SEQ ID NO: 111), NP4-5 (SEQ ID NO: 112), NP6-1 (SEQ ID NO: 113), and NW2 (SEQ ID NO: 114) sequences are disclosed based on SEQ ID NO: 1; and all remaining sequences (i.e., NP1' (SEQ ID NO: 115), NE1' (SEQ ID NO: 116), NP4 (SEQ ID NO: 117), NP4-FG (SEQ ID NO: 118), NP5 (SEQ ID NO: 119), and NP6-3 (SEQ ID NO: 120)) are disclosed based on SEQ ID NO: 59. In FIG. 9A, the WT $^{10}$Fn3 (SEQ ID NO: 1), Classic NP (SEQ ID NO: 79), WS1 (SEQ ID NO: 80), WS2 (SEQ ID NO: 81), WS3 (SEQ ID NO: 82), LI-3(a) (SEQ ID NO: 90), WS-LI1 (SEQ ID NO: 91), WS2' (SEQ ID NO: 96), and WS2'-CD (SEQ ID NO: 97) are based on SEQ ID NO: 1; and all remaining sequences (i.e., Front1 (SEQ ID NO: 83), Front2 (SEQ ID NO: 84), Back1 (SEQ ID NO: 85), Back2 (SEQ ID NO: 86), SP1 (SEQ ID NO: 87), SP2 (SEQ ID NO: 88), SP3 (SEQ ID NO: 89), LI-S9 (SEQ ID NO: 92), SouthFront (SEQ ID NO: 93), AG Strand (SEQ ID NO: 94), SouthWest (SEQ ID NO: 95), Front3 (SEQ ID NO: 98), Back3 (SEQ ID NO: 99), LI-S8 (SEQ ID NO: 100), and CD1-loop (SEQ ID NO: 101)) are based on SEQ ID NO: 59. All libraries may also be based on SEQ ID NO: 6 or SEQ ID NO: 12, i.e., lacking amino acids 95-101 of SEQ ID NOS 1 and 59, respectively.

Figure 10:
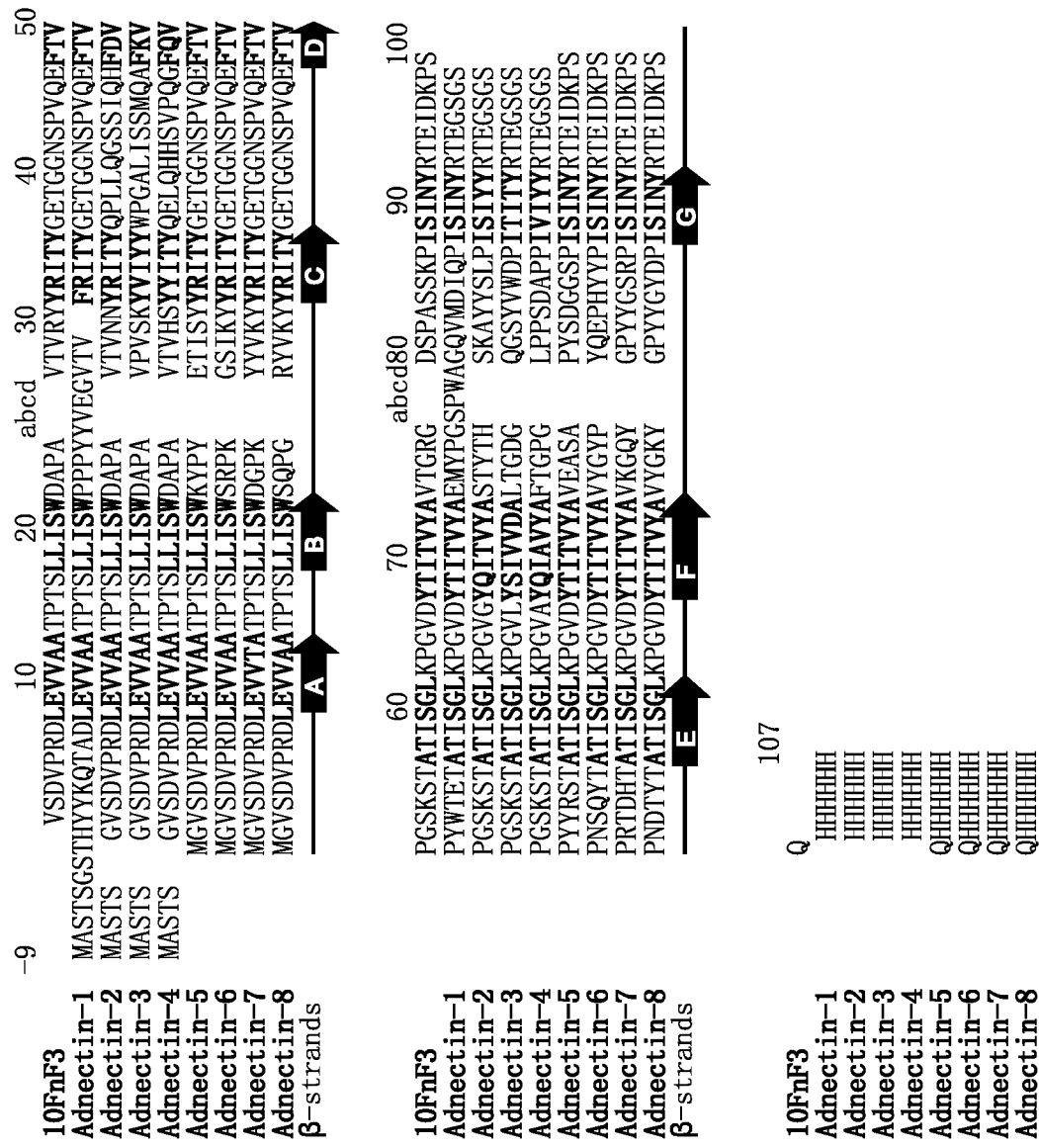

FIG. 10: Sequence alignment of 8 $^{10}$Fn3 polypeptides (Adnectin-1 to Adnectin-8), which bind specifically to human PXR ligand binding domain, with the parent $^{10}$Fn3 domain (SEQ ID NO: 1). The location of the β-strands is indicated by the arrows below the sequence alignment, with corresponding amino acids indicated in bold. Adnectins-3 (SEQ ID NO: 62) and -4 (SEQ ID NO: 63) correspond to SEQ ID NOs: 48 and 49 with an additional 6×His tail (SEQ ID NO: 44). Adnectins-1, -2, -5, -6, -7 and -8 (SEQ ID NOs: 70-72 and 13-15, respectively) correspond to SEQ ID NOs: 64-69, respectively, with an additional 6×His tail (SEQ ID NO: 44).

Figure 11:
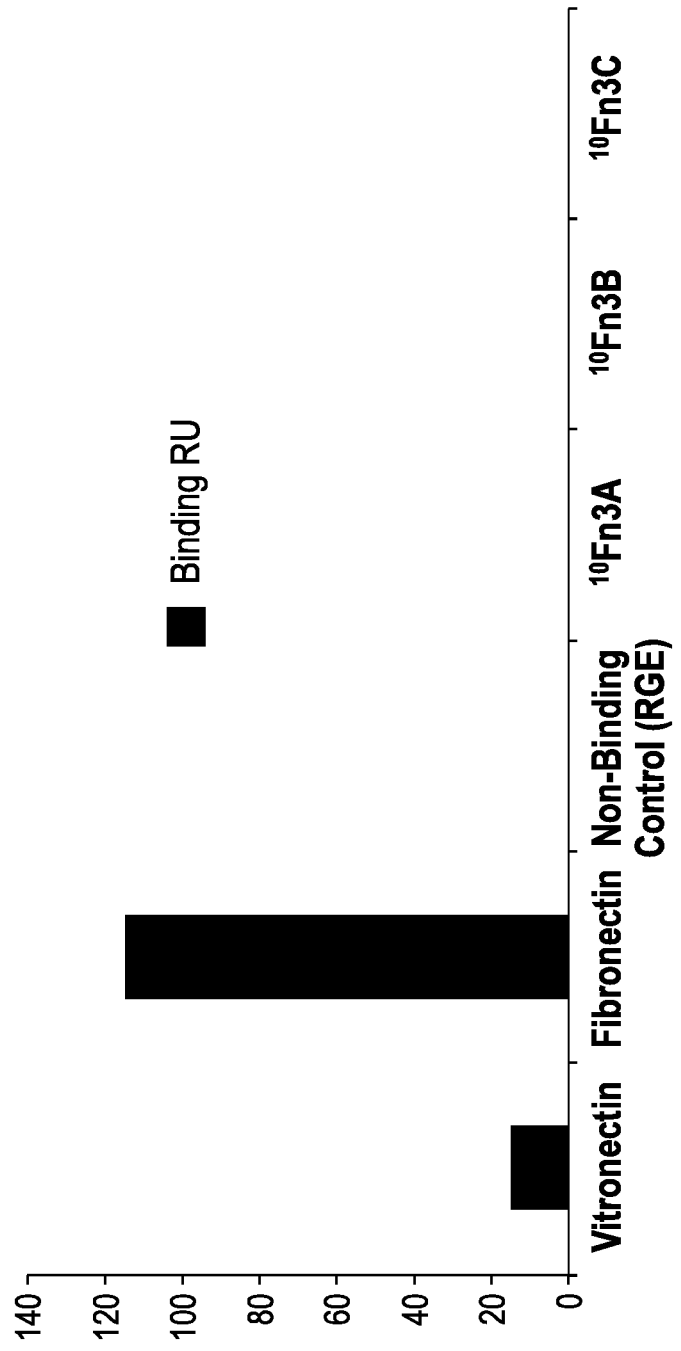

FIG. 11: Histogram showing the degree of binding of (from left to right) vitronectin, fibronectin, a non-binding control adnectin (with RGD changed to RGE), and three different $^{10}$Fn3 molecules binding to a specific target and not comprising an RGD sequence ($^{10}$Fn3 A, B and C, respectively) to immobilized integrin AlphaV-Beta3.

Figure 12:
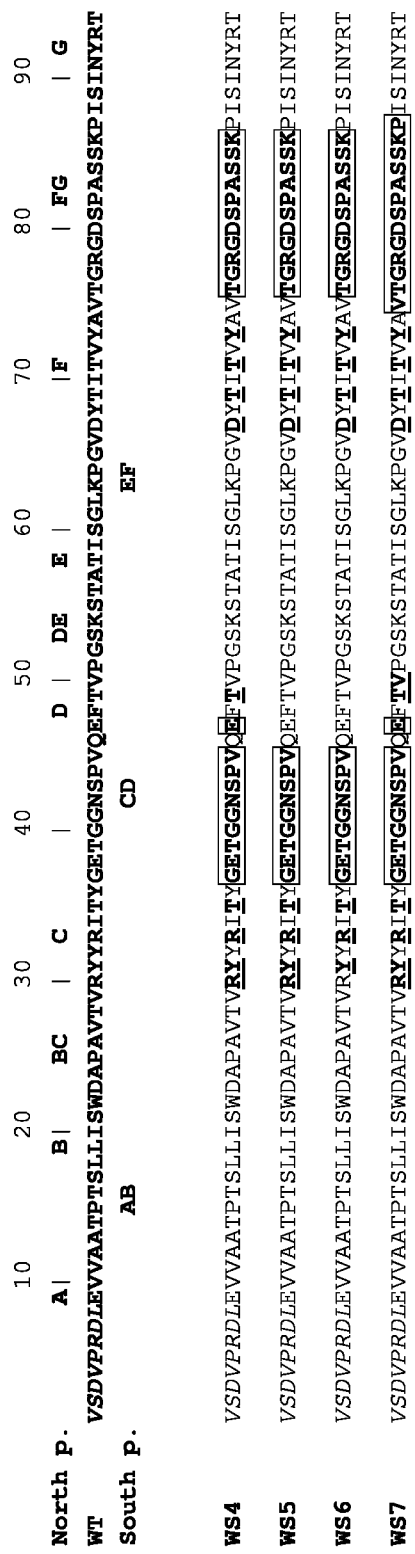

FIG. 12: Amino acid sequences of wild type human $^{10}$Fn3 (SEQ ID NO: 6) (top line) and those of libraries WS4 (SEQ ID NO: 121), WS5 (SEQ ID NO: 122), WS6 (SEQ ID NO: 123), and WS7 (SEQ ID NO: 124). The underlined bolded and boxed amino acids can be changed by substitution, deletion and addition. The underlined amino acids can be changed by substitution.

DETAILED DESCRIPTION

Definitions

By a "polypeptide" is meant any sequence of two or more amino acids, regardless of length, post-translation modification, or function. "Polypeptide," "peptide," and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "region" of a $^{10}$Fn3 domain as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-101 of SEQ ID NO: 1) of the human $^{10}$Fn3 domain.

A "north pole loop" refers to any one of the BC, DE and FG loops of a fibronectin human fibronectin type 3 tenth ($^{10}$Fn3) domain.

A "south pole loop" refers to any one of the AB, CD and EF loops of a fibronectin human fibronectin type 3 tenth ($^{10}$Fn3) domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-101 of SEQ ID NO: 1).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wild-type $^{10}$Fn3 (e.g., SEQ ID NO: 1 or 6), to alanine, or to a residue having a similarly sized or smaller side chain than the residue in question, leads to a measured increase of the equilibrium dissociation constant to the target (e.g., an increase in the $k_{on}$).

The "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., Chemical Stability of Pharmaceuticals: A Handbook for Pharmacists (1986); Peters et al, Pharmacokinete analysis: A Practical Approach (1996); and "Pharmacokinetics", M Gibaldi & D Perron, published by Marcel Dekker, 2nd Rev. edition (1982).

Half-life can be expressed using parameters such as the t½-alpha, t½-beta and the area under the curve (AUC). In the present specification, an "increase in half-life" refers to an increase in any one of these parameters, any two of these parameters, or in all three these parameters. In certain embodiments, an increase in half-life refers to an increase in the t½-beta, either with or without an increase in the t½-alpha and/or the AUC or both.

Overview $^{10}$Fn3 domains are structurally and functionally analogous to antibodies, specifically the variable region of an antibody. Historically, designs of $^{10}$Fn3 binding domains having relied on the similarity of the $^{10}$Fn3 domain structure to that of the VH domain of an antibody. In particular, $^{10}$Fn3 binding domains traditionally have relied on modifications in the amino acid sequences of the CDR-like loops of the $^{10}$Fn3 domain. Each of the AB, BC, CD, DE, EF and FG loops of $^{10}$Fn3 domains is analogous to a complementary determining region (CDR) from an immunoglobulin in that they are flexible and amenable to modifications in their amino acid sequences without altering the overall structure of the $^{10}$Fn3 domain. Furthermore, modifications of sets of the CDR-like loops along one face of the $^{10}$Fn3 domain (i.e., the "north pole") have been shown to permit development of $^{10}$Fn3 domains that binds to a desired target (see e.g., PCT Publication Nos. WO 02/032925, WO 2008/097497, and No. WO 2008/066752). In these traditional $^{10}$Fn3 scaffold designs, the protein sequences between the loops, i.e. the β-strands, are typically not modified or are only minimally modified because they play a role in maintaining the overall structural conformation of the $^{10}$Fn3. We have now surprisingly found that it is possible to modify the $^{10}$Fn3 domains in a non-traditional manner to produce proteins that bind to a desired target while maintaining suitable stability.

In particular, the present application provides fibronectin based scaffold polypeptides comprising novel combinations of modified loops and scaffold regions and that are associated with improved properties. The fibronectin based scaffold proteins described herein comprise one or more human tenth fibronectin type III domains that have been modified so as to bind to one or more desired targets. The present application relates, in part, to the surprising discovery that novel combinations of fibronectin domain loop and/or scaffold region modifications are associated with specific target binding. In particular, it has been discovered that novel scaffold region, e.g. non-loop, modifications in fibronectin-based scaffold proteins may be combined with specific loop modifications to obtain specific target binding. Such novel scaffold designs provide expanded potential for designing [10]Fn3 based binding proteins. For example, the non-traditional scaffold designs described herein permit the creation of libraries with greater diversity by opening up new areas for sequence modification within the [10]Fn3 domain. In addition, the non-traditional scaffold designs allow for alternative surface interface geometries as compared to the interface geometries provided by the traditional CDR-like loop interface. The additional diversity and alternative surface geometries provided by these non-traditional binders may facilitate development of [10]Fn3 binding domains with desirable properties, for example, by providing [10]Fn3 binding domains with higher affinity for a given target, or by providing [10]Fn3 binding domains that bind to different epitopes on a given target.

The application also describes novel fibronectin based scaffold polypeptides that are associated with reduced immunogenicity. As described in the examples herein, it has been discovered the β-strand B/BC loop/β-strand C region may be an immunogenic 'hot spot' based on strong HLA binding activity. In particular, this region appears to serve as a strong anchor sequence for HLA binding. The examples also show that the wild-type sequence for the β-strand B/BC loop/β-strand C region is recognized as a self-antigen by a primate host. Therefore, despite strong HLA binding, no immune response is generated to the wild-type sequence. Accordingly, we have developed alternative [10]Fn3 scaffolds in which the key areas within the β-strand B/BC loop/β-strand C region have been left as wild-type, while modifications in other regions of the sequence permit high affinity target binding. Such alternative binders will have an increased chance of generating high affinity [10]Fn3 binding domains that avoid undesirable immune responses in a host organism because the β-strand B/BC loop/β-strand C region immunogenic hot spot is unaltered and therefore should be recognized as a self-antigen by the host organism. The application also provides alternative [10]Fn3 binding domains in which the HLA anchor sequence in the β-strand B/BC loop/β-strand C region has been destroyed, which should reduce the immunogenic potential of this region. Such [10]Fn3 binding domains with the anchor sequence removed should allow diversification of all or a portion of the BC loop, while still avoiding undesirable immune responses associated with this region. The HLA anchor sequence can be removed or destroyed by modifying key residues in the β-strand B and/or β-strand C regions, in conjunction with modifications to the BC loop region. Exemplary non-traditional [10]Fn3 binding domains having reduced immunogenic potential are described further below.

The novel fibronectin based scaffold polypeptides described herein may be designed to bind to any target of interest. In exemplary embodiments, the target is an antigen, a polypeptide or a therapeutic protein target of interest. Exemplary therapeutically desirable targets, include, for example, tumor necrosis factor alpha (TNF-alpha), delta-like protein 4 (DLL4), interleukin 17 (IL-17), and pregnane X receptor (PXR).

Fibronectin Based Scaffolds

A. General Structure

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strand s are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole"). Any or all of loops AB, BC, CD, DE, EF and FG may participate in ligand binding. There are at least 15 different Fn3 modules in human Fibronectin, and while the sequence homology between the modules is low, they all share a high similarity in tertiary structure.

In exemplary embodiments, the ligand binding scaffold proteins described herein are based on the tenth fibronectin type III domain, i.e., the tenth module of Fn3, ([10]Fn3). The amino acid sequence of a naturally occurring human [10]Fn3 is set forth in SEQ ID NO: 1:

(SEQ ID NO: 1)
VSDVPRDLEVVAATPTSLLISWDAPAVTVRYYRITYGETGGNSPVQEFTVP

GSKSTATISGLKPGVDYTITVYAVTGRGDSPASSKPISINYRTEIDKPSQ (the AB, CD and EF loops are underlined; the BC, FG, and DE loops are emphasized in bold; the β-strands are located between each of the loop regions; and the N-terminal and C-terminal regions are shown in italics). SEQ ID NO: 1 is the sequence of a [10]Fn3 molecule that comprises a tail, i.e., amino acids 95-101. SEQ ID NO: 6 is the amino acid sequence of a wild-type human [10]Fn3 molecule that does not comprise a tail and consists of amino acids 1-94 of SEQ ID NO: 1.

Residues involved in forming the hydrophobic core (the "core amino acid residues") in SEQ ID NO: 1 include the amino acids corresponding to the following amino acids of SEQ ID NO: 1 or 6: L8, V10, A13, L18, I20, W22, Y32, I34, Y36, F48, V50, A57, I59, L62, Y68, I70, V72, A74, I88, I90 and Y92, wherein the core amino acid residues are represented by the single letter amino acid code followed by the position at which they are located within SEQ ID NO: 1. See e.g., Dickinson et al., J. Mol. Biol. 236: 1079-1092 (1994). In some embodiments, the residues involved in forming the hydrophobic core are used to determine the boundaries of the loop regions of the polypeptide. For example, the AB loop may be defined as being the stretch of amino acids between the hydrophobic core residue A13 of β-strand A and the hydrophobic core residue L18 of the β-strand B. See FIG. 1. In some embodiments, the hydrophobic core amino acids are not modified relative to the wild-type sequence. In other embodiments, the following hydrophobic amino acids may be mutated: A13, which is part of a beta bulge and can convert to a surface residue; Y32 and A74, either or both of which can vary to interact differently with the nearby loops; I88, which is partially solvent-exposed and the corresponding position is not always a hydrophobic residue in natural fibronectin type III domains; and Y92, which connects to the C-terminal tail and could be diversified if the C-terminal region is diversified.

In some embodiments, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87 of SEQ ID NO: 1. The BC, DE and FG loops align along one face of the molecule, i.e. the "north pole", and the AB, CD and EF loops align along the opposite face of the molecule, i.e. the "south pole". In SEQ ID NO: 1, β-strand A corresponds to residues 8-13, β-strand B corresponds to residues 18-22, β-strand C corresponds to residues 32-36, beta strand D corresponds to residues 48-50, β-strand E corresponds to residues 57-62, β-strand F corresponds to residues 68-74, and β-strand G corresponds to residues 88-92. The β-strand s are connected to each other through the corresponding loop, e.g., strands A and B are connected via loop AB in the formation β-strand A, loop AB, β-strand B, etc. The N-terminal and/or C-terminal regions (italicized above), may be removed or altered to generate a molecule retaining biological activity and comprising the amino acid sequence of SEQ ID NO: 2 or SEQ ID NO: 6. In certain embodiments, the first 8 amino acid residues of SEQ ID NO: 1 and/or the last 7 amino acid residues of SEQ ID NO: 1 (i.e., amino acid residues 95-101 of SEQ ID NO: 1) may be removed or altered to generate a polypeptide comprising the amino acid sequence of SEQ ID NO: 60 or SEQ ID NO: 6 (corresponding to SEQ ID NO: 1 without the 7 N-terminal amino acids, and consisting of amino acids 1-94 of SEQ ID NO: 1). The libraries described herein may comprise the N- or C-terminal region set forth in SEQ ID NO: 1. In certain embodiments, the libraries comprise the N-terminal region, but do not comprise the C-terminal region (i.e., they are based on SEQ ID NO: 6).

As described above, amino acid residues corresponding to residues 14-17, 23-31, 37-47, 51-56, 63-67 and 75-87 of SEQ ID NO: 1 define the AB, BC, CD, DE, EF and FG loops, respectively. However, it should be understood that not every residue within a loop region needs to be modified in order to achieve a $^{10}$Fn3 binding domain having strong affinity for a desired target. For example, in some embodiments, only residues corresponding to amino acids 39-45 of the CD loop and 77-87 of the FG loop were modified to produce high affinity $^{10}$Fn3 binders (see e.g., the murine DLL4 binding cores having an amino acid sequence of either SEQ ID NO: 3, 4 or 5 and the murine IL-17 binding cores having an amino acid sequence of either SEQ ID NO: 45, 46 or 47).

Additionally, insertions and deletions in the loop regions may also be made while still producing high affinity $^{10}$Fn3 binding domains. For example, the CD loop of the murine DLL4 binder having SEQ ID NO: 3 has the same length CD loop as the wild-type $^{10}$Fn3 domain, i.e., the seven residues 39-45 of SEQ ID NO: 1 were replaced with the seven residues 41-47 of SEQ ID NO: 3. In contrast, the FG loop of the murine DLL4 binder having SEQ ID NO: 3 is longer in length than the corresponding FG loop of the wild-type $^{10}$Fn3 domain, i.e., the nine residues 77-85 of SEQ ID NO: 1 were replaced with the nineteen residues 79-98 of SEQ ID NO: 3.

Accordingly, in some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. To optimize antigen binding in polypeptides relying on the FG for target binding, therefore, the length of the FG loop of $^{10}$Fn3 may be altered in length as well as in sequence to obtain the greatest possible flexibility and affinity in target binding.

In some embodiments, one or more residues of the integrin-binding motif "arginine-glycine-aspartic acid" (RGD) (amino acids 78-80 of SEQ ID NO: 1 or 6) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In another embodiment, the RGD sequence is replaced with SGE. In yet another embodiment, the RGD sequence is replaced with RGE.

In some embodiments, a fibronectin based scaffold protein comprises a $^{10}$Fn3 domain having at least 40%, 50%, 55%, 60%, 65%, 70%, 75%, 80%, 85%, or 90% identity to the human $^{10}$Fn3 domain having the amino acid sequence of SEQ ID NO: 1, 2, 60 or 6. In certain embodiments, the polypeptides provided herein have at least 50% identity to the amino acid sequence of the wild-type human $^{10}$Fn3 domain (SEQ ID NO: 1, 2, 60 or 6). In other embodiments, the polypeptide has at least 65% identity to the amino acid sequence of the wild-type human $^{10}$Fn3 domain (SEQ ID NO: 1, 2, 60 or 6). In certain embodiments, one or more of the loops will not be modified relative to the sequence of the corresponding loop of the wild-type sequence and/or one or more of the β-strand s will not be modified relative to the sequence of the corresponding β-strand of the wild-type sequence. In certain embodiments, each of the beta or beta-like strands of a $^{10}$Fn3 domain in a fibronectin based scaffold protein may comprise, consist essentially of, or consist of an amino acid sequence that is at least 80%, 85%, 90%, 95% or 100% identical to the sequence of a corresponding beta or beta-like strand of SEQ ID NO: 1 or 6. Preferably, variations in the β-strand regions will not disrupt the stability of the polypeptide in physiological conditions. In exemplary embodiments, the $^{10}$Fn3 domain binds to a desired target with a $K_d$ of less than 500 nM, 100 nM, 50 nM, 1 nM, 500 pM, 100 pM or less. In some embodiments, the $^{10}$Fn3 domain of a fibronectin based protein scaffold binds to a desired target with a $K_d$ between 1 pM and 1 µM, between 100 pM and 500 nM, between 1 nM and 500 nM, or between 1 nM and 100 nM. In exemplary embodiments, the fibronectin based scaffold protein binds specifically to a target that is not bound by a wild-type $^{10}$Fn3 domain, particularly the wild-type human $^{10}$Fn3 domain.

In some embodiments, the disclosure provides polypeptides comprising a $^{10}$Fn3 domain, wherein the $^{10}$Fn3 domain comprises a loop, AB; a loop, BC; a loop, CD; a loop, DE; a loop, EF; and a loop, FG; and has at least one loop selected from loop AB, BC, CD, DE, EF and FG with an altered amino acid sequence relative to the sequence of the corresponding loop of the human $^{10}$Fn3 domain of SEQ ID NO: 1. In some embodiments, the BC, DE and FG loops are altered. In other embodiments, the CD and FG loops are altered. In other embodiments, the CD, DE and EF loops are altered. In other embodiments, the EF and FG loops are altered. In other embodiments, the AB, CD and EF loops are altered. In other embodiments, the FG loop is the only loop altered. In other embodiments, the CD and FG loops are both altered. In other embodiments, the CD and EF loops are altered. In some embodiments, one or more specific scaffold alterations are combined with one or more loop alterations. By "altered" is meant one or more amino acid sequence alterations relative to a template sequence (i.e., the corresponding wild-type human fibronectin domain) and includes amino acid additions, deletions, and substitutions.

In some embodiments, the fibronectin based scaffold protein comprises a $^{10}$Fn3 domain having an amino acid sequence at least 80, 85, 90, 95, 98, or 100% identical to the non-loop regions of SEQ ID NO: 1 or 6, wherein at least one loop selected from AB, BC, CD, DE, EF and FG is altered. For example, in certain embodiments, the AB loop may have up to 4 amino acid substitutions, up to 10 amino acid insertions, up to 3 amino acid deletions, or a combination thereof; the BC loop may have up to 10 amino acid substitutions, up to 4 amino acid deletions, up to 10 amino acid insertions, or a combination thereof; the CD loop may have up to 6 amino acid substitutions, up to 10 amino acid insertions, up to 4 amino acid deletions, or a combination thereof; the DE loop may have up to 6 amino acid substitutions, up to 4 amino acid deletions, up to 13 amino acid insertions, or a combination thereof; the EF loop may have up to 5 amino acid substations, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof.

In certain embodiments, the fibronectin based scaffold protein comprises a $^{10}$Fn3 domain that is defined generally by following the sequence:

(SEQ ID NO: 22)
VSDVPRD<u>LEVVAA</u>(X)$_u$<u>LLISW</u>(X)$_v$<u>YRITY</u>(X)$_w$<u>FTV</u>(X)$_x$<u>ATISGL</u>(X)$_y$

<u>YTITVYA</u>(X)$_z$ISINYRT

In SEQ ID NO: 22, the AB loop is represented by (X)$_u$, the BC loop is represented by (X)$_v$, the CD loop is represented by (X)$_w$, the DE loop is represented by (X)$_x$, the EF loop is represented by (X)$_y$, and the FG loop is represented by X$_z$. X represents any amino acid and the subscript following the X represents an integer of the number of amino acids. In particular, u, v, w, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 22. In some embodiments, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 22. In certain embodiments, the hydrophobic core amino acid residues (bolded residues in SEQ ID NO: 22 above) are fixed, and any substitutions, conservative substitutions, deletions or additions occur at residues other than the hydrophobic core amino acid residues. In some embodiments, the hydrophobic core residues of the polypeptides provided herein have not been modified relative to the wild-type human $^{10}$Fn3 domain (SEQ ID NO: 1).

B. Scaffold Region Modifications

The non-loop sequences of $^{10}$Fn3, i.e., the "scaffold regions", may be altered provided that the $^{10}$Fn3 domain retains target binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., Protein Eng. 2002 15(12):1015-20; Koide et al., Biochemistry 2001 40(34): 10326-33.

The scaffold regions, e.g., the β-strands and/or N- and C-termini, of $^{10}$Fn3 may be modified to increase binding of the polypeptide to a desired target or to reduce immunogenicity. In some embodiments, residues involved in forming the hydrophobic core, i.e., residues corresponding to residues L8, V10, A13, L18, I20, W22, Y32, I34, Y36, F48, V50, A57, I59, L62, Y68, I70, V72, A74, I88, I90 and Y92 of SEQ ID NO: 1 or 6 are not mutated. In some embodiments, any one of, or a combination of any one of, residues corresponding to residues 1-7, 9-15, 19, 21, 33, 35, 36, 49, 58, 60, 61, 69, 71 73, 88, 89 and 91-101 of the scaffold region of the $^{10}$Fn3 polypeptide is mutated to a different amino acid as compared to the corresponding amino acid present in the amino acid sequence set forth as SEQ ID NO: 1 or 6.

In some embodiments, mutations may be made to the scaffold regions of the polypeptides, provided that the one or more of the following specific mutations are excluded: V1A; S2P; S2T; D3G; D3S; P5S; R6G; R6S; D7G; D7K; L8P; L8Q; E9D; E9K; E9R; E9V; V10A; V10I; A12D; A12E; A12V; L18E; L18I; L18P; L18Q; L18R; L19Q; S21C; S21G; S21N; R29G; R29S; R29Y; Y31H; Y32F; R33G; I34T; I34V; T35A; T35F; T35I; Y36H; F48L; F48S; T49A; T49I; V50A; V50E; V50M; A57Deletion; T58A; T58I; T58Deletion; I59V I59Deletion; S60G; S60N; S60R; G61C; G61R; L62R; D67G; D67K; D67N; Y68A; Y68D; T69I; I70N; I70S; I70V; T71A; V72A; V72G; Y73C; Y73H; A74G; A74T; I88S; I88T; I88V; S89P; I90F; I90T; I90V; N91D; N91S; N91T; Y92C; Y92H; Y92L; Y92R; Y92Deletion; R93Q; R93T and T94A. In certain embodiments, these specific scaffold mutations are excluded in the context of a $^{10}$Fn3 domain in which the BC, DE and FG loops have been modified.

In some embodiments, mutations may be made to the scaffold regions of the polypeptides, provided that the following mutation combinations are excluded:
L18R, S21C and S60G;
E9D, L18R, V50E and T56I;

L18R, T49I and N91D;
F48S and T71A;
P5S, V10A, S60G and S89P;
L18R, and Y92C;
L18R and F48S;
L18R and V72A;
L18Q, R33G and F48S;
Y68D and Y92H;
R6S, L62R and N91S;
L8P, E9V, I34V, T71A and Y92Deletion;
E9K, L18R and F48L;
E9R, L18R, S60G and I70V;
L18R, I88V and I90T;
L18R, N91D and Y92C;
L18R and I34T;
L18R and G61C;
Y32F, T71A and T94A;
L18R, T58A, Y92L and R93T;
V50M, T58A, S89P, I90F and Y92R;
S2T, D7G, E9K, V10I, T58A, S60N and S89P;
I59V, S60N and T94A;
R6G, S21G, T35A, T58I and S60G;
L18P, S21C, T58A, Y73H and Y92C;
Y31H, R33G and G61R;
A74G, R93Q and T94A
S2P and T58I;
T58I and I88T;
T58I and I90T;
G61R and A74T
A57Deletion, T58Deletion and I59Deletion
R33G, T35I and V50M
V1A, R33G and V50M
R33G and V50M
R33G, I34V and V50M
D3G, L18I, R33G, V50M, Y73H and N91T
R6G, T35F and V72A
A12V, S21N and T35A
S21G and T49A
D3S and D7K
A12V and L19Q
A12D, L18I and L19Q
A12E, L18I and L19Q In certain embodiments, these specific combinations of scaffold mutations are excluded in the context of a $^{10}$Fn3 domain in which the BC, DE and FG loops have been modified.

In some embodiments, polypeptides having mutations at a position corresponding to position 21 of SEQ ID NO: 1 or 6 are excluded, unless a mutation at this position is combined with a mutation or mutations at any one of amino acid positions corresponding to positions 1-7, 19, 31, 49, 58, 60, 73, 75 and 89 of SEQ ID NO: 1 or 6. In some embodiments, polypeptides having mutations at a position corresponding to position 60 of SEQ ID NO: 1 are excluded unless a mutation at this position is combined with a mutation or mutations at an amino acid position corresponding to any one of positions 1-7, 9-17, 19, 21, 23-31, 33, 35, 49, 51-56, 65-67, 75-87 and 89 of SEQ ID NO: 1 or 6. In some embodiments, polypeptides having mutations at position 61 of SEQ ID NO: 1 or 6 are excluded, unless a mutation at this position is combined with a mutation or mutations at an amino acid position corresponding to any one of positions 11, 12, 19, 46, 66-67, 69 and 91 of SEQ ID NO: 1 or 6. In some embodiments, polypeptides having mutations at positions 93 or 94 of SEQ ID NO: 1 or 6 are excluded, unless a mutation at either of these positions is combined with a mutation or mutations at a position corresponding to any one of amino acid positions 1-7, 9-14, 65-67, 89 and 91 of SEQ ID NO: 1 or 6. In certain embodiments, these exclusions apply in the context of a $^{10}$Fn3 domain in which the BC, DE and FG loops have been modified.

In certain embodiments, the non-loop region of the $^{10}$Fn3 domain may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. In certain embodiments, the scaffold may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5- 10 conservative amino acid substitutions. In exemplary embodiments, the scaffold modification preferably reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In some embodiments, a $^{10}$Fn3 molecule comprises the amino acid sequence of any of the library designs set forth herein, e.g., in FIGS. 2, 9 and 12 (or amino acids 1-94 thereof; SEQ ID NO: 6) and comprises at most 1, 2, 3, 4, 5, 6, 7, 8, 9, or 10 additional substitutions, additions or deletions in a loop and/or a strand. In certain embodiments, a $^{10}$Fn3 molecule comprises the amino acid sequence of any of the library designs set forth herein, e.g., in FIGS. 2, 9 and 12 (or amino acids 1-94 thereof; SEQ ID NO: 6) with no other amino acid modifications. A $^{10}$Fn3 molecule that comprises the amino acid sequence of any of the library designs set forth herein, e.g., in FIGS. 2, 9 and 12 (or amino acids 1-94 thereof; SEQ ID NO: 6) may comprise any amino acid at a varied position, and in some instances even that of the wild-type $^{10}$Fn3 molecule. In certain embodiments, a $^{10}$Fn3 molecule that comprises the amino acid sequence of any of the library designs set forth herein, e.g., in FIGS. 2, 9 and 12 (or amino acids 1-94 thereof; SEQ ID NO: 6) comprises only non wild-type amino acids at each of the positions indicated as varied (those underlined or boxed, and bolded).

C. N- and C-Terminal Regions

In some embodiments, the amino acid sequences of the N-terminal and/or C-terminal regions of the polypeptides provided herein may be modified by deletion, substitution or insertion relative to the amino acid sequences of the corresponding regions of the wild-type human $^{10}$Fn3 domain (SEQ ID NO: 1 or 6). The $^{10}$Fn3 domains generally begin with amino acid number 1 of SEQ ID NO: 1. However, domains with amino acid deletions are also encompassed by the invention. In some embodiments, the first eight (i.e., residues 1-8) and the last seven amino acids (i.e., residues 95-101) of SEQ ID NO: 1 are deleted, generating a $^{10}$Fn3 domain having the amino acid sequence of SEQ ID NO: 60. In certain embodiments, the last seven amino acids (i.e., residues 95-101) of SEQ ID NO: 1 are deleted, generating a $^{10}$Fn3 domain having the amino acid sequence of SEQ ID NO: 6. Additional sequences may also be added to the N- or C-terminus of a $^{10}$Fn3 domain having the amino acid sequence of SEQ ID NO: 1, 2, 6, or 60. For example, in some embodiments, the N-terminal extension consists of an amino acid sequence selected from the group consisting of: M, MG, and G.

In certain embodiments, the amino acid sequence of the first 1, 2, 3, 4, 5, 6, 7, 8 or 9 residues of SEQ ID NO: 1 or 6 may be modified or deleted in the polypeptides provided herein relative to the sequence of the corresponding amino acids in the wild-type human $^{10}$Fn3 domain (SEQ ID NO: 1 or 6). In exemplary embodiments, the amino acids corresponding to amino acids 1-8 of SEQ ID NO: 1 or 6 are replaced with an alternative N-terminal region having from 1-20, 1-15, 1-10, 1-8, 1-5, 1-4, 1-3, 1-2, or 1 amino acids in length. Exemplary alternative N-terminal regions include (represented by the single letter amino acid code) M, MG, G, MGVSDVPRDL (SEQ ID NO: 9) and GVSDVPRDL (SEQ ID NO: 11), or N-terminal truncations of any one of SEQ ID NOs: 9 and 11. Other suitable alternative N-terminal regions include, for example, $X_n$SDVPRDL (SEQ ID NO: 16), $X_n$DVPRDL (SEQ ID NO: 17), $X_n$VPRDL (SEQ ID NO: 18), $X_n$PRDL (SEQ ID NO: 19), $X_n$RDL (SEQ ID NO: 20), $X_n$DL (SEQ ID NO: 21), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In other embodiments, the alternative N-terminal region comprises the amino acid sequence MASTSG (SEQ ID NO: 50).

In certain embodiments, the amino acid sequence corresponding to amino acids 93-101, 94-101, 95-101, 96-101, 97-101, 98-101, 99-101, 100-101, or 101 of SEQ ID NO: 1 are deleted or modified in the polypeptides provided herein relative to the sequence of the corresponding amino acids in the wild-type human $^{10}$Fn3 domain (SEQ ID NO: 1 or 6). In exemplary embodiments, the amino acids corresponding to amino acids 95-101 of SEQ ID NO: 1 are replaced with an alternative C-terminal region having from 1-20, 1-15, 1-10, 1-8, 1-5, 1-4, 1-3, 1-2, or 1 amino acids in length. Specific examples of alternative C-terminal region sequences include, for example, polypeptides comprising, consisting essentially of, or consisting of, EIEK (SEQ ID NO: 7), EGSGC (SEQ ID NO: 23), EIEKPCQ (SEQ ID NO: 24), EIEKPSQ (SEQ ID NO: 25), EIEKP (SEQ ID NO: 26), EIEKPS (SEQ ID NO: 27), EIEKPC (SEQ ID NO: 8), or SEQ ID NO: 44. In some embodiments, the alternative C-terminal region comprises EIDK (SEQ ID NO: 29), and in particular embodiments, the alternative C-terminal region is either EIDKPCQ (SEQ ID NO: 31) or EIDKPSQ (SEQ ID NO: 30).

In certain embodiments, the fibronectin based scaffold proteins comprise a $^{10}$Fn3 domain having both an alternative N-terminal region sequence and an alternative C-terminal region sequence.

When referring herein to molecules comprising a particular library design, which library design comprises amino acids 1-101 (SEQ ID NO: 1), it is understood that also encompassed herein are the same molecules comprising amino acids 1-94 (SEQ ID NO: 6) and not including the 7 N-terminal amino acids, and/or not including C-terminal amino acids.

D. Proteins Having Novel Loop and Scaffold Combinations

A "patch library", as described herein, refers to a library in which a region on the surface of the scaffold protein is diversified. Residues to be diversified can be determined by picking one spot on the surface of the protein, then identifying all surface and loop residues within some distance (e.g., 8 Å), and adjusting for shape, sequence connectivity, conservation, etc. For example, to generate a patch library centering on the "SouthWest" portion of the scaffold, Asp67, the last amino acid in the EF loop, which is approximately centered on the SW side was selected. All residues within an 8 Å distance of Asp67 are then identified, and the hydrophobic core residues are removed from the list of residues to be diversified, providing a total of 14 amino acids to randomize, including G37-G41, K63-D67, T69, and the C-terminal sequence beginning with N91 (residues positions numbered in accordance with the sequence of the wild-type human $^{10}$Fn3 domain having SEQ ID NO: 1 or 6). Further means of diversifications can then be incorporated into the scaffold design, for example, varying the length of the CD loop (to allow greater shape variation) or modifying or extending the sequence of the N-terminal region. Examples of possible amino acid residues to be mutated in order to generate a representative patch library are provided in FIGS. 2 and 9A-C. Three-dimensional structures of $^{10}$Fn3 domain peptides illustrating several of the different interfaces that may be targeted to generate a representative patch library are shown in FIGS. 3A-F. In some embodiments, amino acids in a $^{10}$Fn3 domain polypeptide are diversified not with regard to loop definitions, but rather with regard to their physical location on the surface of the $^{10}$Fn3 structure. In some embodiments, a 'patch' of 10 to 30 or more amino acids are diversified, chosen to form a generally contiguous surface that can span both loops and strands, or can be solely on strand residues.

1. Binders Having a North Pole and South Pole Loop Modified

In some embodiments, the polypeptides provided herein comprise a $^{10}$Fn3 domain having (i) a modification in the amino acid sequence of at least one north pole loop selected from the BC, DE and FG loops relative to the corresponding loop of the wild-type human $^{10}$Fn3 domain (SEQ ID NO: 1 or 6), and (ii) a modification in the amino acid sequence of at least one south pole loop selected from the AB, CD and EF loops relative to the corresponding loop of the wild-type human $^{10}$Fn3 domain (SEQ ID NO: 1 or 6). The modified north pole and south pole loops contribute to binding to the same target. Various combinations of modified north pole and south pole loops are contemplated. For example, a $^{10}$Fn3 may comprise one modified north pole loop and one modified south pole, one modified north pole loop and two modified south pole loops, two modified north pole loops and one modified south pole loop, two modified north pole loops and two modified south pole loops, three modified north pole loops and one modified south pool loop, etc., wherein each of the modified loops contributes to binding to the same target. Exemplary combinations of north pole and south pole loops that may be modified include, for example, the CD loop (south pole) and the FG loop (north pole), the CD loop (south pole) and the DE loop (north pole), the EF loop (south pole) and FG loop (north pole), the AB loop (south pole) and the FG loop (north pole), or the DE loop (north pole) and the EF loop (south pole). Another exemplary loop combination is the CD loop (south pole), the DE loop (north pole) and the EF loop (south pole). Yet another exemplary loop combination is the DE loop (north pole) and one of more of the AB, CD and EF loops (south pole). The modified loops may have sequence modifications across an entire loop or only in a portion of the loop. Additionally, one or more of the modified loops may have insertions or deletions such that the length of the loop is varied relative to the length of the corresponding loop of the wild-type sequence. In certain embodiments, additional regions in the $^{10}$Fn3 domain (i.e., in addition to the north and south pole loops), such as β-strand, N-terminal and/or C-terminal regions, may also be modified in sequence relative to the wild-type $^{10}$Fn3 domain, and such additional modifications may also contribute to binding to the target.

Exemplary $^{10}$Fn3 designs having at least one north pole loop and at least one south pole loop modified include, for example, the WS1, WS2, WS3, WS2', Front1, Front2, Back1, Back2, WS-LI1, SouthFront, and AG Strand designs shown in FIG. 9A and the West Side, South Front and AG Strand designs shown in FIG. 2 ("West Side Binder," "South-Front Binder," and "AG Strand Binder," respectively).

2. Binders Having Loop and Scaffold Region Modifications

Also provided herein are $^{10}$Fn3 domains having novel combinations of loop and scaffold modifications. In particular, the application provides polypeptides comprising a $^{10}$Fn3 domain comprising (i) a modification in the amino acid sequence of at least one of loops AB, BC, CD, DE, EF, or FG, and (ii) a modification in the amino acid sequence of at least one scaffold region (i.e., a modification in at least one β-strand, the N-terminal region, and/or the C-terminal region), wherein the modified loop(s) and modified scaffold region(s) both contribute to binding the same target. In exemplary embodiments, the scaffold region modifications are located adjacent to modifications in a loop region, e.g., if the AB loop is modified, scaffold mutations may tend to be located in β-strand A and/or β-strand B, which are adjacent to the AB loop in the linear sequence of the $^{10}$Fn3 domain. In other embodiments, a cluster of modifications may be found together in loop and scaffold regions that are adjacent to one another in the linear sequence of the $^{10}$Fn3 domain. For example, $^{10}$Fn3 binders having both loop and scaffold modifications, may have clusters of amino acid modifications in the following combinations of loop and scaffold regions that are adjacent to each other in the linear sequence of the $^{10}$Fn3 domain: β-strand/loop/β-strand, loop/ strand/loop, loop/strand/loop/strand, terminal region/ strand/loop, or loop/strand/terminal region, etc. For example, $^{10}$Fn3 domains having novel combinations of loop and scaffold modifications may have clusters of modifications such that over a stretch of 20 contiguous amino acids at least 15 of the amino acids are modified relative to wild-type. In other embodiments, at least 17 out of 20, 18 out of 20, 17 out of 25, 20 out of 25, or 25 out of 30 residues in a contiguous stretch are modified relative to the wild-type $^{10}$Fn3 domain sequence over the corresponding stretch of amino acids. In certain embodiments, a given $^{10}$Fn3 domain may have two or three clusters of modifications separated by stretches of unmodified (i.e., wild-type) sequence. For any given region (i.e., a loop, β-strand or terminal region) that is modified, all or only a portion of the region may be modified relative to the wild-type sequence. When a β-strand region is modified, preferably the hydrophobic core residues remain unmodified (i.e., wild-type) and one or more of the non-core residues in the β-strand are modified. Suitable modifications in the loop, β-strand or terminal regions include amino acid substitutions, deletion and/or insertions, as well as combinations thereof.

Exemplary $^{10}$Fn3 designs having at least one loop region and at least one scaffold region modified include, for example, the WS1, Front1, Front2, Back1, Back2, SP1, SP2, SP3, SouthFront, AG Strand and SouthWest designs shown in FIG. 9A, the NW3 design shown in FIG. 9B, the NP1, NE1, NP4-5, NP6-1 and NW2 designs shown in FIG. 9C, and the designs shown in FIG. 2.

3. "West-Side" Binders

In some embodiments, the application provides $^{10}$Fn3 domains having a binding face along the "west-side" of the molecule (See FIG. 3C) and are referred to as "West-side binders" or "WS binders". WS binders as described herein comprise a $^{10}$Fn3 domain that has a modified CD loop and a modified FG loop, as compared to the corresponding CD and FG loop sequences set forth in SEQ ID NO: 1 or 6. The CD loop and the FG loop both contribute to binding to the same target. In certain embodiments, the WS binders may comprise additional modifications at one or more regions within the $^{10}$Fn3 domain. For example, WS binders may comprise scaffold modifications in one or more of the β-strand regions adjacent to the CD and/or FG loops. In particular, WS binders may comprise sequence modifications in one or more of β-strand C, β-strand D, β-strand F, and/or β-strand G. Exemplary scaffold modifications include modifications at one or more scaffold region positions corresponding to the amino acid positions: 33, 35, 49, 69, 71, 73, 89 and/or 91 of SEQ ID NO: 1 or 6. The WS binders may also comprise modifications in the BC loop, particularly in the C-terminal portion of the BC loop. In one embodiment, the last two residues of the BC loop (i.e., corresponding to amino acids 30 and 31 in the wild-type $^{10}$Fn3 domain) are modified relative to the wild-type sequence. All or a portion of the additional loop and scaffold modifications may contribute to binding to the target in conjunction with the modified CD and FG loops. Preferably, the hydrophobic core residues are not modified relative to the wild-type sequence.

In certain embodiments, a WS binder has a CD loop that is about 3-11, 4-9 or 5 residues long; an FG loop that is about 1-10, e.g., 6 or 5, residues long; a C strand that is about 6-14, 8-11, or 9 residues long; and/or an F strand that is about 9-11 or 10 residues long. Positions 31, 33, 35 and 37-39 of the beta strand C may be altered relative to the wild-type sequence. Positions 32, 34 and 36 of the beta strand C may be hydrophobic residues. Positions 67, 69, 71 and 73 of the beta strand F may be altered relative to the wild-type sequence. Positions 68, 70, and 72 of the beta strand F may be hydrophobic residues. A WS binder may comprise amino acid substitutions at positions 30, 31, 32, 33, 34, 35, 36, 37, 38 and/or 39, such as positions 31, 33, 35, 37, 38 and/or 39, e.g., positions 31 and/or 33, of SEQ ID NO: 1 or 6. A WS binder may comprise amino acid substitutions at positions 44, 45, 46, 47, 48, 49, 50 and/or 51, such as positions 44, 45, 47 and/or 49, of SEQ ID NO: 1 or 6. A WS binder may comprise amino acid substitutions at positions 40, 41, 42, 43, 44 and/or 45 of SEQ ID NO: 1 or 6. A WS binder may comprise amino acid substitutions at positions 67, 68, 69, 70, 71, 72, 73, 74, 75 and/or 76, such as positions 67, 69, 71, 73 and/or 76 or positions 71, 73, 75 and/or 76, of SEQ ID NO: 1 or 6. A WS binder may comprise amino acid substitutions at positions 76, 77, 78, 79, 81, 82, 83, 84, 85 and/or 86, such as positions 84 and/or 85 of SEQ ID NO: 1 or 6. A WS binder may comprise amino acid substitutions at positions 85, 86, 87, 88, 89, 90, 91, 92, 93 and/or 94 of SEQ ID NO: 1 or 6. A WS binder may comprise amino acid substitutions at positions 31, 33, 47, 49, 73 and/or 75 of SEQ ID NO: 1 or 6. A WS binder may comprise a loop C comprising from 4-9 varied, e.g., non wild-type amino acids; an FG loop comprising from 5-6 varied, e.g., non wild-type amino acids; and wherein amino acids 31, 33, 35, 37-39, 67, 69, 71, 73 and 76 are not wild-type. "Not wild-type" amino acids are amino acids that are not those found at the same position in the wild-type human $^{10}$Fn3 molecule (having, e.g., SEQ ID NO: 1 or 6).

Exemplary $^{10}$Fn3 WS binder designs include, for example, the WS1, WS2, WS3, WS2', and WS-LI1 designs shown in FIG. 9A and the "West Side Binder" design shown in FIG. 2 (or amino acids 1-94 thereof). When referring to a $^{10}$Fn3 molecule having a particular design based on a $^{10}$Fn3 sequence comprising amino acids 1-101, the description is intended to encompass those molecules that do not comprise "DK" at the end terminus and/or that do not comprise the N-terminal 7 amino acids, and correspond to amino acids 1-94 of the sequence shown. Alternatively, when the design shown comprises amino acids 1-94, the description is intended to encompass the same design with the N-terminal 7 amino acids, which may devoid of the sequence "DK." Other modifications that may be made are described herein.

Exemplary WS binder designs are provided in FIG. 12. WS3, for example corresponds to WS1, wherein the length of the loops CD and FG may be modified, and D67 may also be modified. An example of a molecule having a WS3 design is PXR binder having SEQ ID NO: 49. Variants of WS1, WS2, WS3, WS2', WS-LI1, and WS4 include those having a wild-type or mutated amino acid at positions 30, 31, 33, 35, 37, 38, 46, 47, 49, 50, 67, 69, 71, 73, 75, 76, 84, 85, 86, 87, 89 or 91. For example, a WS binder design may comprise one or more amino acid modifications in amino acids 39-45 of the CD loop and one or more amino acid modification in amino acids 77-83 in loop FG (WS-LI1 design), and wherein a $^{10}$Fn3 molecule having that design binds specifically to a target molecule (and optionally does not comprise an RGD sequence). A WS binder design may comprise the design of WS-LI1 and at most 1, 2, 3, 4, 5, 6, 7, 8, 9, 10, 12, 15, 17, 20 or 25 additional amino acid modifications in the loops or strands. For example, a WS binder design may comprise the design of WS-LI1 and at most 1, 2, 3, 4, 5, 6, 7, 8, 9, 10, 12, 15, 17, 20 or 25 additional amino acid modifications at amino acid positions such as at amino acid positions 37, 38, 46, 47, 75, 76, and 85-88. Other amino acid modifications that may be included are those at positions 30, 31, 33, 35, 49, 50, 67, 69, 71, 73, 89 and 91. An exemplary WS design may comprise the amino acid sequence of WS7 (FIG. 12), wherein the loops may vary in length from those in the wild-type $^{10}$Fn3 molecule, and wherein each varied position (bolded and underlined) may be modified to any other amino acid, or in certain instances, may be kept unmodified, provided that a $^{10}$Fn3 molecule with such a design binds specifically to a target molecule (and optionally does not comprise an RGD site). In certain embodiments, a $^{10}$Fn3 molecule comprises the amino acid sequence of WS7, wherein the length of loops CD and FG may be varied, wherein no other amino acid may be varied, and wherein exactly or at most 0, 1, 2, 3, 4, 5, 6, 7, 8, 9, 10, 12, 15, 17, 20 or 25 amino acid residues that are indicated as variable (those underlined and bolded) are actually not changed, and are the amino acids corresponding to those at the same position in the wild-type human $^{10}$Fn3 molecule, i.e., wild-type amino acids (SEQ ID NO: 1 or 6). For example, one or more of amino acids 30, 31, 33, 35, 36, 37, 47, 49, 50, 67, 69, 71, 73, 75 and 87 in WS7 may be the wild-type amino acid, provided that the WS binder binds specifically to its target. In certain embodiments, a WS binder having a WS7 design does not comprise any amino acid modification other than those indicated. In certain embodiments, a WS binder having a WS7 design comprises at most 1, 2, 3, 4, 5, 6, 7, 8, 9, 10, 12, 15, 17, 20 or 25 amino acid modifications in addition to those indicated.

Also provided are libraries comprising any one of the WS binder designs described herein. An exemplary library is a library comprising WS binders having a varied CD and FG loop and further comprising non wild-type amino acids at positions 30, 31, 33, 47 and 49. An exemplary library is a library having a varied FG loop and further comprising non wild-type amino acids at positions 30, 31, 33, 47 and 49.

In certain embodiments, at least or at most 10, 20, 30, 40, 50, or 60 amino acids of a design sequence is not varied, e.g., is not varied by substitution. For example, one or more of the following amino acids are retained as the amino acid from the wild-type human $^{10}$Fn3 molecule: amino acids at positions 1-29, 32, 34, 36, 48, 51-66, 68, 70, 72, 88, 90 and 92-101.

Examples of WS binders that bind specifically to therapeutic targets are described in the Examples, and include for example polypeptides having the amino acid sequence of any one of SEQ ID NOs: 3-5, 45-49, 62-63, 66, and 72.

In some embodiments, a WS binder comprises the amino acid sequence of WS1, WS2, WS3, WS2', WS-LI1, WS4, WS5, WS6 or WS7 (or amino acids 1-94 thereof) and comprises at most 1, 2, 3, 4, 5, 6, 7, 8, 9 or 10 additional substitutions, additions or deletions in a loop and/or a strand. In certain embodiments, a WS binder comprises the amino acid sequence of WS1, WS2, WS3, WS2', WS-LI1, WS4, WS5, WS6 or WS7 (or amino acids 1-94 thereof) with no other amino acid modifications. A WS binder that comprises the amino acid sequence of WS1, WS2, WS3, WS2', WS-LI1, WS4, WS5, WS6 or WS7 (or amino acids 1-94 thereof) may comprise any amino acid at a varied position, and in some instances even that of the wild-type $^{10}$Fn3 molecule. In certain embodiments, a WS binder that comprises the amino acid sequence of WS1, WS2, WS3, WS2', WS-LI1, WS4, WS5, WS6 or WS7 (or amino acids 1-94 thereof) comprises non wild-type amino acids at each of the positions indicated as varied (those underlined and bolded).

4. "Front" Binders

In some embodiments, the polypeptides provided herein comprise a $^{10}$Fn3 domain having modifications in the CD, DE and, in some cases, EF loops, wherein the loop modifications all contribute to target binding. These polypeptides are referred to as "front binders" herein. The front binders may additionally comprise modifications in one or more scaffold regions, particularly in scaffold regions that flank or are adjacent to a modified loop region. For example, the front binders may comprise a scaffold modification in one or more of β-strand C, β-strand D, and/or β-strand E relative to the sequences of the corresponding β-strands of the wild-type human $^{10}$Fn3 domain (SEQ ID NO: 1 or 6). Preferably the hydrophobic core residues are not modified relative to the wild-type sequence. Exemplary scaffold modifications that may be present in front binders, include modifications at one or more positions corresponding to amino acid positions 36, 49, 58 and/or 60 of SEQ ID NO: 1 or 6. Such scaffold modifications may contribute to binding to the target together with the modified loops. In certain embodiments, the front binders may comprise clusters of modifications spanning several loop and strand regions of the $^{10}$Fn3 domain. In particular, the front binders may comprise modifications in at least 15, 20, 24, 25, or 27 of the 31 residues between the amino acids corresponding to residues 36 through 66 of the wild type human $^{10}$Fn3 domain (SEQ ID NO: 1 or 6). The loop and/or strand modifications may include amino acid substitutions, deletions and/or insertions, or combinations thereof. In exemplary embodiments, the CD loop is extended in length or reduced in length relative to the CD loop of the wild-type human $^{10}$Fn3 domain (SEQ ID NO: 1 or 6). Exemplary $^{10}$Fn3 front binder designs include, for example, the Front1 and Front2 designs shown in FIG. 9A.

5. "Back" Binders

In some embodiments, the polypeptides provided herein comprise a $^{10}$Fn3 domain having modifications in the EF and FG loops, wherein the loop modifications contribute to binding the same target. These polypeptides are referred to as "back binders" herein. The back binders may comprise additional modifications in other loop and/or scaffold regions. For example, a back binder may contain modifications in at least a portion of the AB loop, preferably the N-terminal portion of the AB loop. In an exemplary embodiment, the first two amino acids of the AB loop (i.e., corresponding to amino acid residues 14 and 15 of the wild-type $^{10}$Fn3 domain) are modified relative to the wild-type sequence. In certain embodiments, a back binder may also contain one or more scaffold modifications, particularly modifications in one or more scaffold regions that are adjacent to a modified loop region. For example, back binders may contain one or more modifications in one or more of β-strand A, β-strand G, the N-terminal region, and/or the C-terminal region. Preferably the hydrophobic core residues are not modified relative to the wild-type sequence. Exemplary scaffold modifications include modifications at one or more positions corresponding to amino acid positions 1-7, 9-13, 89, 91, 93 and/or 94 of SEQ ID NO: 1 or 6. One or more of the additional loop and/or scaffold modifications may contribute to binding to the target along with the modified EF and FG loops. Suitable loop and/or scaffold region modifications include amino acid substitutions, deletions and/or insertions, or combinations thereof. In certain embodiments, the amino acid sequence of the FG loop is extended in length or reduced in length relative to the FG loop of the wild type human $^{10}$Fn3 domain (SEQ ID NO: 1 or 6).

In certain embodiments, a back binder may comprise a cluster of modified amino acid residues over a contiguous span of several regions in the $^{10}$Fn3 domain. For example, at least 14 of the first 15 amino acid residues of the $^{10}$Fn3 domain may be modified relative to the corresponding residues in the wild-type human $^{10}$Fn3 domain (SEQ ID NO: 1 or 6), and/or at least 15 of the 18 residues between the amino acids corresponding to residues 80 through 97 (or 94) of the wild type human $^{10}$Fn3 domain (SEQ ID NO: 1 or 6) may be modified relative to the corresponding residues in the wild-type sequence.

Exemplary $^{10}$Fn3 back binder designs include, for example, the Back1 and Back2 designs shown in FIG. 9A.

6. "South Pole" Binders

In certain embodiments, the application provides polypeptides comprising a $^{10}$Fn3 domain, wherein the $^{10}$Fn3 domain comprises modifications in the amino acid sequences of β-strand A, loop AB, β-strand B, loop CD, β-strand E, loop EF, and β-strand F, relative to the sequences of the corresponding regions of the wild-type sequence. These polypeptides are referred to as "south pole binders" or "SP binders" herein. The modified loops and strands contribute to binding to the same target. The amino acid sequence of the CD loop may be extended in length or reduced in length relative to the CD loop of the wild type human $^{10}$Fn3 domain (SEQ ID NO: 1 or 6). The south pole binders may comprise additional modifications in β-strand G and/or the C-terminal region relative to the sequence of the corresponding region of the wild-type sequence. In exemplary embodiments, the south pole binders may comprise one or more modifications at amino acids corresponding to positions 11, 12, 19, 60, 61, 69, 91, 93 and 95-97 of the wild-type sequence. Exemplary $^{10}$Fn3 south pole binder designs include, for example, the SP1, SP2 and SP3 designs shown in FIG. 9A.

7. "Northwest" Binders

In some embodiments, the application provides polypeptides comprising a $^{10}$Fn3 domain having modified BC, DE and FG loops, as compared to the corresponding BC, DE and FG loop sequences set forth in SEQ ID NO: 1 or 6, as well as additional modifications in one or more of β-strand C, β-strand D, β-strand F and β-strand G strand residues. The β-strand and loop region modifications together contribute to binding to the target. These proteins are referred to as "Northwest binders", or "NW binders", herein. In exemplary embodiments, the NW binders comprise one or more scaffold modifications at any one of, or combination of, amino acid positions corresponding to scaffold region positions R33, T49, Y73 and S89 of SEQ ID NO: 1 or 6. Suitable modifications in loop and scaffold regions include amino acid substations, deletions and/or insertions, or combinations thereof. In certain embodiments, one or more of the BC, DE and FG loops are extended in length or reduced in length, or combinations thereof, relative to the wild-type sequence. In one embodiment, each of the BC, DE and FG loops are extended in length or reduced in length, or combinations thereof, relative to the wild-type sequence (e.g., SEQ ID NO: 1 or 6). In certain embodiments, only a portion of the BC loop is modified, particularly the C-terminal portion, relative to the wild-type sequence. For example, the BC loop may be modified only at amino acid residues corresponding to amino acids 27-31 of the wild-type BC loop, whereas the rest of the BC loop (i.e., corresponding to residues 23-26 of the wild-type loop) are left unmodified.

Figure 3C:
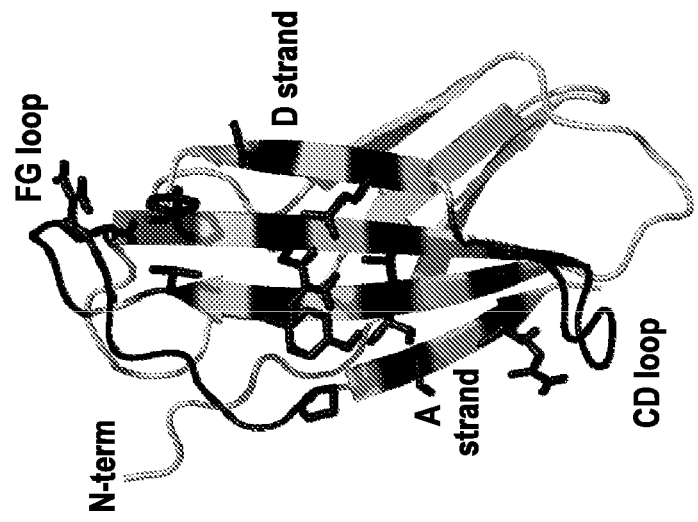
Figure 3B:
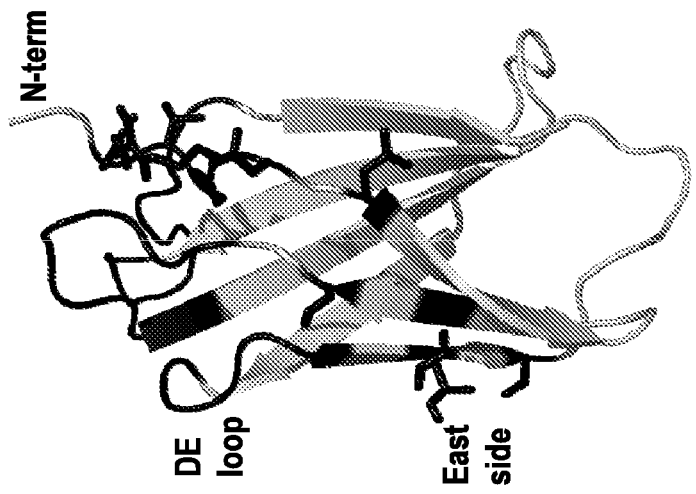
Figure 3A:
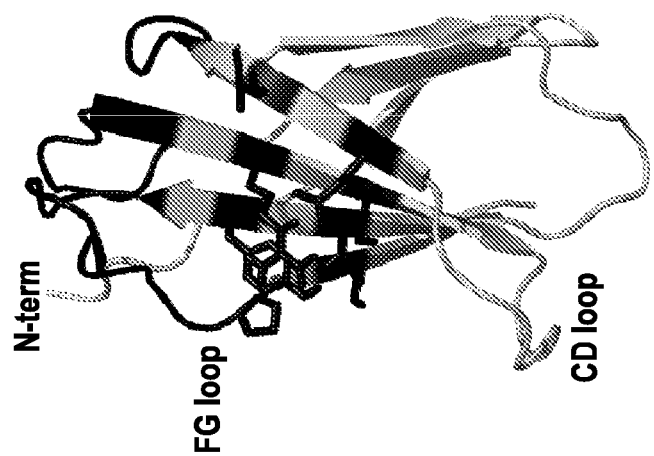

Exemplary $^{10}$Fn3 NW binder designs include, for example, the NW3 design shown in FIG. 9B, the NW2 design shown in FIG. 9C, and the "NorthWest Binder" design shown in FIG. 2. A model of the NW binder is depicted in FIG. 3A.

8. "Northeast" Binders

In some embodiments, the application provides polypeptides comprising a $^{10}$Fn3 domain having a modified BC, DE and FG loop as well as one or more additional modifications in any one of, or combination of, the N-terminal region, β-strand A, β-strand B and/or β-strand E. These proteins are referred to as "Northeast binders", or "NE binders", herein. In exemplary embodiments, the NE binders are modified at any one of, or combination of, amino acids corresponding to scaffold region positions 1-7, E9, L19, S21 and/or T58 of the wild-type sequence (SEQ ID NO: 1 or 6). The combination of modified loop and scaffold regions contributes to binding to the target. Exemplary $^{10}$Fn3 NE binder designs include, for example, the NE1 design shown in FIG. 9C and the "NorthEast Binder" design shown in FIG. 2. A model of the NE binder is depicted in FIG. 3B.

9. "South Front" Binders

In some embodiments, the application provides polypeptides comprising a $^{10}$Fn3 domain having modifications in one or more of the AB, CD, DE and EF loops, as well as additional modifications in one or more of β-strand B, β-strand D and/or β-strand E. These proteins are referred to as "South Front binders" herein. The combination of modified loop and strand residues contributes to binding to the target. In exemplary embodiments, a South Front binder may be modified at one or more amino acid positions corresponding to scaffold region positions L19, T49, T58, S60, and/or G61 of SEQ ID NO: 1 or 6 and/or at one or more amino acid positions corresponding to loop region positions T14-S17, P51, T56, G40-E47, and/or K63-G65 of SEQ ID NO: 1 or 6. In exemplary embodiments, a South Front binder may be extended in length or reduced in length in the AB loop, between amino acids corresponding to residues 18 and 20 of the wild-type sequence, and/or in the CD loop. Exemplary $^{10}$Fn3 South Front binder designs include, for example, the SouthFront design shown in FIG. 9A and the "South-Front Binder" design shown in FIG. 2. A model of the South Front binder is depicted in FIG. 3D.

10. "AG" Binders

In some embodiments, the application provides polypeptides comprising a $^{10}$Fn3 domain having a modified β-strand A and β-strand G, as compared to the corresponding strand of SEQ ID NO: 1 or 6. These proteins are referred to as "AG Binders" or "AG Strand" binders herein. In certain embodiments, the AG strand binders comprise clusters of modifications at the N-terminal and C-terminal portions of the $^{10}$Fn3 domain, whereas the middle portion of the $^{10}$Fn3 remains unmodified. For example, an AG strand binder may comprise modifications at 16 out of 19 of the first 19 amino acids in the $^{10}$Fn3 domain (i.e., corresponding to amino acid positions 1-19 of SEQ ID NO: 1 or 6) and modifications at 13-17 out of 18 of the last 18 amino acids in the $^{10}$Fn3 domain (i.e., corresponding to amino acid positions 84-101 of SEQ ID NO: 1) or at 14-18 out of 22 of the last 22 amino acids in the $^{10}$Fn3 domain (i.e., corresponding to amino acid positions 80-101 of SEQ ID NO: 1). In exemplary embodiments, an AG binder may comprise modifications at one or more positions corresponding to positions 1-7, 9, 11-17, 19, 84-89 and 91-97 of SEQ ID NO: 1. Preferably the modified regions in an AG binder contribute to binding to the same target. Exemplary $^{10}$Fn3 AG binder designs include, for example, the AG Strand design shown in FIG. 9A and the "AG Strand Binder" design shown in FIG. 2. A model of the AG binder is depicted in FIG. 3E.

11. "Southwest" Binders

In some embodiments, the application provides polypeptides comprising a $^{10}$Fn3 domain having a modified CD and EF loop, as well as additional modifications in any one of, or combination of residues corresponding to positions 69 or 91-97 of SEQ ID NO: 1. These proteins are referred to as "Southwest binders", or "SW binders", herein. The modified loop and scaffold regions contribute to binding to the target. Exemplary $^{10}$Fn3 SW binder designs include, for example, the SouthWest design shown in FIG. 9A and the "SouthWest Binder" design shown in FIG. 2. A model of the SW binder is depicted in FIG. 3F.

E. Proteins Having Reduced Immunogenicity

In some embodiments, the polypeptides provided herein are associated with reduced immunogenicity. As described in the examples, the region around the BC loop of a $^{10}$Fn3 domain appears to be an immunogenic hot spot. Accordingly, the application provides two types of $^{10}$Fn3 designs having reduced immunogenicity. In the first type of design, the BC loop is left entirely or at least partially unmodified such that the host (e.g., human) immune response is more likely to recognize the BC region of the $^{10}$Fn3 domain as self thereby avoiding an immune response. In the second type of design, the strong HLA binding anchor in the BC region of the $^{10}$Fn3 domain is removed or destroyed such that the BC region should not bind as tightly to the host HLA receptors thereby decreasing the immunogenic potential of the BC region of the $^{10}$Fn3 binders. These $^{10}$Fn3 designs are described further below.

In certain embodiments, the application provides polypeptides having reduced immunogenicity comprising a $^{10}$Fn3 domain wherein the entire BC loop is left as wild-type. Preferably such polypeptides have lower immunogenicity relative to an equivalent polypeptide with modifications in the BC loop. Polypeptides with wild-type BC loops have modifications in other regions of the $^{10}$Fn3 domain that are involved in target binding. Preferably, the modifications outside of the BC loop do not lead to a strong immune response to the $^{10}$Fn3 domain in the host. Examples of $^{10}$Fn3 binders where the entire BC loop is left as wild-type include, for example, the WS binders, Front binders, Back binders, South Pole binders, South Front binders, AG binders and Southwest binders as described herein. Particular examples of $^{10}$Fn3 designs having the BC loop unmodified relative to the wild-type sequence, include, for example, the WS2, WS3, Front1, Front2, Back1, Back2, SP1, SP2, SP3, LI-3 (a), WS-LI1, LU-S9, SouthFront, AG Strand and SouthWest designs shown in FIG. 9A and the designs shown in FIG. 2. In $^{10}$Fn3 binder designs having a wild-type BC loop, it may be desirable to leave all or a portion of β-strand B and/or β-strand C unmodified relative to the wild-type sequence as well, particularly the portions of β-strand B and/or β-strand C that are adjacent to the BC loop (i.e., the C-terminal portion of β-strand B and/or the N-terminal portion of β-strand C). In exemplary embodiments, $^{10}$Fn3 domains having a wild-type BC loop and reduced immunogenicity may not have any modifications in the portion of the $^{10}$Fn3 domain that is N-terminal to the CD loop, i.e., the N-terminal region, β-strand A, AB loop, β-strand B, BC loop and β-strand C are all left unmodified relative to the wild-type sequence.

In certain embodiments, the application provides polypeptides having reduced immunogenicity comprising a $^{10}$Fn3 domains wherein a portion of the BC loop is left as wild-type. Preferably such polypeptides have lower immunogenicity relative to an equivalent polypeptide with modifications in a greater portion of the BC loop. In exemplary embodiments, the N-terminal portion of the BC loop is left as wild-type. For example, the first 1, 2, 3, 4, 5, or 6 residues of the BC loop may be left as wild-type, while the remaining C-terminal residues of the BC loop can be modified. In $^{10}$Fn3 designs having at least a portion of the N-terminal region of the BC loop as wild-type, it may be desirable to leave all or a portion of β-strand B and/or β-strand C unmodified relative to the wild-type sequence as well, particularly the portions of β-strand B and/or β-strand C that are adjacent to the BC loop (i.e., the C-terminal portion of β-strand B and/or the N-terminal portion of β-strand C). In exemplary embodiments, $^{10}$Fn3 domains having the wild-type sequence in an N-terminal portion of the BC loop and reduced immunogenicity may not have any modifications in the N-terminal region, β-strand A, AB loop, and β-strand B. In $^{10}$Fn3 designs with a portion of the BC loop as wild-type, the modified portion of the BC loop may contribute to target binding along with modifications in other regions of the $^{10}$Fn3 domain. Examples of $^{10}$Fn3 binders where an N-terminal portion of the BC loop is left as wild-type include, for example, the $^{10}$Fn3 designs shown in FIG. 9B, the WS1 design shown in FIG. 9A, and the $^{10}$Fn3 design ("West Side Binder") shown in FIG. 2.

In certain embodiments, the application provides polypeptides having reduced immunogenicity comprising $^{10}$Fn3 domains, wherein the strong HLA anchor in the region of β-strand B/BC loop/β-strand C (the "BC anchor") has been removed or destroyed (e.g., modified relative to the wild type sequence in a manner that reduces binding affinity to one or more HLA receptors). For example, the BC anchor may be removed or destroyed by modifying the $^{10}$Fn3 domain at one or more positions corresponding to positions L19, S21, R33 and/or T35 of SEQ ID NO:1 or 6. When the BC anchor has been removed or destroyed, it is possible to modify the sequence of the BC loop without significantly increasing the immunogenic potential of the BC region. Accordingly, many such $^{10}$Fn3 designs have modifications in the BC loop in addition to the modifications in β-strand B and/or β-strand C. The BC loop may contribute to target binding, optionally in combination with modifications in other regions of the $^{10}$Fn3 domain. The modifications in β-strand B and/or β-strand C may or may not contribute to target binding. Examples of $^{10}$Fn3 binders where the BC anchor has been removed or destroyed include, for example, the $^{10}$Fn3 designs shown in FIG. 9C and the $^{10}$Fn3 design ("NorthEast Binder") shown in FIG. 2.

In certain embodiments, the polypeptides described herein have reduced immunogenicity as compared to a polypeptide having SEQ ID NO: 61, e.g., the immunogenicity of the polypeptide is lower than the immunogenicity of a polypeptide having SEQ ID NO: 61.

The immunogenicity of a polypeptide described herein may be assessed, for example, by one or more of the following methods: Human Leukocyte Antigen ("HLA") binding, in silico prediction of HLA binding (for example, with the Epimatrix program), in vitro activation of human T-cells, in vivo animal immune response, or other methods for evaluating immunogenicity potential.

In certain embodiments, immunogenicity may be assessed by HLA binding experiments. Preferably the polypeptides provided herein bind to one or more HLA receptors with an $IC_{50}$ that is less than or equal to the $IC_{50}$ associated with binding between an equivalent HLA receptor(s) and a wild-type $^{10}$Fn3 domain. For example, the polypeptides provided herein may bind to an HLA receptor with an $IC_{50}$ of greater than 10 μM, 15 μM, 20 μM, 25 μM, 50 μM, 100 μM, 150 μM or 200 μM. In some embodiments, the polypeptides may bind to an HLA receptor with an $IC_{50}$ between 10 μM and 1 mM, between 100 μM and 1 mM or between 500 μM and 1 mM. The HLA allele used for assessing the polypeptide/HLA $IC_{50}$ binding may be one or more of DRB*0101, DRB*0301, DRB*0401, DRB*0701 and/or DRB*1501.

In some embodiments, immunogenicity may be assessed by in silico analysis, such as EpiMatrix. In particular embodiments, the polypeptides provided herein are associated with an EpiMatrix "Z" scale score less than or equal to the score associated with a wild-type $^{10}$Fn3 domain. In certain embodiments, the polypeptides provided herein are associated with an EpiMatrix "Z" scale score that is no greater than 200% of the score associated with a wild-type $^{10}$Fn3 domain. In some embodiments, the polypeptides are associated with an EpiMatrix score less than 1.64 on the EpiMatrix "Z" scale (An Z; 2009; Therapeutic Monoclonal Antibodies: From Bench to Clinic; John Wiley and Sons; New Jersey; pages 428-429).

In some embodiments, immunogenicity may be assessed by in vivo animal immune response experiments. For example, an animal, e.g. mouse or monkey, may be injected with the polypeptides provided herein and the IgG and/or IgM immune response measured. Preferably, the polypeptides described herein display an IgG or IgM immune response that is no more than 200%, 100%, 50%, 40%, 30%, 25%, 20%, 15%, 10%, 5%, 2% or 1% greater than the IgG or IgM immune response observed in a mouse or monkey injected with a wild-type $^{10}$Fn3 domain.

The application also provides libraries of the polypeptides provided herein and methods of selecting binders to a desired target from the libraries. There will be a higher likelihood of isolating a target binding molecule with acceptable immunogenicity characteristics from the libraries provided herein, relative to libraries that have not been designed to avoid the immunogenic potential associated with the BC region. These libraries are useful for reducing the amount of effort necessary to deimmunize polypeptide candidates, and to increase the probability of identifying non-immunogenic polypeptide molecules.

F. Multivalent Proteins

In certain embodiments, the fibronectin based scaffold protein is a multivalent protein that comprises two or more $^{10}$Fn3 domains. For example, a multivalent fibronectin based scaffold protein may comprise 2, 3 or more $^{10}$Fn3 domains that are covalently associated. In exemplary embodiments, the fibronectin based scaffold protein is a bispecific or dimeric protein comprising two $^{10}$Fn3 domains. In certain embodiments, a multivalent fibronectin based protein scaffold comprises a first $^{10}$Fn3 domain that binds to a first target molecule and a second $^{10}$Fn3 domain that binds to a second target molecule. The first and second target molecules may be the same or different target molecules. When the first and second target molecules are the same, the first and second $^{10}$Fn3 domains may bind to the same target but at different epitopes. Additionally, when the first and second target molecules are the same, the regions of modification in the $^{10}$Fn3 domain that are associated with target binding may be the same or different. Furthermore, the first and second $^{10}$Fn3 domains may be based on the same or different scaffold designs. For example, a multivalent fibronectin based protein scaffold may comprise two $^{10}$Fn3 domains, wherein both $^{10}$Fn3 are based on the same non-traditional scaffold design described herein, wherein one of the $^{10}$Fn3 domains is based on a first type of non-traditional scaffold design and the second $^{10}$Fn3 domain is based on a second type of non-traditional scaffold design, or one of the ¹⁰Fn3 domains is based on a non-traditional scaffold design and the second is based on a traditional scaffold design (i.e., the BC, DE and FG loops are modified).

In exemplary embodiments, each $^{10}$Fn3 domain of a multivalent fibronectin based protein scaffold binds to a desired target with a $K_d$ of less than 500 nM, 100 nM, 50 nM, 1 nM, 500 pM, 100 pM or less. In some embodiments, each $^{10}$Fn3 domain of a multivalent fibronectin based protein scaffold binds to a desired target with a $K_d$ between 1 pM and 1 μM, between 100 pM and 500 nM, between 1 nM and 500 nM, or between 1 nM and 100 nM. In exemplary embodiments, each $^{10}$Fn3 domain of a multivalent fibronectin based protein scaffold binds specifically to a target that is not bound by a wild-type $^{10}$Fn3 domain, particularly the wild-type human $^{10}$Fn3 domain.

The $^{10}$Fn3 domains in a multivalent fibronectin based scaffold protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as linkers having the amino acid sequence of SEQ ID NO: 32. In some embodiments, the linker is a glycine-serine based linker. These linkers comprise glycine and serine residues and may be between 8 and 50, 10 and 30, and 10 and 20 amino acids in length. Examples of such linkers include SEQ ID NOs: 39-43. In some embodiments, the linker is a glycine-proline based linker. These linkers comprise glycine and proline residues and may be between 3 and 30, 10 and 30, and 3 and 20 amino acids in length. Examples of such linkers include SEQ ID NOs: 33-35. In some embodiments, the linker is a proline-alanine based linker. These linkers comprise proline and alanine residues and may be between 3 and 30, 10 and 30, 3 and 20 and 6 and 18 amino acids in length. Examples of such linkers include SEQ ID NOs: 36-38. In exemplary embodiments, the linker does not contain any Asp-Lys (DK) pairs.

Pharmacokinetic Moieties

In one aspect, the application provides for fibronectin based scaffold proteins further comprising a pharmacokinetic (PK) moiety. Pharmokinetics encompasses properties of a compound including, by way of example, absorption, distribution, metabolism, and elimination by a subject. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein shortly after administration and shortly before the next administration). The fibronectin based scaffold proteins may be attached to a moiety that reduces the clearance rate of the polypeptide in a mammal (e.g., mouse, rat, or human) by greater than three-fold relative to the unmodified polypeptide. Other measures of improved pharmacokinetics may include serum half-life, which is often divided into an alpha phase and a beta phase. Either or both phases may be improved significantly by addition of an appropriate moiety. A PK moiety refers to any protein, peptide, or moiety that affects the pharmacokinetic properties of a biologically active molecule when fused to the biologically active molecule.

PK moieties that tend to slow clearance of a protein from the blood include polyoxyalkylene moieties, e.g., polyethylene glycol, sugars (e.g., sialic acid), and well-tolerated protein moieties (e.g., Fc, Fc fragments, transferrin, or serum albumin). The fibronectin based scaffold proteins may be fused to albumin or a fragment (portion) or variant of albumin as described in U.S. Publication No. 20070048282. In some embodiments, the PK moiety is a serum albumin binding protein such as those described in U.S. Publication Nos. 2007/0178082 and 2007/0269422. In some embodiments, the PK moiety is a serum immunoglobulin binding protein such as those described in U.S. Publication No. 2007/0178082.

In some embodiments, the fibronectin based scaffold proteins may be attached to a PK moiety comprising a nonproteinaceous polymer. In some embodiments, the polymer is polyethylene glycol ("PEG"), polypropylene glycol, or polyoxyalkylenes, as described in U.S. Pat. No. 4,640,835; 4,496,689; 4,301,144; 4,670,417; 4,791,192 or 4,179,337. In exemplary embodiments, the polymer is a PEG moiety.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, *J. Biol. Chem.*, 252, 3571 (1977) and *J. Biol. Chem.*, 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22). It is noted that a fibronectin based scaffold protein containing a PEG molecule is also known as a conjugated protein, whereas the protein lacking an attached PEG molecule can be referred to as unconjugated.

The size of PEG utilized will depend on several factors including the intended use of the fibronectin based scaffold protein. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging applications, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to fibronectin based scaffold proteins. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to the fibronectin based scaffold protein. In some embodiments, the PEG moiety is about 20, 30, 40, 50, 60, 70, 80, or 90 KDa. In some embodiments, the PEG moiety is about 40 KDa.

In some embodiments, PEGylated fibronectin based scaffold proteins contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in a pegylated fibronectin based scaffold protein is from about 3,000 Da to 60,000 Da, or from about 10,000 Da to 36,000 Da. In a one embodiment, the PEG in a pegylated fibronectin based scaffold protein is a substantially linear, straight-chain PEG.

One skilled in the art can select a suitable molecular mass for PEG, e.g., based on how the pegylated fibronectin based scaffold protein will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In some embodiments, a fibronectin based scaffold protein is covalently linked to one poly(ethylene glycol) group of the formula: —CO—(CH$_2$)$_x$—(OCH$_2$CH$_2$)$_m$—OR, with the —CO (i.e. carbonyl) of the poly(ethylene glycol) group forming an amide bond with one of the amino groups of the binding polypeptide; R being lower alkyl; x being 2 or 3; m being from about 450 to about 950; and n and m being chosen so that the molecular weight of the conjugate minus the binding polypeptide is from about 10 to 40 kDa. In one embodiment, a fibronectin based scaffold protein's ε-amino group of a lysine is the available (free) amino group.

In one specific embodiment, carbonate esters of PEG are used to form the PEG-fibronectin based scaffold protein conjugates. N,N'-disuccinimidylcarbonate (DSC) may be used in the reaction with PEG to form active mixed PEG-succinimidyl carbonate that may be subsequently reacted with a nucleophilic group of a linker or an amino group of a fibronectin based scaffold protein (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382,657), respectively.

Pegylation of a fibronectin based scaffold protein can be performed according to the methods of the state of the art, for example by reaction of the fibronectin based scaffold protein with electrophilically active PEGs (supplier: Shearwater Corp., USA, world wide web at shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., Bioconjugate Chem. 6 (1995) 62-69). Such methods may used to pegylate at an ε-amino group of a lysine of a fibronectin based scaffold protein or at the N-terminal amino group of the fibronectin based scaffold protein.

In another embodiment, PEG molecules may be coupled to sulfhydryl groups on a fibronectin based scaffold protein (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610,281 and 5,766,897 describes exemplary reactive PEG species that may be coupled to sulfhydryl groups.

In some embodiments, the pegylated fibronectin based scaffold protein is produced by site-directed pegylation, particularly by conjugation of PEG to a cysteine moiety. In certain embodiments, the Cys residue may be positioned at the N-terminus, between the N-terminus and the most N-terminal beta or beta-like strand, at the C-terminus, or between the C-terminus and the most C-terminal beta or beta-like strand of the fibronectin based scaffold protein. A Cys residue may be situated at other positions as well, particularly any of the loops that do not participate in target binding or between two binding domains of a multivalent fibronectin based scaffold protein. A PEG moiety may also be attached by other chemistry, including by conjugation to amines.

In some embodiments where PEG molecules are conjugated to cysteine residues on a fibronectin based scaffold protein, the cysteine residues are native to the fibronectin based scaffold protein, whereas in other embodiments, one or more cysteine residues are engineered into the fibronectin based scaffold protein. Mutations may be introduced into a fibronectin based scaffold protein coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of fibronectin based scaffold proteins, given that the crystal structure of the tenth fn3 domain framework based on which fibronectin based scaffold proteins are designed has been solved (see Dickinson, et al., J. Mol. Biol. 236(4): 1079-92 (1994)) and thus the surface-exposed residues identified. In one embodiment, cysteine residues are introduced into fibronectin based scaffold protein at or near the N- and/or C-terminus, or within loop regions. Pegylation of cysteine residues may be carried out using, for example, PEG-maleimide, PEG-vinylsulfone, PEG-iodoacetamide, or PEG-orthopyridyl disulfide.

In some embodiments, the pegylated fibronectin based scaffold protein comprises a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254, 12579, and in Chamow et al., (1994) Bioconjugate Chem. 5, 133.

In another embodiment, pegylated fibronectin based scaffold proteins comprise one or more PEG molecules covalently attached to a linker, which in turn is attached to the alpha amino group of the amino acid residue at the N-terminus of the fibronectin based scaffold protein. Such an approach is disclosed in U.S. Publication No. 2002/0044921 and PCT Publication No. WO94/01451.

In one embodiment, a fibronectin based scaffold protein is pegylated at the C-terminus. In a specific embodiment, a protein is pegylated at the C-terminus by the introduction of C-terminal azido-methionine and the subsequent conjugation of a methyl-PEG-triarylphosphine compound via the Staudinger reaction. This C-terminal conjugation method is described in Cazalis et al., C-Terminal Site-Specific PEGylation of a Truncated Thrombomodulin Mutant with Retention of Full Bioactivity, *Bioconjug Chem.* 2004; 15(5):1005-1009.

In exemplary embodiments, a fibronectin based scaffold protein is pegylated in a C-terminal tail region as described further herein. In exemplary embodiments, the C-terminal contains a Cys residue, which is used as the site of attachment for the PEG moiety. Exemplary C-terminal tails include, for example, a polypeptide having any one of SEQ ID NOs: 23, 24 or 31.

Conventional separation and purification techniques known in the art can be used to purify PEGylated fibronectin based scaffold proteins, such as size exclusion (e.g., gel filtration) and ion exchange chromatography. Products may also be separated using SDS-PAGE. Products that may be separated include mono-, di-, tri- poly- and un-pegylated fibronectin based scaffold proteins, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired. In an embodiment of this invention the percentage of mono-PEG conjugates is from ninety percent to ninety-six percent.

In one embodiment of the invention, the PEG in a pegylated fibronectin based scaffold protein is not hydrolyzed from the pegylated amino acid residue using a hydroxylamine assay, e.g., 450 mM hydroxylamine (pH 6.5) over 8 to 16 hours at room temperature, and is thus stable. In one embodiment, greater than 80% of the composition is stable mono-PEG-fibronectin based scaffold protein, more preferably at least 90%, and most preferably at least 95%.

In another embodiment, the pegylated fibronectin based scaffold proteins will preferably retain at least about 25%, 50%, 60%, 70%, 80%, 85%, 90%, 95% or 100% of the biological activity associated with the unmodified protein. In one embodiment, biological activity refers to its ability to bind to one or more target molecules, as assessed by $K_d$, $k_{on}$ or $k_{off}$. In one specific embodiment, the pegylated fibronectin based scaffold protein shows an increase in binding to one or more target molecules relative to unpegylated fibronectin based scaffold protein.

The serum clearance rate of PEG-modified fibronectin based scaffold proteins may be decreased by about 10%, 20%, 30%, 40%, 50%, 60%, 70%, 80%, or even 90%, relative to the clearance rate of the unmodified fibronectin based scaffold protein. The PEG-modified fibronectin based scaffold protein may have a half-life ($t_{1/2}$) which is enhanced relative to the half-life of the unmodified fibronectin based scaffold protein. The half-life of PEG-modified fibronectin based scaffold protein may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified fibronectin based scaffold protein. In some embodiments, the protein half-life is determined in vitro, such as in a buffered saline solution or in serum. In other embodiments, the protein half-life is an in vivo half life, such as the half-life of the fibronectin based scaffold protein in the serum or other bodily fluid of an animal.

Nucleic Acid-Protein Fusion Technology

In one aspect, the application provides fibronectin based scaffold proteins comprising a fibronectin type III domain that bind a human target, such as, for example, TNF-alpha, DLL4, IL-17, PXR or other proteins. One way to rapidly make and test Fn3 domains with specific binding properties is the nucleic acid-protein fusion technology of Adnexus, a Bristol-Myers Squibb Company. Such in vitro expression and tagging technology, termed PROfusion™, that exploits nucleic acid-protein fusions (RNA- and DNA-protein fusions) may be used to identify novel polypeptides and amino acid motifs that are important for binding to proteins. Nucleic acid-protein fusion technology is a technology that covalently couples a protein to its encoding genetic information. For a detailed description of the RNA-protein fusion technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO00/34784; WO01/64942; WO02/032925; and Roberts and Szostak, Proc Natl. Acad. Sci. 94:12297-12302, 1997, herein incorporated by reference.

Vectors & Polynucleotides Embodiments

Nucleic acids encoding any of the various fibronectin based scaffold proteins disclosed herein may be synthesized chemically, enzymatically or recombinantly. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 Jan. 21; 100(2):438-42; Sinclair et al. Protein Expr Purif. 2002 October; 26(1):96-105; Connell N D. Curr Opin Biotechnol. 2001 October; 12(5):446-9; Makrides et al. Microbiol Rev. 1996 September; 60(3):512-38; and Sharp et al. Yeast. 1991 October; 7(7):657-78.

General techniques for nucleic acid manipulation are described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The fibronectin based scaffold proteins described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2 micron plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

Expression and cloning vectors usually contain a promoter that is recognized by the host organism and is operably linked to the nucleic acid encoding the fibronectin-based scaffold protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the fibronectin based scaffold protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human .beta.-interferon cDNA in mouse cells under the control of a thymidine kinase promoter from herpes simplex virus. Alternatively, the rous sarcoma virus long terminal repeat can be used as the promoter.

Transcription of a DNA encoding fibronectin based scaffold proteins by higher eukaryotes is often increased by inserting an enhancer sequence into the vector. Many enhancer sequences are now known from mammalian genes (globin, elastase, albumin, .alpha.-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. One useful transcription termination component is the bovine growth hormone polyadenylation region. See WO94/11026 and the expression vector disclosed therein.

The recombinant DNA can also include any type of protein tag sequence that may be useful for purifying the fibronectin based scaffold protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, E. coli or Bacillus spp. Yeast, preferably from the Saccharomyces species, such as S. cerevisiae, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified fibronectin based scaffold proteins are prepared by culturing suitable host/vector systems to express the recombinant proteins. For many applications, the small size of the fibronectin based scaffold proteins would make expression in E. coli the preferred method for expression. The fibronectin based scaffold protein is then purified from culture media or cell extracts.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the fibronectin based scaffold proteins may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO90/03430; WO87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Fibronectin based scaffold proteins disclosed herein can also be produced using cell-free translation systems. For such purposes the nucleic acids encoding the fibronectin based scaffold protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Fibronectin based scaffold proteins can also be produced by chemical synthesis (e.g., by the methods described in Solid Phase Peptide Synthesis, 2nd ed., 1984, The Pierce Chemical Co., Rockford, Ill.). Modifications to the fibronectin based scaffold protein can also be produced by chemical synthesis.

The fibronectin based scaffold proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, fibronectin based scaffold proteins may be exchanged into different buffers and/or concentrated by any of a variety of methods known to the art, including, but not limited to, filtration and dialysis.

The purified fibronectin based scaffold protein is preferably at least 85% pure, more preferably at least 95% pure, and most preferably at least 98% pure. Regardless of the exact numerical value of the purity, the fibronectin based scaffold protein is sufficiently pure for use as a pharmaceutical product.

Exemplary Uses

In one aspect, the application provides fibronectin based scaffold proteins labeled with a detectable moiety. The fibronectin based scaffold proteins may be used for a variety of diagnostic applications. The detectable moiety can be any one which is capable of producing, either directly or indirectly, a detectable signal. For example, the detectable moiety may be a radioisotope, such as H3, C14, C13, P32, S35, or I131; a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). In vitro methods, include conjugation chemistry well know in the art including chemistry compatible with proteins, such as chemistry for specific amino acids, such as Cys and Lys. In order to link a detectable moiety to a fibronectin based scaffold protein, a linking group or reactive group is used. Suitable linking groups are well known in the art and include disulfide groups, thioether groups, acid labile groups, photolabile groups, peptidase labile groups and esterase labile groups. Preferred linking groups are disulfide groups and thioether groups depending on the application. For polypeptides without a Cys amino acid, a Cys can be engineered in a location to allow for activity of the protein to exist while creating a location for conjugation.

Fibronectin based scaffold proteins linked with a detectable moiety are useful for in vitro or in vivo imaging. The polypeptide may be linked to a radio-opaque agent or radioisotope, administered to a subject, preferably into the bloodstream, and the presence and location of the labeled protein in the subject may be assayed. This imaging technique is useful, for example, in the staging and treatment of malignancies when the fibronectin based scaffold protein binds to a target associated with cancer. The fibronectin based scaffold protein may be labeled with any moiety that is detectable in a subject, whether by nuclear magnetic resonance, radiology, or other detection means known in the art.

Fibronectin based scaffold proteins also are useful as affinity purification agents. In this process, the fibronectin based scaffold proteins are immobilized on a suitable support, such as Sephadex resin or filter paper, using methods well known in the art.

Fibronectin based scaffold proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

In certain aspects, the disclosure provides methods for detecting a target molecule in a sample. A method may comprise contacting the sample with a fibronectin based scaffold protein described herein, wherein said contacting is carried out under conditions that allow fibronectin based scaffold protein-target complex formation; and detecting said complex, thereby detecting said target in said sample. Detection may be carried out using any technique known in the art, such as, for example, radiography, immunological assay, fluorescence detection, mass spectroscopy, or surface plasmon resonance. The sample will often by a biological sample, such as a biopsy, and particularly a biopsy of a tumor, or a suspected tumor, where the fibronectin based scaffold protein binds to a target associated with cancer. The sample may be from a human or other mammal. The fibronectin based scaffold protein may be labeled with a labeling moiety, such as a radioactive moiety, a fluorescent moiety, a chromogenic moiety, a chemiluminescent moiety, or a hapten moiety. The fibronectin based scaffold protein may be immobilized on a solid support.

In one aspect, the application provides fibronectin based scaffold proteins useful in the treatment of disorders. The diseases or disorders that may be treated will be dictated by the binding specificity of the fibronectin based scaffold protein. As described herein, fibronectin based scaffold proteins may be designed to bind to any target of interest. Exemplary targets include, for example, TNF-alpha, DLL4, IL-17 and PXR. Merely as an example, fibronectin based scaffold proteins that bind to TNF-alpha may be used to treat autoimmune disorders such as rheumatoid arthritis, inflammatory bowel disease, psoriasis, and asthma; fibronectin based scaffold proteins that bind to IL-17 may be used to treat asthma; and fibronectin based scaffold proteins that bind to DLL4 may be used to treat hyperproliferative disorders or diseases associated with unwanted angiogenesis, such as cancers or tumors.

The application also provides methods for administering fibronectin based scaffold proteins to a subject. In some embodiments, the subject is a human. In some embodiments, the fibronectin based scaffold proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions comprising $^{10}$Fn3 domains that lack the integrin-binding domain (RGD) and compositions that are essentially endotoxin or pyrogen free or have very low endotoxin or pyrogen levels.

Formulation and Administration

The application further provides pharmaceutically acceptable compositions comprising the fibronectin based scaffold proteins described herein, wherein the composition is essentially endotoxin and/or pyrogen free.

Therapeutic formulations comprising fibronectin based scaffold proteins are prepared for storage by mixing the described proteins having the desired degree of purity with optional physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulations herein may also contain more than one active compounds as necessary for the particular indication being treated, preferably those with complementary activities that do not adversely affect each other. Such molecules are suitably present in combination in amounts that are effective for the purpose intended.

The fibronectin based scaffold proteins may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the fibronectin based scaffold proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each fibronectin based scaffold protein will be dependent on the identity of the protein, the preferred dosages can range from about 10 mg/square meter to about 2000 mg/square meter, more preferably from about 50 mg/square meter to about 1000 mg/square meter.

For therapeutic applications, the fibronectin based scaffold proteins are administered to a subject, in a pharmaceutically acceptable dosage form. They can be administered intravenously as a bolus or by continuous infusion over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of fibronectin based scaffold proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the fibronectin based scaffold protein typically will be formulated at a concentration of about 0.1 mg/ml to 100 mg/ml, although wide variation outside of these ranges is permitted. For the treatment of disease, the appropriate dosage of fibronectin based scaffold proteins will depend on the type of disease to be treated, the severity and course of the disease, whether the fibronectin based scaffold proteins are administered for preventive or therapeutic purposes, the course of previous therapy, the patient's clinical history and response to the fibronectin based scaffold protein, and the discretion of the attending physician. The fibronectin based scaffold protein is suitably administered to the patient at one time or over a series of treatments.

Fibronectin based scaffold proteins may also be used as crystallization chaperones to generate structures of a protein with a compound of interest. For example, a fibronectin based scaffold protein that specifically binds to human pregnane X receptor (PXR) may be used as a crystallization chaperone to facilitate crystallization of a compound with PXR, e.g., the ligand binding domain (LBD) of PXR. Several $^{10}$Fn3 molecules that bind to human PXR are described herein.

PXR activation upregulates cellular levels of several drug metabolizing enzymes such as cytochrome P450 enzymes and MDR1. The increased expression of CYP enzymes can alter the pharmacokinetics of drug and lead to dangerous drug-drug interactions including loss of therapeutic efficacy and increased toxicity. To avoid late stage clinical failures and high costs associated with bringing a new drug to market, many pharmaceutical companies have adopted screening assays for early detection of compounds that activate PXR. Additionally in silico screening using known crystal structures of PXR are increasingly being used to predict potential PXR activity. The large and flexible ligand binding pocket of PXR and the potential of these compounds to bind to different locations and in multiple orientations within the ligand binding cavity of PXR complicates reliable prediction of PXR activity. This is especially true for more advanced compounds/chemotypes with desirable efficacy, selectivity and bioavailability towards the intended therapeutic target but with known PXR liability. Given these limitations, a co-crystal structure is often required to define exact binding interactions and to suggest specific modifications that can disturb crucial interactions related to PXR binding while maintaining activity against the primary target. For example, in certain embodiments, a method for analyzing the interaction of a test agent with PXR comprises incubating together (i) PXR, or a ligand binding domain thereof; (ii) the test agent and (iii) a ¹⁰Fn3 protein specifically binding to PXR, e.g., PXR LBD, under conditions suitable for crystallization. Exemplary ¹⁰Fn3 proteins specifically binding to PXR LBD comprise an amino acid sequence that is at least 70%, 80%, 90%, 95%, 97%, 98% or 99% identical to one of SEQ ID NOs: 48, 49 and 62-69 and 72. In certain embodiments, ¹⁰Fn3 proteins specifically binding to PXR LBD comprise an amino acid sequence that differs from any one of SEQ ID NOs: 48, 49 and 62-69 and 72 in at most 1, 2, 3, 5, 10, 15, 20 or 25 amino acid changes, e.g., substitutions (such as conservative substitutions), additions or deletions. The method may further comprise inducing crystallization and determining which portions (or atoms) of the test agent interacts with PXR (generally the ligand binding domain of PXR), and optionally modifying the test agent such that it no longer interacts with PXR or does so with lower affinity.

SEQUENCES

Wild-Type ¹⁰Fn3 Sequences:

WT ¹⁰Fn3 Domain
(SEQ ID NO: 1)
VSDVPRDLEVVAATPTSLLISWDAPAVTVRYYRITYGETGGNSPVQEFTVP

GSKSTATISGLKPGVDYTITVYAVTGRGDSPASSKPISINYRTEIDKPSQ

WT ¹⁰Fn3 Domain Core Sequence version 1
(SEQ ID NO: 2)
LEVVAATPTSLLISWDAPAVTVRYYRITYGETGGNSPVQEFTVPGSKSTAT

ISGLKPGVDYTITVYAVTGRGDSPASSKPISINY

WT ¹⁰Fn3 Domain with D80E Substitution
(SEQ ID NO: 59)
VSDVPRDLEVVAATPTSLLISWDAPAVTVRYYRITYGETGGNSPVQEFTVP

GSKSTATISGLKPGVDYTITVYAVTGRGESPASSKPISINYRTEIDKPSQ

WT ¹⁰Fn3 Domain Core Sequence version 2
(SEQ ID NO: 60)
EVVAATPTSLLISWDAPAVTVRYYRITYGETGGNSPVQEFTVPGSKSTATI

SGLKPGVDYTITVYAVTGRGDSPASSKPISINYRT

WT ¹⁰Fn3 Domain Core Sequence version 3
(SEQ ID NO: 22)
VSDVPRDLEVVAA(X)ᵤLLISW(X)ᵥYRITY(X)ᵥFTV(X)ₓATISGL(X)ᵧ

YTITVYA(X)ᵤISINYRT

WT ¹⁰Fn3 Domain Core Sequence version 4
(SEQ ID NO: 6)
VSDVPRDLEVVAATPTSLLISWDAPAVTVRYYRITYGETGGNSPVQEFTVP

GSKSTATISGLKPGVDYTITVYAVTGRGDSPASSKPISINYRT

DLL4 Binding WS-LI1 Binders:

(SEQ ID NO: 3)
MGVSDVPRDLEVVAATPTSLLISWDAPAVTVRYYRITYGEQHSKYPHQEFT

VPGSKSTATISGLKPGVDYTITVYAVTIQPQDPEQDYQYHYYETSSKPISI

NYRTEIDKPSQ (SEQ ID NO: 4)
MGVSDVPRDLEVVAATPTSLLISWDAPAVTVRYYRITYGEHVADHFDHNQE

FTVPGSKSTATISGLKPGVDYTITVYAVTYQFQDPEEHYYYHFYDSSSKPI

SINYRTEIDKPSQ (SEQ ID NO: 5)
MGVSDVPRDLEVVAATPTSLLISWDAPAVTVRYYRITYGEYHEHYHSPGFS

QKYHYEQEFTVPGSKSTATISGLKPGVDYTITVYAVTGHKHYHYYYYYHHH

SSKPISINYRTEIDKPSQ

Exemplary N-Terminal Extension Sequences:

(SEQ ID NO: 9)
MGVSDVPRDL (SEQ ID NO: 10)
VSDVPRDL (SEQ ID NO: 11)
GVSDVPRDL (SEQ ID NO: 16)
XₙSDVPRDL, wherein n = 0, 1 or 2 amino acids, wherein when n = 1, X is Met or Gly, and when n = 2, X is Met-Gly (SEQ ID NO: 17)
XₙDVPRDL, wherein n = 0, 1 or 2 amino acids, wherein when n = 1, X is Met or Gly, and when n = 2, X is Met-Gly (SEQ ID NO: 18)
XₙVPRDL, wherein n = 0, 1 or 2 amino acids, wherein when n = 1, X is Met or Gly, and when n = 2, X is Met-Gly (SEQ ID NO: 19)
XₙPRDL, wherein n = 0, 1 or 2 amino acids, wherein when n = 1, X is Met or Gly, and when n = 2, X is Met-Gly (SEQ ID NO: 20)
XₙRDL, wherein n = 0, 1 or 2 amino acids, wherein when n = 1, X is Met or Gly, and when n = 2, X is Met-Gly (SEQ ID NO: 21)
XₙDL, wherein n = 0, 1 or 2 amino acids, wherein when n = 1, X is Met or Gly, and when n = 2, X is Met-Gly (SEQ ID NO: 50)
MASTSG Exemplary C-Terminal Tail Sequences:

(SEQ ID NO: 7)
EIEK (SEQ ID NO: 8)
EIEKPC (SEQ ID NO: 23)
EGSGC (SEQ ID NO: 24)
EIEKPCQ (SEQ ID NO: 25)
EIEKPSQ (SEQ ID NO: 26)
EIEKP

|  | (SEQ ID NO: 27) |
|---|---|
| EIEKPS | |
| EGSGS | (SEQ ID NO: 28) |
| EIDK | (SEQ ID NO: 29) |
| EIDKPSQ | (SEQ ID NO: 30) |
| EIDKPCQ | (SEQ ID NO: 31) |

Exemplary Linker Sequences:

|  | (SEQ ID NO: 32) |
|---|---|
| PSTSTST | |
| GPG | (SEQ ID NO: 33) |
| GPGPGPG | (SEQ ID NO: 34) |
| GPGPGPGPG | (SEQ ID NO: 35) |
| PAPAPA | (SEQ ID NO: 36) |
| PAPAPAPAPA | (SEQ ID NO: 37) |
| PAPAPAPAPAPAPAPA | (SEQ ID NO: 38) |
| GSGSGSGSGS | (SEQ ID NO: 39) |
| GSGSGSGSGSGSGSGSGS | (SEQ ID NO: 40) |
| GGGGSGGGGSGGGGS | (SEQ ID NO: 41) |
| GGGGSGGGGSGGGGSGGGGSGGGGS | (SEQ ID NO: 42) |
| GGGGSGGGGSGGGSG | (SEQ ID NO: 43) |

6×His Tag:

|  | (SEQ ID NO: 44) |
|---|---|
| HHHHHH | |

IL-17 Binding WS-LI1 Binders:

(SEQ ID NO: 45)
MGVSDVPRDLEVVAATPTSLLISWDAPAVTVRYYRITYGE<u>YHAFFASNGKY</u>
<u>YFYI</u>QEFTVPGSKSTATISGLKPGVDYTITVYAVT<u>DDTVHHGDSNYHSSKP</u>
<u>ISINY</u>RTEIDKPSQ (SEQ ID NO: 46)
MGVSDVPRDLEVVAATPTSLLISWDAPAVTVRYYRITYGE<u>YSSFFQHQGQY</u>
<u>YHYI</u>QEFTVPGSKSTATISGLKPGVDYTITVYAVT<u>QHEHSQDSSKPISINY</u>
RTEIDKPSQ (SEQ ID NO: 47)
MGVSDVPRDLEVVAATPTSLLISWDAPAVTVRYYRITYGE<u>FSQFVHSDGEY</u>
<u>YQEY</u>QEFTVPGSKSTATISGLKPGVDYTITVYAVT<u>GQYDQDDEP</u>SSKPISI
NYRTEIDKPSQ

PXR Binding WS1 Binders:

(SEQ ID NO: 48)
MASTSGVSDVPRDLEVVAATPTSLLISWDAPAV<u>PVSKYVI</u>YWPGALISSM
QAF<u>K</u>VPGSKSTATISGLKPGV<u>LYSIVVDA</u>LTGDGQGSYVWDPI<u>TI</u>TYRTEG
SGS (SEQ ID NO: 49)
MASTSGVSDVPRDLEVVAATPTSLLISWDAPAVTV<u>HSYYIT</u>YQELQHHSVP
QGF<u>QV</u>PGSKSTATISGLKPGV<u>AYQIAVYAF</u>TGPGLPPSDAPPI<u>VI</u>YYRTEG
SGS

¹⁰Fn3 Loop and Scaffold Region Peptides from FIG. 4:

|  | (SEQ ID NO: 58) |
|---|---|
| PTSLLISWDAPAVTVRYYRITYG | |
| PVQEFTVPGSKSTATISGLK | (SEQ ID NO: 51) |
| TITVYAVTGRGDSPASSKPISINYRT | (SEQ ID NO: 52) |
| MGEVVAATPTSLLIS | (SEQ ID NO: 53) |
| PHFPTRYYRITYGETGGNS | (SEQ ID NO: 54) |

BC Loop Sequences from Example 2:

|  | (SEQ ID NO: 55) |
|---|---|
| PTSLLISWDAPAVTVRYYRITYG | |
| PTSLLISWSARLKVARYYRITYG | (SEQ ID NO: 56) |
| PTSLLISWRHPHFPTRYYRITYG | (SEQ ID NO: 57) |

IGF-1R Binding ¹⁰Fn3 Domain With Modified BC, DE and FG Loops:

(SEQ ID NO: 61)
GVSDVPRDLEVVAATPTSLLISWSARLKVARYYRITYGETGGNSPVQEFTV
PKNVYTATISGLKPGVDYTITVYAVTRFRDYQPISINYRTEIDKPSQ

PXR Binding ¹⁰Fn3 Molecules:
The amino acid sequences of Adnectins 1-8 of FIG. 10 correspond to SEQ ID NOs: 70, 71, 62, 63, 72, 13, 14 and 15, respectively. Amino acid sequences of Adnectins 1-8 of FIG. 10 without the 6×His tail (SEQ ID NO: 44) correspond to SEQ ID NOs: 64, 65, 48, 49, 66, 67, 68 and 69, respectively.

EXAMPLES

The invention is now described by reference to the following examples, which are illustrative only, and are not intended to limit the present invention. While the invention has been described in detail and with reference to specific embodiments thereof, it will be apparent to one of skill in the art that various changes and modifications can be made thereto without departing from the spirit and scope thereof.

Example 1. Expression and Purification of Fibronectin Based Scaffold Proteins Selected binders were cloned into a PET9d vector and transformed into *E. coli* BL21 DE3 plysS cells. Transformed cells were inoculated in 5 ml LB medium containing 50 µg/mL kanamycin and 34 µg/ml chloromphenicol in a 24-well format and grown at 37° C. overnight (inoculums culture). Production cultures were established by aspirating 2000 of the inoculum culture into 5 ml (in a 24-well format) of TB-Overnight Expression Media (auto induction) containing 50 µg/ml Kanamycin and 34 µg/ml chloromphenicol. The cultures were grown at 37° C. for 4 hours at which time the temperature was lowered to 18° C. and grown for 20 hours. Cultures were harvested by centrifugation for 10 minutes at 2750 g at 4° C.

Cell pellets (in 24-well format) were lysed by resuspension in 450 µl of Lysis buffer (50 mM $NaH_2PO_4$, 0.5 M NaCl, 1× Complete™ Protease Inhibitor Cocktail-EDTA free (Roche), 1 mM PMSF, 10 mM CHAPS, 40 mM Imidazole, 1 mg/ml lysozyme, 30 µg/ml DNAse, 2 µg/ml aprotonin, pH 8.0) and shaken at room temperature for 1-3 hours. Lysates were clarified and re-racked into a 96-well format by transfer into a 96-well Whatman GF/D Unifilter fitted with a 96-well, 1.2 ml catch plate and filtered by positive pressure. The clarified lysates were transferred to a 96-well HisPur Cobalt Plate that had been equilibrated with equilibration buffer (50 mM $NaH_2PO_4$, 0.5 M NaCl, 40 mM Imidazole, pH 8.0) and were incubated for 5 min. Unbound material was removed by positive pressure. The resin was washed 2×0.3 ml/well with Wash buffer #1 (50 mM $NaH_2PO_4$, 0.5 M NaCl, 5 mM CHAPS, 40 mM Imidazole, pH 8.0) with each wash removed by positive pressure. Prior to elution each well was washed with 50 µl Elution buffer (PBS+20 mM EDTA), incubated for 5 min and this wash was discarded by positive pressure. Protein was eluted by applying an additional 100 µl of Elution buffer to each well. After a 30 minute incubation at room temperature the plate(s) were centrifuged for 5 minutes at 200 g and eluted protein was collected in 96-well catch plates containing 5 µl of 0.5M $MgCl_2$ added to the bottom of elution catch plate prior to elution. Eluted protein was quantified using a total protein assay with SGE as the protein standard. SGE is a wild-type $^{10}Fn3$ domain in which the RGD sequence in the FG loop is changed to SGE.

Example 2. Characterization of the Immunogenicity of $^{10}Fn3$ Domain Polypeptides The adaptive immune response is initiated by the processing and digestion of an internalized protein by an antigen-presenting cell (APC), such as a dendritic cell. The APC clips the internalized protein into short peptides and then displays the peptides on its surface MHC Class II molecules. The peptide binding site of the MHC Class II molecule is long and narrow, like a hot-dog bun, and holds its peptide in an extended format, with room for nine amino acids in the primary binding site (and generally allows for short tails on either side of the peptide). Certain pockets in the MHC binding site are dominant in determining peptide binding. These pockets correspond to amino acid positions 1, 4, 6, and 9 in the anchored portion of the 9-mer peptide. A peptide that has favorable side chains at each of these four positions will in general bind to HLA (an MHC Class II molecule) well.

Position 1 is thought to be the most important 'anchor residue' involved in binding between the peptide and the HLA molecule. Position 1 generally favors a hydrophobic side chain—thus, 9-mers that often bind HLA are initiated with V, I, L, M, F, Y, or W. The other positions are much more variable, with different HLA alleles favoring different sets of amino acids at each site. The immunogenicity of the polypeptides described herein were assessed using both in vitro and in silico methods.

A—In Vitro Determination of Human Leukocyte Antigen ("HLA") Binding

In this experiment, synthetic peptides corresponding to different regions in either a wild-type or engineered $^{10}Fn3$ domain sequence were evaluated in HLA binding assays. Similar HLA binding assays are described in Reijonen H, Kwok W W, Use of HLA class II tetramers in tracking antigen-specific T cells and mapping T-cell epitopes, Methods 29(3):282-8 (2003). Each experimental peptide tested in the HLA binding assay was either a wildtype $^{10}Fn3$ domain north pole loop (BC, DE or FG loop) peptide segment having additional amino acids flanking the N- and C-termini of each loop (SEQ ID NOs: 58, 51 and 52), a scaffold region peptide segment from a wildtype $^{10}Fn3$ domain that is positioned N-terminus to the BC loop (SEQ ID NO: 53) or a scaffold region peptide segment from an engineered $^{10}Fn3$ domain that is positioned C-terminus to the BC loop (SEQ ID NO: 54). The experimental peptides were solvated in 100% DMSO at 50× the concentration desired in the assay. Each peptide was then diluted into reaction buffer and titrated serially from 128 µM to 2 µM.

In the HLA binding assay, each of five different HLA allele molecules (either DRB*0101; DRB*0301; DRB*0401; DRB*0701 or DRB*1501 alleles) were loaded separately into wells of a 96-well plate along with the unlabeled experimental peptides and a europium-labeled control (competitor) peptide. The binding mixture was incubated in the wells for 24 hours so as to reach steady equilibrium. The HLA molecule complexes then were captured on an ELISA plate coated with anti-human HLA-DR antibody. Bound HLA-labeled control peptide was measured by time-resolved fluorescence and assessed at 615 nm by a Wallac Victor3 ™ unit (Perkin-Elmer). Binding of experimental peptides was expressed as the percent inhibition of the labeled control peptide (experimental fluorescence/control fluorescence multiplied by 100). From the percent inhibition of labeled control peptide at each concentration, $IC_{50}$ curves were derived for each experimental peptide against the five alleles tested. The results from these experiments are illustrated in FIG. 4.

As shown in FIG. 4, the BC loop peptide was observed to bind to four of the five alleles tested with high affinity suggesting it is an immunodominant sequence within the protein. By contrast, synthetic peptides corresponding to the DE and FG loops bound fewer HLA alleles and with lower affinity, in general. The DE and FG loops are, therefore, not predicted to be immunodominant sequences within the wild-type $^{10}Fn3$ protein.

As shown in FIG. 4, the scaffold region peptide of SEQ ID NO: 53 was found to bind to five of the HLA alleles with high affinity, while the scaffold region peptide of SEQ ID NO: 54 was found to bind to four of the HLA alleles with high affinity. These results suggest that the scaffold region flanking the BC loop of a $^{10}Fn3$ domain are immunodominant regions. The underlined portions of the sequences of SEQ ID NOs: 53 and 54 as shown in FIG. 4 are predicted to be the immunodominant portions of these sequences.

The BC loop, which was found to be an immunodominant loop, was further assessed using the same HLA binding assay. Specifically, three BC loop sequence variant peptides (SEQ ID NOs: 55-57) were examined using the assay and found to show almost identical patterns of strong binding to the HLA alleles tested. The peptide sequence of SEQ ID NO: 55 is the human wildtype sequence and SEQ ID NOs: 56 and 57 are the BC loop regions from $^{10}$Fn3 domains that have been engineered to bind to two different targets. Assuming that a similar binding pattern reflects a shared motif, the sequences were aligned to aid identification of potential anchor residues. Potential position 1 residues of the different BC loop sequences tested are underlined:

```
15  23   30 (sequence position based on SEQ ID
NO: 1)
 |   |    |
PTSLLISW DAPAVTV RYYRITYG (SEQ ID NO: 55)

PTSLLISW SARLKVA RYYRITYG (SEQ ID NO: 56)

PTSLLISW RHPHFPT RYYRITYG (SEQ ID NO: 57)
```

The common sequence portions of these three peptides are the β-strand B, preceding the variable BC loop, and the β-strand C following the BC loop. Each of these portions has several hydrophobic residues (potential position 1 anchors), but those in β-strand C do not have at least 8 more residues following, and therefore cannot be the anchor residues for MHC binding. The hydrophobic residues in the variable BC loop are in different positions in the three peptides, making it unlikely that a single 9-mer position with shared β-strand C residues can be anchored in the BC loops. These results therefore suggest that β-strand B should be useful for designing the peptide anchors.

The most likely positions for anchor residues appear to be "LLI" (positions 18-20 of SEQ ID NO: 1), as these include a stretch of fixed β-strand B residues preceding the BC loop residues. If, for instance, a 9-mer beginning at the first L is anchoring the peptide, the fourth position is always an S, which is favorable for binding to many HLA alleles.

It should be noted that while many fully human sequences are displayed by MHC, the immune system recognizes them as "self" and does not mount an immune response. Further, in Cyno monkeys, which have the identical sequence for $^{10}$Fn3, an immune response was generated upon administration of various different $^{10}$Fn3 polypeptides, but no immune response was generated upon the administration of wildtype $^{10}$Fn3. This indicates that Cyno monkeys recognize the human wildtype $^{10}$Fn3 sequence as being a "self" protein, to which an immune response need not be mounted.

B—In Silico Prediction of HLA Binding

HLA binding may be predicted in silico, for example, using EpiMatrix. EpiMatrix is a proprietary computer algorithm developed by EpiVax, which is used to screen protein sequences for the presence of putative HLA binding motifs. Input sequences are parsed into overlapping 9-mer frames where each frame overlaps the last by 8 amino acids. Each of the resulting frames is then scored for predicted binding affinity with respect to a panel of eight common Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides. The resulting "Z" score is reported. Any 9-mer peptide with an EpiMatrix Z-score in excess of 1.64 is considered a putative HLA binding motif.

Peptide epitopes from a $^{10}$Fn3 polypeptide having the amino acid sequence set forth in SEQ ID NO: 61 were predicted using the EpiMatrix algorithm. Results showed the BC, DE and FG loops of the $^{10}$Fn3 polypeptide have Z-scores of 21.3, 0.9 and 1.1, respectively.

The above in vitro and in silico HLA binding results suggest that the β-strand B/BC loop segment may be a 'hot spot' for the purposes of HLA binding. The β-strand B/BC loop segment may be anchored strongly to MHC molecules by the amino acids in β-strand B, such that at least some variants in BC loop sequences make little difference in the binding to HLA. The strong anchor may make it difficult to deimmunize this segment. However, if the entire stretch is a wildtype sequence, it should be recognized as self by the immune system, and initiate no immune response. Therefore, $^{10}$Fn3 domain polypeptide libraries may be designed to have lower immunogenicity by leaving the BC loop as wildtype, or at the very least, by leaving the residues from D23 to T28 of SEQ ID NO: 1 or 6 as wildtype in order to retain as wildtype any 9-mer peptide anchored at L18, L19, or I20. Examples of libraries in which all or a substantial portion of the BC loop was left wild-type are shown in FIG. 9A. Examples of libraries in which varying portions of the N-terminal regions of the BC loop are left as wild-type are shown in FIG. 9B. Specific examples of $^{10}$Fn3 binders in which the residues corresponding to D23 to T28 of SEQ ID NO: 1 were left wildtype are provided in Example 3. Alternatively, if the BC loop is modified, reduced immunogenicity may be achieved by destroying the strong anchor in this region, i.e., by making modifications in β-strand B, in addition to the modifications in the BC loop. Examples of libraries in which the anchor is removed include libraries in which positions L19 and/or S21 have been diversified thereby increasing the likelihood that members of the library will be missing the anchor residues. Examples of libraries in which the anchor residues are removed are shown in FIG. 9C.

Example 3. Generation of West Side Binders

Libraries of West Side ("WS") binder polypeptides comprising a modified $^{10}$Fn3 domain were screened using mRNA display (Xu et al Chem Biol. 2002 August; 9(8): 933-42) for binding to murine IL-17, murine DLL4 or human PXR as targets. The WS binders were designed such that the BC loop sequence was left as wildtype. The WS1 library design (see FIG. 9A) was used to identify binders to the target human PXR and the WS-LI1 library design (see FIG. 9A) was used to identify binders to the targets murine IL-17 or murine DLL4. Target binding was monitored by qPCR and populations were cloned and expressed in E. coli when a specific binding signal was observed.

Example 4. Disruption of DLL4 and Notch 1 Interaction by WS-LI1 Binders Capable of Binding Murine DLL4

Figure 5:
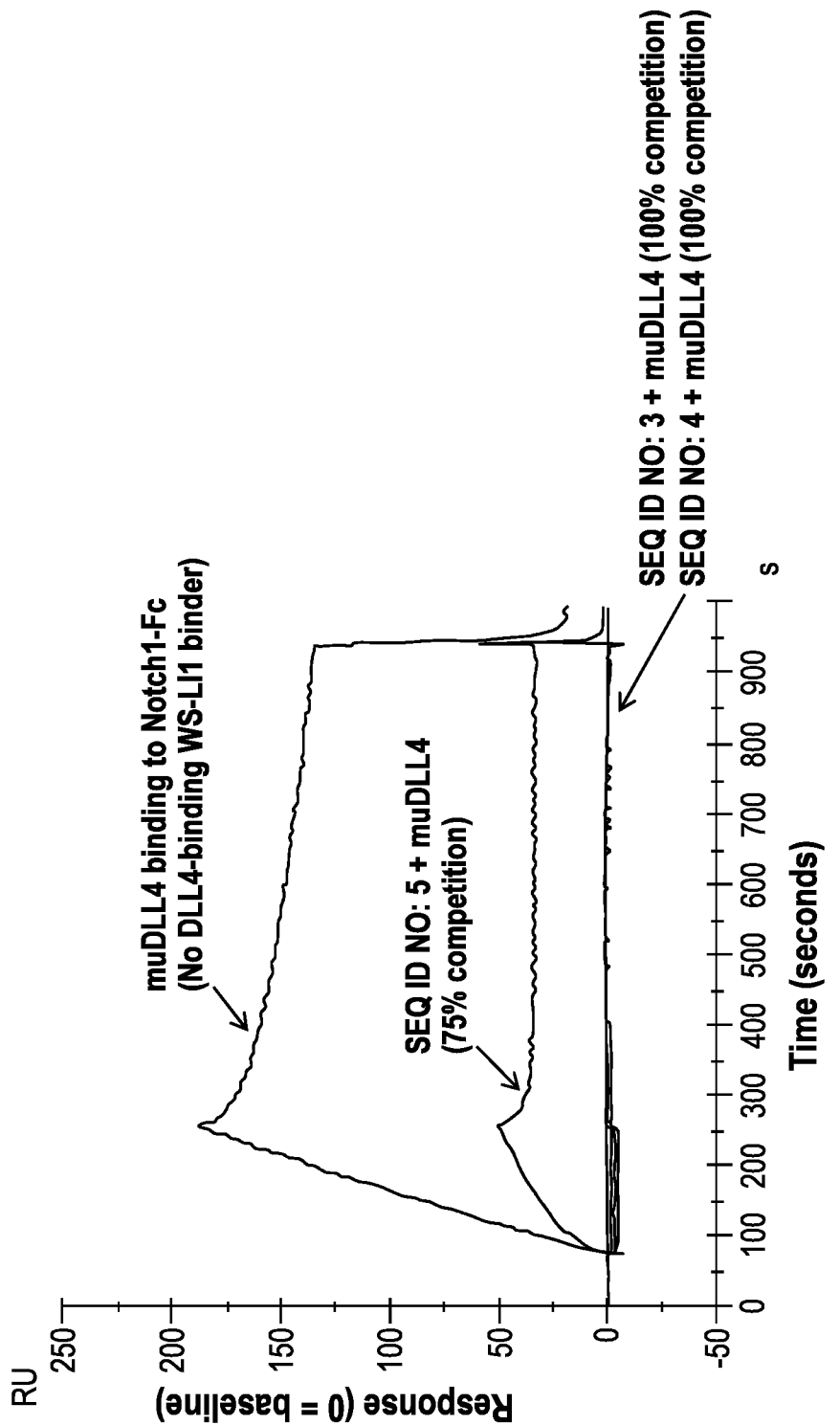
FIG. 5: Notch 1:murine DLL4 competition assay results showing that the WS-LI1 binders of SEQ ID NOs: 3 and 4 were capable of 100% inhibition, and that the WS-LI1 binder of SEQ ID NO: 5 was capable of 75% inhibition, of the interaction between Notch 1 and murine DLL4, as determined by Biacore analysis.

DLL4 is a ligand for the Notch 1 protein. The ability of $^{10}$Fn3 polypeptides having the WS-LI1 design to disrupt the interaction between Notch 1 and murine DLL4 was assessed by employing a competitive Biacore experiment. Approximately 4500 RU of Notch1-Fc was immobilized on a CM5 Biacore chip. 2 µM of WS-LI1 binders were equilibrated with 20 nM murine DLL4 in HBSP buffer and 5 mM CaCl$_2$ along with a control in which no polypeptide was added. Each sample was flowed over the chip and binding of murine DLL4 was compared to the control in which no WS-LI1 polypeptide was added, so that a reduction in signal corresponded to inhibition of the Notch 1:murine DLL4 interaction. Between each sample run, the chip was regenerated with two 30-second washes in HBSP pH 7.4 and 50 mM EDTA. The results of this experiment are shown in FIG. 5. The polypeptides having the sequence of SEQ ID NO: 3 and 4 were each found to result in 100% competition of the interaction between Notch1 and murine DLL4. The polypeptides having the sequence of SEQ ID NO: 5 were able to induce 75% competition of the interaction between Notch 1 and murine DLL4.

Example 5. Size Exclusion Chromatography Analysis of WS-LI1 Binders Capable of Binding Murine DLL4

Size exclusion chromatography was utilized to demonstrate that the competition results observed in Example 4 were due to monomeric forms of the WS-LI1 binders tested. The WS-LI1 binders having amino acid sequences of either SEQ ID NO: 3 or 4 were predominantly monomeric, whereas the WS-LI1 binder having the amino acid sequence of SEQ ID NO: 5 contained a mixture of monomeric and aggregated proteins. The results from this experiment are shown in FIG. 6 and illustrate that the WS-LI1 binders tested in Example 4 were acting as a monomeric species, suggesting that the binders exist as stable, well-folded polypeptides.

Example 6. Stability of WS-LI1 Binders Capable of Binding Murine DLL4

Stability of the polypeptides described in Example 4 was assessed by a thermal shift fluorescence-based assay (TSF). The polypeptide having the amino acid sequence of SEQ ID NO: 3 had a transition at 59° C. The polypeptide having the amino acid sequence of SEQ ID NO: 4 had a transition at 49° C. No transition was observed for the polypeptide having the amino acid sequence of SEQ ID NO: 5.

Example 7. Disruption of the Interaction Between Murine IL-17 and Murine IL-17RA by WS-LI1 Binders Capable of Binding Murine IL-17

IL-17 is a ligand for the IL-17 receptor A protein, IL-17RA. The ability of $^{10}$Fn3 domains having the WS-LI1 design to disrupt the interaction between murine IL-17 and murine IL-17RA was assessed by employing a competitive Alphascreen experiment. Streptavidin donor beads, anti-human IgG acceptor beads, 1.5 nM murine IL-17RA-Fc and 2.5 nM biotinylated murine IL-17 were combined according to the manufacturer's instructions to give a robust Alphascreen signal. Polypeptides having the sequences of either SEQ ID NO: 45, 46 or 47 were assessed for their ability to inhibit this signal when added to the mixture at 1 µM concentrations. The polypeptide having the sequence of SEQ ID NO: 45 caused an 83% inhibition, the polypeptide having the sequence of SEQ ID NO: 46 caused a 94% inhibition and the polypeptide having the sequence of SEQ ID NO: 47 caused an 81% inhibition of the Alphascreen signal. These results demonstrate that the WS-LI1 library design produced $^{10}$Fn3 domains capable of binding IL-17 and effectively inhibiting the interaction between murine IL-17 and its receptor.

Example 8. Size Exclusion Chromatography Analysis of WS-LI1 Binders Capable of Binding Murine IL-17

Size exclusion chromatography was utilized to demonstrate that the competition results observed in Example 7 were due to monomeric forms of the WS-LI1 binders tested. The WS-LI1 binders having amino acid sequences of either SEQ ID NO: 45, 46 or 47 were predominantly monomeric. The results from this experiment are shown in FIG. 7 and illustrate that the WS-LI1 binders tested in Example 7 were acting as a monomeric species, suggesting that the binders exist as stable, well-folded polypeptides.

Example 9. Stability of WS-LI1 Binders Capable of Binding Murine IL-17

Stability of the polypeptides described in Example 7 was assessed by TSF. The polypeptide having the amino acid sequence of SEQ ID NO: 45 had a transition at 51° C. The polypeptide having the amino acid sequence of SEQ ID NO: 46 had a transition at 60° C. No transition was observed for the polypeptide having the amino acid sequence of SEQ ID NO: 47.

Example 10. Characterization of Binding Properties of WS1 Binders Capable of Binding Human PXR WS1 binders that were capable of binding to PXR were characterized using a Biacore binding assay and GST-tagged PXR. 14000 RU of anti-GST antibody was immobilized on a Biacore chip and GST-PXR was captured by flowing a 50 nM solution over the chip for 3 min at a rate of 5 µL/min. WS1 binders were flowed over the chip at 0.5-2 µM concentration to observe binding relative to a control that lacked PXR. The chip was stripped between each run using two 30 second washes with 10 mM glycine, pH 2.0 and fresh GST-PXR was captured. Under these conditions, 146 RU of WS1 binders having the amino acid sequence of SEQ ID NO: 48 bound the GST-PXR, and 81 RU of WS1 binders having the amino acid sequence of SEQ ID NO: 49 bound the GST-PXR. These results demonstrate that the WS1 binders having the amino acid sequence of either SEQ ID NO: 48 or 49 are capable of binding GST-PXR.

Example 11. Size Exclusion Chromatography Analysis of WS1 Binders Capable of Binding Human PXR Size exclusion chromatography was utilized to demonstrate that the binding results observed in Example 10 were due to monomeric forms of the WS1 binders tested. The WS1 binders having amino acid sequences of either SEQ ID NO: 48 or 49 were predominantly monomeric. The results from this experiment are shown in FIG. 8 and illustrate that the WS1 binders tested in Example 10 were acting as a monomeric species, suggesting that the binders exist as stable, well-folded polypeptides.

Example 12. Sequences and Binding Characteristics of $^{10}$Fn3 Polypeptides Binding to Human PXR This Example describes 6 additional $^{10}$Fn3 polypeptides that bind to human PXR ligand binding domain (LBD). It also provides binding characteristics of these 6 polypeptides as well as the two that are described in Example 10 (and having SEQ ID NOs: 48 and 49).

¹⁰Fn3 polypeptides having the amino acid sequences set forth in FIG. 10 were identified by screening various libraries. For example, Adnectin-1 was isolated from an NP1 library (see FIG. 9C). The ¹⁰Fn3 polypeptides were synthesized as follows. Nucleic acids encoding the ¹⁰Fn3 polypeptides were cloned in pET9D vector and then expressed in *Escherichia coli* at 20° C. The lysates were purified in a single step using Ni-agarose affinity chromatography.

The $K_D$ values for the ¹⁰Fn3 polypeptides were determined by surface Plasmon resonance (SPR) on a Biacore T100 instrument (GE Healthcare), by injecting a concentration series of the ¹⁰Fn3 polypeptides over human PXR-GST (Invitrogen) that had been captured on chip immobilized with an anti-GST antibody (GE Healthcare). Regeneration of the chip surface between kinetic cycles was performed using 10 mM Glycine, pH 2. Kinetic parameters for both were calculated using Biacore T100 software. The results are set forth in Table 1.

TABLE 1

Binding characteristics of Adnectins-1 to -8 to human PXR

| Adnectin | ka (1/Ms) | kd (1/s) | KD (nM) |
|---|---|---|---|
| Adnectin-1 | 1.04E+05 ± 1.20E+04 | 1.19E−03 ± 3.46E−05 | 11.4 ± 1 |
| Adnectin-2 | 1.62E+05 ± 5.37E+03 | 4.58E−03 ± 3.53E−04 | 97.8 ± 3.8 |
| Adnectin-3 | 1.62E+04 ± 6.75E+04 | 3.78E−04 ± 2.23E−05 | 2.5 ± 0.9 |
| Adnectin-4 | 2.15E+04 ± 5.30E+02 | 1.68E−04 | 7.8 |
| Adnectin-5 | 5.09E+05 ± 1.07E+05 | 2.70E−03 ± 2.36E−04 | 5.4 ± 0.7 |
| Adnectin-6 | 6.80E+05 ± 1.69E+05 | 1.26E−03 ± 1.72E−04 | 1.9 ± 0.2 |
| Adnectin-7 | 2.88E+05 ± 2.38E+04 | 8.82E−05 ± 1.15E−06 | 0.31 ± 0.03 |
| Adnectin-8 | 4.17E+04 ± 8.22E+03 | 1.82E−04 ± 2.78E−05 | 4.4 ± 0.2 |

Adnectin-1 was effectively used as a co-crystallization chaperone of human PXR with a small molecule, and shown to bind to the ligand binding domain of PXR. The X-ray data provided information on the interaction between the small molecule and the PXR ligand binding domain.

Example 13. Lack of RGD in FG Loop Prevents Binding of ¹⁰Fn3 Polypeptides to Fibronectin and Vitronectin Recombinant human integrin αVβ3 (R&D Systems, Minneapolis Minn.) was diluted to 40 ug/mL in Acetate buffer pH 5.0 (GE Healthcare, Piscataway N.J.), and. then immobilized on a CM7 chip (GE Healthcare) using standard amine coupling techniques. 500 nM fibronectin (Roche Diagnostics, Indianapolis, Ind.) and vitronectin (R&D Systems) and 5 μM of either non-binding control ¹⁰Fn3 molecule (consisting of SEQ ID NO: 6 with an additional MG at the N-terminus and with a single amino acid substitution that changes RGD to RGE) or targeted ¹⁰Fn3 molecules (having a mutated FG loop that does not contain an RGD motif) were flowed over the top of the immobilized integrin. Binding RU was collected at the end of the sample injection. The results indicate that the lack of RGD in the FG loop results in abolishing binding of ¹⁰Fn3 molecules to fibronectin and vitronectin.

Example 14. Characteristics of Molecules Obtained from Various Libraries

This Example shows various characteristics of molecules obtained from 11 different libraries. The following libraries were made:

LI-1 library, which is a mixture of libraries LI-1(a), LI-1(b) and LI-1(c), comprising ¹⁰Fn3 molecules having the amino acid sequences that are provided in FIG. 9B. The amino acid residues that are underlined are those that were varied to any amino acid by substitution. Residues that are underlined may be the wild-type residues;

LI-3 library comprising ¹⁰Fn3 molecules having the amino acid sequence that is provided in FIG. 9B ("LI-3(b)), wherein the amino acid residues that are boxed were varied by substitution to any amino acid or deletion or addition. Residues that are boxed may be the wild-type residues;

WS-LI1 library, comprising ¹⁰Fn3 molecules having the amino acid sequence set forth in FIG. 9A, wherein the amino acid residues that are boxed were varied by substitution to any amino acid or deletion or addition. Residues that are boxed may be the wild-type residues;

LI-S9 library, comprising ¹⁰Fn3 molecules having the amino acid sequence set forth in FIG. 9A, wherein the boxed residues were varied by amino acid substitution, addition or deletion, the underlined residues were varied by substitution, and the highlighted residue is changed to an E. Residues that are boxed or underlined may be the wild-type residues;

LI-S8 library, comprising ¹⁰Fn3n3 molecules having the amino acid sequence set forth in FIG. 9A, wherein the boxed residues were varied by substitution, addition or deletion, and the highlighted residue is changed to an E. Residues that are boxed may be the wild-type residues;

NP4_FG library, comprising ¹⁰Fn3 molecules having the amino acid sequence set forth in FIG. 9C, wherein the boxed residues were varied by amino acid substitution, addition or deletion, and the underlined residues were varied by substitution. Residues that are boxed or underlined may be the wild-type residues. This library corresponds to the NP4 library, wherein only residues in FG, F and G were varied.

WS2'_CD library, comprising ¹⁰Fn3 molecules having the amino acid sequence set forth in FIG. 9A, wherein the boxed residues were varied by amino acid substitution, addition or deletion, and the underlined residues were varied by substitution. Residues that are boxed or underlined may be the wild-type residues. This library corresponds to the WS2' library, wherein only residues in CD, C and D were varied;

NP1' library, comprising ¹⁰Fn3 molecules having the amino acid sequence set forth in FIG. 9C, wherein the boxed residues were varied by amino acid substitution, addition or deletion, and the underlined residues were varied by substitution. Residues that are boxed or underlined may be the wild-type residues;

NP4 library, comprising ¹⁰Fn3 molecules having the amino acid sequence set forth in FIG. 9C, wherein the boxed residues were varied by amino acid substitution, addition or deletion, and the underlined residues were varied by substitution. Residues that are boxed or underlined may be the wild-type residues; and WS2' library, comprising ¹⁰Fn3 molecules having the amino acid sequence set forth in FIG. 9A, wherein the boxed residues were varied by amino acid substitution, addition or deletion, and the underlined residues were varied by substitution. Residues that are boxed or underlined may be the wild-type residues.

Clones from each of the libraries were expressed and purified. The resulting ¹⁰Fn3 molecules were run on the Perkin Elmer LabChip GX with the low molecular weight protein ladder per the manufacturers' recommendations. The concentrations of the ¹⁰Fn3 molecules were extrapolated from a standard curve of SGE also run on the LabChip GX. Samples with concentrations higher than that of the standard curve were classified as off-curve-high (OCH). The percent of OCH wells and the average concentration for each library was determined. The results indicate that the fraction of OCH wells and average concentration of measurable samples follow similar patterns.

The resistance to aggregation of $^{10}$Fn3 molecules from each of the libraries was also tested. Between 19-200 clones from each library were assayed for aggregation and retention time by size exclusion chromatography (SEC) according to manufacturers' recommendations. The SEC chromatogram was integrated for each clone and evaluated for peaks that eluted between the times of a 17 kDa and 1.3 kDa standard. Clones having greater than 90% area in this retention time window received an SEC score of 1, 50%-90% a score of 2, 5%-50% a score of 3, and less than 5% a score of 4. Fraction of SEC score 1 or 2 is measure of resistance to aggregation and fraction SEC 4 is a measure of load on SEC screening. The results indicate that fraction of SEC 1 or 2 and fraction of SEC 4 follow approximately inverse patterns.

Target binding of clones from each library was determined by ELISA. The proteins that the clones were directed against were coated at 2.5 μg/mL on a Nunc Maxisorp Plate. Plates were blocked with Casein (ThermoScientific #37532) and then incubated with the $^{10}$Fn3 molecules. Binding clones were detected through a His-tag using an HRP labeled anti-His antibody (R&D Systems #mAb050H). Hits were determined as anything which gave a signal greater than 2× that of blank wells. The fraction of hits is a measure of load on screening. All libraries had at least an expected number of hits.

The existence of multiple epitopes to which members of each library bound was also determined. For three targets this involved competitive Alphascreen assays as referenced in Example 7. For these targets, multiple epitope coverage was proven by the existence of competitors and non-competitors from proven target binders. For one multi-domain target, multiple epitope binding was demonstrated using an ELISA with recombinant versions of the individual subdomains. The fraction of targets for which multiple epitopes are found is a measure of probability of finding diverse biological activity in a library. The results of multiple epitope coverage for multiple targets with the different libraries indicate diversity of blocking.

INCORPORATION BY REFERENCE

All documents and references, including patent documents and websites, described herein are individually incorporated by reference to into this document to the same extent as if there were written in this document in full or in part.

SEQUENCE LISTING

```
<160> NUMBER OF SEQ ID NOS: 124

<210> SEQ ID NO 1
<211> LENGTH: 101
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 2
<211> LENGTH: 85
<212> TYPE: PRT
<213> ORGANISM: Homo sapiens

<400> SEQUENCE: 2

Leu Glu Val Val Ala Ala Thr Pro Thr Ser Leu Leu Ile Ser Trp Asp
1               5                   10                  15

Ala Pro Ala Val Thr Val Arg Tyr Tyr Arg Ile Thr Tyr Gly Glu Thr
            20                  25                  30

Gly Gly Asn Ser Pro Val Gln Glu Phe Thr Val Pro Gly Ser Lys Ser
```

```
              35                  40                  45
Thr Ala Thr Ile Ser Gly Leu Lys Pro Gly Val Asp Tyr Thr Ile Thr
 50                  55                  60

Val Tyr Ala Val Thr Gly Arg Gly Asp Ser Pro Ala Ser Ser Lys Pro
65                  70                  75                  80

Ile Ser Ile Asn Tyr
                 85
```

<210> SEQ ID NO 3
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 3

```
Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                20                  25                  30

Tyr Tyr Arg Ile Thr Tyr Gly Glu Gln His Ser Lys Tyr Pro His Gln
             35                  40                  45

Glu Phe Thr Val Pro Gly Ser Lys Ser Thr Ala Thr Ile Ser Gly Leu
 50                  55                  60

Lys Pro Gly Val Asp Tyr Thr Ile Thr Val Tyr Ala Val Thr Ile Gln
65                  70                  75                  80

Pro Gln Asp Pro Glu Gln Asp Tyr Gln Tyr His Tyr Tyr Glu Thr Ser
                85                  90                  95

Ser Lys Pro Ile Ser Ile Asn Tyr Arg Thr Glu Ile Asp Lys Pro Ser
            100                 105                 110

Gln
```

<210> SEQ ID NO 4
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 4

```
Met Gly Val Ser Asp Val Pro Arg Asp Leu Glu Val Val Ala Ala Thr
 1               5                  10                  15

Pro Thr Ser Leu Leu Ile Ser Trp Asp Ala Pro Ala Val Thr Val Arg
                20                  25                  30

Tyr Tyr Arg Ile Thr Tyr Gly Glu His Val Ala Asp His Phe Asp His
             35                  40                  45

Asn Gln Glu Phe Thr Val Pro Gly Ser Lys Ser Thr Ala Thr Ile Ser
 50                  55                  60

Gly Leu Lys Pro Gly Val Asp Tyr Thr Ile Thr Val Tyr Ala Val Thr
65                  70                  75                  80

Tyr Gln Phe Gln Asp Pro Glu Glu His Tyr Tyr Tyr His Phe Tyr Asp
                85                  90                  95

Ser Ser Ser Lys Pro Ile Ser Ile Asn Tyr Arg Thr Glu Ile Asp Lys
            100                 105                 110

Pro Ser Gln
        115
```

```
<210> SEQ ID NO 5
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 5
```

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Tyr His Glu His Tyr His Ser Pro
        35                  40                  45

Gly Phe Ser Gln Lys Tyr His Tyr Glu Gln Glu Phe Thr Val Pro Gly
    50                  55                  60

Ser Lys Ser Thr Ala Thr Ile Ser Gly Leu Lys Pro Gly Val Asp Tyr
65                  70                  75                  80

Thr Ile Thr Val Tyr Ala Val Thr Gly His Lys His Tyr His Tyr Tyr
                85                  90                  95

Tyr Tyr Tyr His His His Ser Ser Lys Pro Ile Ser Ile Asn Tyr Arg
            100                 105                 110

Thr Glu Ile Asp Lys Pro Ser Gln
            115                 120

```
<210> SEQ ID NO 6
<211> LENGTH: 94
<212> TYPE: PRT
<213> ORGANISM: Homo sapiens

<400> SEQUENCE: 6
```

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

```
<210> SEQ ID NO 7
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 7
```

Glu Ile Glu Lys
1

```
<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide
```

<400> SEQUENCE: 8

Glu Ile Glu Lys Pro Cys
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 9

Met Gly Val Ser Asp Val Pro Arg Asp Leu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 10

Val Ser Asp Val Pro Arg Asp Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Gly Val Ser Asp Val Pro Arg Asp Leu
1               5

<210> SEQ ID NO 12
<211> LENGTH: 94
<212> TYPE: PRT
<213> ORGANISM: Artificial Sequence
<220> FEATURE:
<223> OTHER INFORMATION: Synthetic polypeptide

<400> SEQUENCE: 12

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr
                85                  90

<210> SEQ ID NO 13
<211> LENGTH: 109
<212> TYPE: PRT
<213> ORGANISM: Artificial Sequence
<220> FEATURE:

<223> OTHER INFORMATION: Synthetic polypeptide

<400> SEQUENCE: 13

```
Met Gly Val Ser Asp Val Pro Arg Asp Leu Glu Val Val Ala Ala Thr
1               5                   10                  15

Pro Thr Ser Leu Leu Ile Ser Trp Ser Arg Pro Lys Gly Ser Ile Lys
            20                  25                  30

Tyr Tyr Arg Ile Thr Tyr Gly Glu Thr Gly Gly Asn Ser Pro Val Gln
        35                  40                  45

Glu Phe Thr Val Pro Asn Ser Gln Tyr Thr Ala Thr Ile Ser Gly Leu
    50                  55                  60

Lys Pro Gly Val Asp Tyr Thr Ile Thr Val Tyr Ala Val Tyr Gly Tyr
65                  70                  75                  80

Pro Tyr Gln Glu Pro His Tyr Tyr Pro Ile Ser Ile Asn Tyr Arg Thr
                85                  90                  95

Glu Ile Asp Lys Pro Ser Gln His His His His His
            100                 105
```

<210> SEQ ID NO 14
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 14

```
Met Gly Val Ser Asp Val Pro Arg Asp Leu Glu Val Val Thr Ala Thr
1               5                   10                  15

Pro Thr Ser Leu Leu Ile Ser Trp Asp Gly Pro Lys Tyr Tyr Val Lys
            20                  25                  30

Tyr Tyr Arg Ile Thr Tyr Gly Glu Thr Gly Gly Asn Ser Pro Val Gln
        35                  40                  45

Glu Phe Thr Val Pro Arg Thr Asp His Thr Ala Thr Ile Ser Gly Leu
    50                  55                  60

Lys Pro Gly Val Asp Tyr Thr Ile Thr Val Tyr Ala Val Lys Gly Gln
65                  70                  75                  80

Tyr Gly Pro Tyr Tyr Gly Ser Arg Pro Ile Ser Ile Asn Tyr Arg Thr
                85                  90                  95

Glu Ile Asp Lys Pro Ser Gln His His His His His
            100                 105
```

<210> SEQ ID NO 15
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 15

```
Met Gly Val Ser Asp Val Pro Arg Asp Leu Glu Val Val Ala Ala Thr
1               5                   10                  15

Pro Thr Ser Leu Leu Ile Ser Trp Ser Gln Pro Gly Arg Tyr Val Lys
            20                  25                  30

Tyr Tyr Arg Ile Thr Tyr Gly Glu Thr Gly Gly Asn Ser Pro Val Gln
        35                  40                  45

Glu Phe Thr Val Pro Asn Asp Thr Tyr Thr Ala Thr Ile Ser Gly Leu
    50                  55                  60

Lys Pro Gly Val Asp Tyr Thr Ile Thr Val Tyr Ala Val Tyr Gly Lys
```

```
                65                  70                  75                  80
Tyr Gly Pro Tyr Tyr Gly Tyr Asp Pro Ile Ser Ile Asn Tyr Arg Thr
                    85                  90                  95
Glu Ile Asp Lys Pro Ser Gln His His His His His
                100                 105
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(16)
<223> OTHER INFORMATION: /note="see specification as filed for detailed
      description of substitutions and preferred embodiments"

<400> SEQUENCE: 16

Met Gly Ser Asp Val Pro Arg Asp Leu
1               5
```

```
<210> SEQ ID NO 17
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(8)
<223> OTHER INFORMATION: /note="see specification as filed for detailed
      description of substitutions and preferred embodiments"

<400> SEQUENCE: 17

Met Gly Asp Val Pro Arg Asp Leu
1               5
```

```
<210> SEQ ID NO 18
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
```

```
      preference with respect to those in the annotations for said
      positions"
<220> FEATURE:
<221> NAME/KEY: misc_feature
<222> LOCATION: (1)..(7)
<223> OTHER INFORMATION: /note="see specification as filed for detailed
      description of substitutions and preferred embodiments"

<400> SEQUENCE: 18

Met Gly Val Pro Arg Asp Leu
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(6)
<223> OTHER INFORMATION: /note="see specification as filed for detailed
      description of substitutions and preferred embodiments"

<400> SEQUENCE: 19

Met Gly Pro Arg Asp Leu
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(5)
<223> OTHER INFORMATION: /note="see specification as filed for detailed
      description of substitutions and preferred embodiments"

<400> SEQUENCE: 20

Met Gly Arg Asp Leu
1               5

<210> SEQ ID NO 21
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: VARIANT
<222> LOCATION: (1)..(2)
```

```
<223> OTHER INFORMATION: /replace=" "
<220> FEATURE:
<221> NAME/KEY: misc_feature
<222> LOCATION: (1)..(2)
<223> OTHER INFORMATION: /note="Residues given in the sequence have no
      preference with respect to those in the annotations for said
      positions"
<220> FEATURE:
<221> NAME/KEY: misc_feature
<222> LOCATION: (1)..(4)
<223> OTHER INFORMATION: /note="see specification as filed for detailed
      description of substitutions and preferred embodiments"

<400> SEQUENCE: 21

Met Gly Asp Leu
1

<210> SEQ ID NO 22
<211> LENGTH: 166
<212> TYPE: PRT
<213> ORGANISM: Artificial Sequence
<220> FEATURE:
<223> OTHER INFORMATION: Synthetic 10Fn3 domain core sequence version 3
<220> FEATURE:
<221> NAME/KEY: misc_feature
<222> LOCATION: (1)..(166)
<223> OTHER INFORMATION: /note="see specification as filed for detailed
      description of substitutions and preferred embodiments"
<220> FEATURE:
<221> NAME/KEY: MOD_RES
<222> LOCATION: (14)..(33)
<223> OTHER INFORMATION: Any amino acid
<220> FEATURE:
<221> NAME/KEY: misc_feature
<222> LOCATION: (14)..(33)
<223> OTHER INFORMATION: /note="This region may encompass 2 to 20
      residues"
<220> FEATURE:
<221> NAME/KEY: VARIANT
<222> LOCATION: (16)..(33)
<223> OTHER INFORMATION: /replace=" "
<220> FEATURE:
<221> NAME/KEY: misc_feature
<222> LOCATION: (16)..(33)
<223> OTHER INFORMATION: /note="Residues given in the sequence have no
      preference with respect to those in the annotations for said
      positions"
<220> FEATURE:
<221> NAME/KEY: MOD_RES
<222> LOCATION: (39)..(58)
<223> OTHER INFORMATION: Any amino acid
<220> FEATURE:
<221> NAME/KEY: misc_feature
<222> LOCATION: (39)..(58)
<223> OTHER INFORMATION: /note="This region may encompass 2 to 20
      residues"
<220> FEATURE:
<221> NAME/KEY: VARIANT
<222> LOCATION: (41)..(58)
<223> OTHER INFORMATION: /replace=" "
<220> FEATURE:
<221> NAME/KEY: misc_feature
<222> LOCATION: (41)..(58)
<223> OTHER INFORMATION: /note="Residues given in the sequence have no
      preference with respect to those in the annotations for said
      positions"
<220> FEATURE:
<221> NAME/KEY: MOD_RES
<222> LOCATION: (64)..(83)
<223> OTHER INFORMATION: Any amino acid
<220> FEATURE:
<221> NAME/KEY: misc_feature
<222> LOCATION: (64)..(83)
<223> OTHER INFORMATION: /note="This region may encompass 2 to 20
      residues"
<220> FEATURE:
<221> NAME/KEY: VARIANT
```

```
-continued

<222> LOCATION: (66)..(83)
<223> OTHER INFORMATION: /replace=" "
<220> FEATURE:
<221> NAME/KEY: misc_feature
<222> LOCATION: (66)..(83)
<223> OTHER INFORMATION: /note="Residues given in the sequence have no
      preference with respect to those in the annotations for said
      positions"
<220> FEATURE:
<221> NAME/KEY: MOD_RES
<222> LOCATION: (87)..(106)
<223> OTHER INFORMATION: Any amino acid
<220> FEATURE:
<221> NAME/KEY: misc_feature
<222> LOCATION: (87)..(106)
<223> OTHER INFORMATION: /note="This region may encompass 2 to 20
      residues"
<220> FEATURE:
<221> NAME/KEY: VARIANT
<222> LOCATION: (89)..(106)
<223> OTHER INFORMATION: /replace=" "
<220> FEATURE:
<221> NAME/KEY: misc_feature
<222> LOCATION: (89)..(106)
<223> OTHER INFORMATION: /note="Residues given in the sequence have no
      preference with respect to those in the annotations for said
      positions"
<220> FEATURE:
<221> NAME/KEY: MOD_RES
<222> LOCATION: (113)..(132)
<223> OTHER INFORMATION: Any amino acid
<220> FEATURE:
<221> NAME/KEY: misc_feature
<222> LOCATION: (113)..(132)
<223> OTHER INFORMATION: /note="This region may encompass 2 to 20
      residues"
<220> FEATURE:
<221> NAME/KEY: VARIANT
<222> LOCATION: (115)..(132)
<223> OTHER INFORMATION: /replace=" "
<220> FEATURE:
<221> NAME/KEY: misc_feature
<222> LOCATION: (115)..(132)
<223> OTHER INFORMATION: /note="Residues given in the sequence have no
      preference with respect to those in the annotations for said
      positions"
<220> FEATURE:
<221> NAME/KEY: MOD_RES
<222> LOCATION: (140)..(159)
<223> OTHER INFORMATION: Any amino acid
<220> FEATURE:
<221> NAME/KEY: misc_feature
<222> LOCATION: (140)..(159)
<223> OTHER INFORMATION: /note="This region may encompass 2 to 20
      residues"
<220> FEATURE:
<221> NAME/KEY: VARIANT
<222> LOCATION: (142)..(159)
<223> OTHER INFORMATION: /replace=" "
<220> FEATURE:
<221> NAME/KEY: misc_feature
<222> LOCATION: (142)..(159)
<223> OTHER INFORMATION: /note="Residues given in the sequence have no
      preference with respect to those in the annotations for said
      positions"

<400> SEQUENCE: 22

Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa
        35                  40                  45

Xaa Xaa Xaa Xaa Xaa Xaa Xaa Xaa Xaa Xaa Tyr Arg Ile Thr Tyr Xaa
    50                  55                  60
```

```
Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa
            85                  90                  95

Xaa Xaa Xaa Xaa Xaa Xaa Xaa Xaa Xaa Ala Thr Ile Ser Gly Leu
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Ile
145                 150                 155                 160

Ser Ile Asn Tyr Arg Thr
                165

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 23

Glu Gly Ser Gly Cys
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 24

Glu Ile Glu Lys Pro Cys Gln
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 25

Glu Ile Glu Lys Pro Ser Gln
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 26

Glu Ile Glu Lys Pro
1               5

<210> SEQ ID NO 27
<211> LENGTH: 6
<212> TYPE: PRT
<213> ORGANISM: Artificial Sequence
```

```
<220> FEATURE:
<223> OTHER INFORMATION: Synthetic polypeptide

<400> SEQUENCE: 27

Glu Ile Glu Lys Pro Ser
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 28

Glu Gly Ser Gly Ser
1               5

<210> SEQ ID NO 29
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 29

Glu Ile Asp Lys
1

<210> SEQ ID NO 30
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 30

Glu Ile Asp Lys Pro Ser Gln
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31

Glu Ile Asp Lys Pro Cys Gln
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 32

Pro Ser Thr Ser Thr Ser Thr
1               5

<210> SEQ ID NO 33
<211> LENGTH: 3
<212> TYPE: PRT
<213> ORGANISM: Artificial Sequence
<220> FEATURE:
```

<223> OTHER INFORMATION: Synthetic polypeptide

<400> SEQUENCE: 33

Gly Pro Gly
1

<210> SEQ ID NO 34
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 34

Gly Pro Gly Pro Gly Pro Gly
1               5

<210> SEQ ID NO 35
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 35

Gly Pro Gly Pro Gly Pro Gly Pro Gly Pro Gly
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 36

Pro Ala Pro Ala Pro Ala
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 37

Pro Ala Pro Ala Pro Ala Pro Ala Pro Ala Pro Ala
1               5                   10

<210> SEQ ID NO 38
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 38

Pro Ala Pro Ala Pro Ala Pro Ala Pro Ala Pro Ala Pro Ala Pro Ala
1               5                   10                  15
Pro Ala

<210> SEQ ID NO 39
<211> LENGTH: 10
<212> TYPE: PRT
<213> ORGANISM: Artificial Sequence

```
<220> FEATURE:
<223> OTHER INFORMATION: Synthetic polypeptide

<400> SEQUENCE: 39

Gly Ser Gly Ser Gly Ser Gly Ser Gly Ser
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 40

Gly Ser Gly Ser Gly Ser Gly Ser Gly Ser Gly Ser Gly Ser Gly Ser
1               5                   10                  15

Gly Ser Gly Ser
            20

<210> SEQ ID NO 41
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 41

Gly Gly Gly Gly Ser Gly Gly Gly Gly Ser Gly Gly Gly Gly Ser
1               5                   10                  15

<210> SEQ ID NO 42
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 42

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 43
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 43

Gly Gly Gly Gly Ser Gly Gly Gly Gly Ser Gly Gly Gly Ser Gly
1               5                   10                  15

<210> SEQ ID NO 44
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 44

His His His His His His
1               5
```

<210> SEQ ID NO 45
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 45

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Tyr His Ala Phe Phe Ala Ser Asn
        35                  40                  45

Gly Lys Tyr Tyr Phe Tyr Ile Gln Glu Phe Thr Val Pro Gly Ser Lys
    50                  55                  60

Ser Thr Ala Thr Ile Ser Gly Leu Lys Pro Gly Val Asp Tyr Thr Ile
65                  70                  75                  80

Thr Val Tyr Ala Val Thr Asp Asp Thr Val His His Gly Asp Ser Asn
                85                  90                  95

Tyr His Ser Ser Lys Pro Ile Ser Ile Asn Tyr Arg Thr Glu Ile Asp
            100                 105                 110

Lys Pro Ser Gln
        115
```

<210> SEQ ID NO 46
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 46

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Tyr Ser Ser Phe Phe Gln His Gln
        35                  40                  45

Gly Gln Tyr Tyr His Tyr Ile Gln Glu Phe Thr Val Pro Gly Ser Lys
    50                  55                  60

Ser Thr Ala Thr Ile Ser Gly Leu Lys Pro Gly Val Asp Tyr Thr Ile
65                  70                  75                  80

Thr Val Tyr Ala Val Thr Gln His Glu His Ser Gln Asp Ser Ser Lys
                85                  90                  95

Pro Ile Ser Ile Asn Tyr Arg Thr Glu Ile Asp Lys Pro Ser Gln
            100                 105                 110
```

<210> SEQ ID NO 47
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 47

```
Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
```

```
                    20                  25                  30
Tyr Tyr Arg Ile Thr Tyr Gly Glu Phe Ser Gln Phe Val His Ser Asp
                35                  40                  45

Gly Glu Tyr Tyr Gln Glu Tyr Gln Glu Phe Thr Val Pro Gly Ser Lys
            50                  55                  60

Ser Thr Ala Thr Ile Ser Gly Leu Lys Pro Gly Val Asp Tyr Thr Ile
 65                 70                  75                  80

Thr Val Tyr Ala Val Thr Gly Gln Tyr Asp Gln Asp Asp Glu Pro Ser
                    85                  90                  95

Ser Lys Pro Ile Ser Ile Asn Tyr Arg Thr Glu Ile Asp Lys Pro Ser
            100                 105                 110

Gln

<210> SEQ ID NO 48
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 48

Met Ala Ser Thr Ser Gly Val Ser Asp Val Pro Arg Asp Leu Glu Val
 1               5                  10                  15

Val Ala Ala Thr Pro Thr Ser Leu Leu Ile Ser Trp Asp Ala Pro Ala
                20                  25                  30

Val Pro Val Ser Lys Tyr Val Ile Tyr Tyr Trp Pro Gly Ala Leu Ile
                35                  40                  45

Ser Ser Met Gln Ala Phe Lys Val Pro Gly Ser Lys Ser Thr Ala Thr
         50                  55                  60

Ile Ser Gly Leu Lys Pro Gly Val Leu Tyr Ser Ile Val Val Asp Ala
 65                 70                  75                  80

Leu Thr Gly Asp Gly Gln Gly Ser Tyr Val Trp Asp Pro Ile Thr Ile
                    85                  90                  95

Thr Tyr Arg Thr Glu Gly Ser Gly Ser
            100                 105

<210> SEQ ID NO 49
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 49

Met Ala Ser Thr Ser Gly Val Ser Asp Val Pro Arg Asp Leu Glu Val
 1               5                  10                  15

Val Ala Ala Thr Pro Thr Ser Leu Leu Ile Ser Trp Asp Ala Pro Ala
                20                  25                  30

Val Thr Val His Ser Tyr Tyr Ile Thr Tyr Gln Glu Leu Gln His His
                35                  40                  45

Ser Val Pro Gln Gly Phe Gln Val Pro Gly Ser Lys Ser Thr Ala Thr
         50                  55                  60

Ile Ser Gly Leu Lys Pro Gly Val Ala Tyr Gln Ile Ala Val Tyr Ala
 65                 70                  75                  80

Phe Thr Gly Pro Gly Leu Pro Pro Ser Asp Ala Pro Ile Val Ile
                    85                  90                  95

Tyr Tyr Arg Thr Glu Gly Ser Gly Ser
```

-continued

```
<210> SEQ ID NO 50
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 50

Met Ala Ser Thr Ser Gly
1               5

<210> SEQ ID NO 51
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 51

Pro Val Gln Glu Phe Thr Val Pro Gly Ser Lys Ser Thr Ala Thr Ile
1               5                   10                  15

Ser Gly Leu Lys
            20

<210> SEQ ID NO 52
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 52

Thr Ile Thr Val Tyr Ala Val Thr Gly Arg Gly Asp Ser Pro Ala Ser
1               5                   10                  15

Ser Lys Pro Ile Ser Ile Asn Tyr Arg Thr
            20                  25

<210> SEQ ID NO 53
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 53

Met Gly Glu Val Val Ala Ala Thr Pro Thr Ser Leu Leu Ile Ser
1               5                   10                  15

<210> SEQ ID NO 54
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 54

Pro His Phe Pro Thr Arg Tyr Tyr Arg Ile Thr Tyr Gly Glu Thr Gly
1               5                   10                  15

Gly Asn Ser

<210> SEQ ID NO 55
<211> LENGTH: 23
<212> TYPE: PRT
```

<213> ORGANISM: Homo sapiens

<400> SEQUENCE: 55

Pro Thr Ser Leu Leu Ile Ser Trp Asp Ala Pro Ala Val Thr Val Arg
1               5                   10                  15

Tyr Tyr Arg Ile Thr Tyr Gly
            20

<210> SEQ ID NO 56
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 56

Pro Thr Ser Leu Leu Ile Ser Trp Ser Ala Arg Leu Lys Val Ala Arg
1               5                   10                  15

Tyr Tyr Arg Ile Thr Tyr Gly
            20

<210> SEQ ID NO 57
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 57

Pro Thr Ser Leu Leu Ile Ser Trp Arg His Pro His Phe Pro Thr Arg
1               5                   10                  15

Tyr Tyr Arg Ile Thr Tyr Gly
            20

<210> SEQ ID NO 58
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 58

Pro Thr Ser Leu Leu Ile Ser Trp Asp Ala Pro Ala Val Thr Val Arg
1               5                   10                  15

Tyr Tyr Arg Ile Thr Tyr Gly
            20

<210> SEQ ID NO 59
<211> LENGTH: 101
<212> TYPE: PRT
<213> ORGANISM: Homo sapiens

<400> SEQUENCE: 59

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Glu

```
                65                  70                  75                  80
Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 60
<211> LENGTH: 86
<212> TYPE: PRT
<213> ORGANISM: Homo sapiens

<400> SEQUENCE: 60

Glu Val Val Ala Ala Thr Pro Thr Ser Leu Leu Ile Ser Trp Asp Ala
1               5                   10                  15

Pro Ala Val Thr Val Arg Tyr Tyr Arg Ile Thr Tyr Gly Glu Thr Gly
                20                  25                  30

Gly Asn Ser Pro Val Gln Glu Phe Thr Val Pro Gly Ser Lys Ser Thr
            35                  40                  45

Ala Thr Ile Ser Gly Leu Lys Pro Gly Val Asp Tyr Thr Ile Thr Val
        50                  55                  60

Tyr Ala Val Thr Gly Arg Gly Asp Ser Pro Ala Ser Ser Lys Pro Ile
65                  70                  75                  80

Ser Ile Asn Tyr Arg Thr
                85

<210> SEQ ID NO 61
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 61

Gly Val Ser Asp Val Pro Arg Asp Leu Glu Val Val Ala Ala Thr Pro
1               5                   10                  15

Thr Ser Leu Leu Ile Ser Trp Ser Ala Arg Leu Lys Val Ala Arg Tyr
                20                  25                  30

Tyr Arg Ile Thr Tyr Gly Glu Thr Gly Gly Asn Ser Pro Val Gln Glu
            35                  40                  45

Phe Thr Val Pro Lys Asn Val Tyr Thr Ala Thr Ile Ser Gly Leu Lys
        50                  55                  60

Pro Gly Val Asp Tyr Thr Ile Thr Val Tyr Ala Val Thr Arg Phe Arg
65                  70                  75                  80

Asp Tyr Gln Pro Ile Ser Ile Asn Tyr Arg Thr Glu Ile Asp Lys Pro
                85                  90                  95

Ser Gln

<210> SEQ ID NO 62
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 62

Met Ala Ser Thr Ser Gly Val Ser Asp Val Pro Arg Asp Leu Glu Val
1               5                   10                  15

Val Ala Ala Thr Pro Thr Ser Leu Leu Ile Ser Trp Asp Ala Pro Ala
                20                  25                  30
```

```
Val Pro Val Ser Lys Tyr Val Ile Tyr Tyr Trp Pro Gly Ala Leu Ile
            35                  40                  45

Ser Ser Met Gln Ala Phe Lys Val Pro Gly Ser Lys Ser Thr Ala Thr
 50                  55                  60

Ile Ser Gly Leu Lys Pro Gly Val Leu Tyr Ser Ile Val Val Asp Ala
 65                  70                  75                  80

Leu Thr Gly Asp Gly Gln Gly Ser Tyr Val Trp Asp Pro Ile Thr Ile
                 85                  90                  95

Thr Tyr Arg Thr Glu Gly Ser Gly Ser His His His His His His
                100                 105                 110

<210> SEQ ID NO 63
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 63

Met Ala Ser Thr Ser Gly Val Ser Asp Val Pro Arg Asp Leu Glu Val
 1               5                  10                  15

Val Ala Ala Thr Pro Thr Ser Leu Leu Ile Ser Trp Asp Ala Pro Ala
                20                  25                  30

Val Thr Val His Ser Tyr Tyr Ile Thr Tyr Gln Glu Leu Gln His His
            35                  40                  45

Ser Val Pro Gln Gly Phe Gln Val Pro Gly Ser Lys Ser Thr Ala Thr
 50                  55                  60

Ile Ser Gly Leu Lys Pro Gly Val Ala Tyr Gln Ile Ala Val Tyr Ala
 65                  70                  75                  80

Phe Thr Gly Pro Gly Leu Pro Pro Ser Asp Ala Pro Ile Val Ile
                 85                  90                  95

Tyr Tyr Arg Thr Glu Gly Ser Gly Ser His His His His His His
                100                 105                 110

<210> SEQ ID NO 64
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 64

Met Ala Ser Thr Ser Gly Ser His Tyr Tyr Lys Gly Thr Ala Asp
 1               5                  10                  15

Leu Glu Val Val Ala Ala Thr Pro Thr Ser Leu Leu Ile Ser Trp Pro
                20                  25                  30

Pro Pro Tyr Tyr Val Glu Gly Val Thr Val Phe Arg Ile Thr Tyr Gly
            35                  40                  45

Glu Thr Gly Gly Asn Ser Pro Val Gln Glu Phe Thr Val Pro Tyr Trp
 50                  55                  60

Thr Glu Thr Ala Thr Ile Ser Gly Leu Lys Pro Gly Val Asp Tyr Thr
 65                  70                  75                  80

Ile Thr Val Tyr Ala Glu Met Tyr Pro Gly Ser Pro Trp Ala Gly Gln
                 85                  90                  95

Val Met Asp Ile Gln Pro Ile Ser Ile Asn Tyr Arg Thr Glu Gly Ser
                100                 105                 110

Gly Ser
```

```
<210> SEQ ID NO 65
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 65

Met Ala Ser Thr Ser Gly Val Ser Asp Val Pro Arg Asp Leu Glu Val
1               5                   10                  15

Val Ala Ala Thr Pro Thr Ser Leu Leu Ile Ser Trp Asp Ala Pro Ala
            20                  25                  30

Val Thr Val Asn Asn Tyr Arg Ile Thr Tyr Gln Pro Leu Leu Gln Gly
        35                  40                  45

Ser Ser Ile Gln His Phe Asp Val Pro Gly Ser Lys Ser Thr Ala Thr
    50                  55                  60

Ile Ser Gly Leu Lys Pro Gly Val Gly Tyr Gln Ile Thr Val Tyr Ala
65                  70                  75                  80

Ser Thr Tyr Thr His Ser Lys Ala Tyr Tyr Ser Leu Pro Ile Ser Ile
                85                  90                  95

Tyr Tyr Arg Thr Glu Gly Ser Gly Ser
            100                 105

<210> SEQ ID NO 66
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 66

Met Gly Val Ser Asp Val Pro Arg Asp Leu Glu Val Val Ala Ala Thr
1               5                   10                  15

Pro Thr Ser Leu Leu Ile Ser Trp Lys Tyr Pro Tyr Glu Thr Ile Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Tyr Arg Ser Thr Ala Thr Ile Ser Gly Leu
    50                  55                  60

Lys Pro Gly Val Asp Tyr Thr Ile Thr Val Tyr Ala Val Glu Ala Ser
65                  70                  75                  80

Ala Pro Tyr Ser Asp Gly Gly Ser Pro Ile Ser Ile Asn Tyr Arg Thr
                85                  90                  95

Glu Ile Asp Lys Pro Ser Gln
            100

<210> SEQ ID NO 67
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 67

Met Gly Val Ser Asp Val Pro Arg Asp Leu Glu Val Val Ala Ala Thr
1               5                   10                  15

Pro Thr Ser Leu Leu Ile Ser Trp Ser Arg Pro Lys Gly Ser Ile Lys
            20                  25                  30
```

Tyr Tyr Arg Ile Thr Tyr Gly Glu Thr Gly Gly Asn Ser Pro Val Gln
            35                  40                  45

Glu Phe Thr Val Pro Asn Ser Gln Tyr Thr Ala Thr Ile Ser Gly Leu
        50                  55                  60

Lys Pro Gly Val Asp Tyr Thr Ile Thr Val Tyr Ala Val Tyr Gly Tyr
65                  70                  75                  80

Pro Tyr Gln Glu Pro His Tyr Tyr Pro Ile Ser Ile Asn Tyr Arg Thr
                85                  90                  95

Glu Ile Asp Lys Pro Ser Gln
            100

<210> SEQ ID NO 68
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 68

Met Gly Val Ser Asp Val Pro Arg Asp Leu Glu Val Val Ala Thr
1               5                   10                  15

Pro Thr Ser Leu Leu Ile Ser Trp Asp Gly Pro Lys Tyr Tyr Val Lys
            20                  25                  30

Tyr Tyr Arg Ile Thr Tyr Gly Glu Thr Gly Gly Asn Ser Pro Val Gln
            35                  40                  45

Glu Phe Thr Val Pro Arg Thr Asp His Thr Ala Thr Ile Ser Gly Leu
        50                  55                  60

Lys Pro Gly Val Asp Tyr Thr Ile Thr Val Tyr Ala Val Lys Gly Gln
65                  70                  75                  80

Tyr Gly Pro Tyr Tyr Gly Ser Arg Pro Ile Ser Ile Asn Tyr Arg Thr
                85                  90                  95

Glu Ile Asp Lys Pro Ser Gln
            100

<210> SEQ ID NO 69
<211> LENGTH: 103
<212> TYPE: PRT
<213> ORGANISM: Artificial Sequence
<220> FEATURE:
<223> OTHER INFORMATION: Synthetic polypeptide

<400> SEQUENCE: 69

Met Gly Val Ser Asp Val Pro Arg Asp Leu Glu Val Val Ala Ala Thr
1               5                   10                  15

Pro Thr Ser Leu Leu Ile Ser Trp Ser Gln Pro Gly Arg Tyr Val Lys
            20                  25                  30

Tyr Tyr Arg Ile Thr Tyr Gly Glu Thr Gly Gly Asn Ser Pro Val Gln
            35                  40                  45

Glu Phe Thr Val Pro Asn Asp Thr Tyr Thr Ala Thr Ile Ser Gly Leu
        50                  55                  60

Lys Pro Gly Val Asp Tyr Thr Ile Thr Val Tyr Ala Val Tyr Gly Lys
65                  70                  75                  80

Tyr Gly Pro Tyr Tyr Gly Tyr Asp Pro Ile Ser Ile Asn Tyr Arg Thr
                85                  90                  95

Glu Ile Asp Lys Pro Ser Gln
            100

<210> SEQ ID NO 70

-continued

```
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 70

Met Ala Ser Thr Ser Gly Ser Thr His Tyr Tyr Lys Gly Thr Ala Asp
1               5                   10                  15

Leu Glu Val Val Ala Ala Thr Pro Thr Ser Leu Leu Ile Ser Trp Pro
                20                  25                  30

Pro Pro Tyr Tyr Val Glu Gly Val Thr Val Phe Arg Ile Thr Tyr Gly
                35                  40                  45

Glu Thr Gly Gly Asn Ser Pro Val Gln Glu Phe Thr Val Pro Tyr Trp
            50                  55                  60

Thr Glu Thr Ala Thr Ile Ser Gly Leu Lys Pro Gly Val Asp Tyr Thr
65                  70                  75                  80

Ile Thr Val Tyr Ala Glu Met Tyr Pro Gly Ser Pro Trp Ala Gly Gln
                85                  90                  95

Val Met Asp Ile Gln Pro Ile Ser Ile Asn Tyr Arg Thr Glu Gly Ser
                100                 105                 110

Gly Ser His His His His His His
                115                 120

<210> SEQ ID NO 71
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 71

Met Ala Ser Thr Ser Gly Val Ser Asp Val Pro Arg Asp Leu Glu Val
1               5                   10                  15

Val Ala Ala Thr Pro Thr Ser Leu Leu Ile Ser Trp Asp Ala Pro Ala
                20                  25                  30

Val Thr Val Asn Asn Tyr Arg Ile Thr Tyr Gln Pro Leu Leu Gln Gly
                35                  40                  45

Ser Ser Ile Gln His Phe Asp Val Pro Gly Ser Lys Ser Thr Ala Thr
            50                  55                  60

Ile Ser Gly Leu Lys Pro Gly Val Gly Tyr Gln Ile Thr Val Tyr Ala
65                  70                  75                  80

Ser Thr Tyr Thr His Ser Lys Ala Tyr Tyr Ser Leu Pro Ile Ser Ile
                85                  90                  95

Tyr Tyr Arg Thr Glu Gly Ser Gly Ser His His His His His His
                100                 105                 110

<210> SEQ ID NO 72
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 72

Met Gly Val Ser Asp Val Pro Arg Asp Leu Glu Val Val Ala Ala Thr
1               5                   10                  15

Pro Thr Ser Leu Leu Ile Ser Trp Lys Tyr Pro Tyr Glu Thr Ile Ser
                20                  25                  30
```

-continued

```
Tyr Tyr Arg Ile Thr Tyr Gly Glu Thr Gly Gly Asn Ser Pro Val Gln
            35                  40                  45

Glu Phe Thr Val Pro Tyr Arg Ser Thr Ala Thr Ile Ser Gly Leu
 50                  55                  60

Lys Pro Gly Val Asp Tyr Thr Ile Thr Val Tyr Ala Val Glu Ala Ser
 65                  70                  75                  80

Ala Pro Tyr Ser Asp Gly Gly Ser Pro Ile Ser Ile Asn Tyr Arg Thr
                85                  90                  95

Glu Ile Asp Lys Pro Ser Gln His His His His His His
            100                 105
```

<210> SEQ ID NO 73
<211> LENGTH: 101
<212> TYPE: PRT
<213> ORGANISM: Artificial Sequence
<220> FEATURE:
<223> OTHER INFORMATION: Northwest Binder
<220> FEATURE:
<221> NAME/KEY: MISC_FEATURE
<223> OTHER INFORMATION: X1-X34 can be modified by deletion,
      substitution (with any amino acid), or insertion (with any amino
      acid)
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 73

```
Val Ser Asp Val Pro Arg Asp Leu Glu Val Val Ala Ala Thr Pro Thr
 1               5                  10                  15

Ser Leu Leu Ile Ser Trp Xaa Xaa Xaa Xaa Xaa Xaa Xaa Xaa Xaa Tyr
                20                  25                  30

Xaa Ile Xaa Tyr Gly Glu Thr Gly Gly Asn Ser Pro Val Gln Xaa Phe
            35                  40                  45
```

Xaa Val Xaa Xaa Xaa Xaa Xaa Thr Ala Thr Ile Ser Gly Leu Lys Pro
    50                  55                  60

Gly Val Asp Tyr Thr Ile Xaa Val Xaa Ala Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 74
<211> LENGTH: 101
<212> TYPE: PRT
<213> ORGANISM: Artificial Sequence
<220> FEATURE:
<223> OTHER INFORMATION: Northeast Binder
<220> FEATURE:
<221> NAME/KEY: MISC_FEATURE
<223> OTHER INFORMATION: X1-X35 can be modified by deletion,
      substitution (with any amino acid), or insertion (with any amino
      acid)
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (52)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid

<400> SEQUENCE: 74

Val Ser Xaa Xaa Xaa Xaa Xaa Leu Xaa Val Val Ala Ala Thr Pro Thr
1               5                   10                  15

Ser Leu Xaa Ile Xaa Trp Xaa Xaa Xaa Xaa Xaa Xaa Xaa Xaa Tyr
            20                  25                  30

Arg Ile Thr Tyr Gly Glu Thr Gly Gly Asn Ser Pro Val Gln Glu Phe
            35                  40                  45

Thr Val Pro Xaa Xaa Xaa Xaa Ala Xaa Ile Xaa Gly Leu Lys Pro
            50                  55                  60

Gly Val Asp Tyr Thr Ile Thr Val Tyr Ala Val Xaa Xaa Xaa Xaa Xaa
65                  70                  75                  80

Xaa Xaa Xaa Xaa Xaa Xaa Pro Ile Ser Ile Asn Tyr Arg Thr Glu Ile

-continued

```
                85                  90                  95

Asp Lys Pro Ser Gln
            100

<210> SEQ ID NO 75
<211> LENGTH: 101
<212> TYPE: PRT
<213> ORGANISM: Artificial Sequence
<220> FEATURE:
<223> OTHER INFORMATION: West Side Binder
<220> FEATURE:
<221> NAME/KEY: MISC_FEATURE
<223> OTHER INFORMATION: X1-X32 can be modified by deletion,
      substitution (with any amino acid), or insertion (with any amino
      acid)
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (77)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid

<400> SEQUENCE: 75

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Xaa Phe
```

```
            35                  40                  45
Xaa Val Pro Gly Ser Lys Ser Thr Ala Thr Ile Ser Gly Leu Lys Pro
        50                  55                  60
Gly Val Asp Tyr Xaa Ile Xaa Val Xaa Ala Xaa Thr Xaa Xaa Xaa Xaa
 65                  70                  75                  80

Xaa Xaa Xaa Xaa Xaa Xaa Ile Xaa Ile Xaa Tyr Arg Thr Glu Ile
                85                  90                  95

Asp Lys Pro Ser Gln
            100

<210> SEQ ID NO 76
<211> LENGTH: 101
<212> TYPE: PRT
<213> ORGANISM: Artificial Sequence
<220> FEATURE:
<223> OTHER INFORMATION: South-Front Binder
<220> FEATURE:
<221> NAME/KEY: MISC_FEATURE
<223> OTHER INFORMATION: X1-X22 can be modified by deletion,
      substitution (with any amino acid), or insertion (with any amino
      acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (40)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(65)
<223> OTHER INFORMATION: Xaa can be any naturally occurring amino acid

<400> SEQUENCE: 76

Val Ser Asp Val Pro Arg Asp Leu Glu Val Val Ala Ala Xaa Xaa Xaa
 1               5                  10                  15

Xaa Leu Xaa Ile Ser Trp Asp Ala Pro Ala Val Thr Val Arg Tyr Tyr
                20                  25                  30

Arg Ile Thr Tyr Gly Glu Thr Xaa Xaa Xaa Xaa Xaa Xaa Xaa Xaa Phe
                35                  40                  45

Xaa Val Xaa Gly Ser Lys Ser Xaa Ala Xaa Ile Xaa Xaa Leu Xaa Xaa
        50                  55                  60

Xaa Val Asp Tyr Thr Ile Thr Val Tyr Ala Val Thr Gly Arg Gly Asp
 65                  70                  75                  80
```

```
Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 77
<211> LENGTH: 101
<212> TYPE: PRT
<213> ORGANISM: Artificial Sequence
<220> FEATURE:
<223> OTHER INFORMATION: AG Strand Binder
<220> FEATURE:
<221> NAME/KEY: MISC_FEATURE
<223> OTHER INFORMATION: X1-X29 can be modified by deletion,
      substitution (with any amino acid), or insertion (with any amino
      acid
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (84)..(89)
<223> OTHER INFORMATION: Xaa can be any naturally occurring amino acid
<220> FEATURE:
<221> NAME/KEY: misc_feature
<222> LOCATION: (91)..(97)
<223> OTHER INFORMATION: Xaa can be any naturally occurring amino acid

<400> SEQUENCE: 77

Xaa Xaa Xaa Xaa Xaa Xaa Xaa Leu Xaa Val Xaa Xaa Xaa Xaa Xaa Xaa
1               5                   10                  15

Xaa Leu Xaa Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Xaa Xaa Xaa Xaa Xaa Xaa Ile Xaa Xaa Xaa Xaa Xaa Xaa
                85                  90                  95

Xaa Lys Pro Ser Gln
            100

<210> SEQ ID NO 78
<211> LENGTH: 101
<212> TYPE: PRT
<213> ORGANISM: Artificial Sequence
<220> FEATURE:
<223> OTHER INFORMATION: SouthWest Binder
<220> FEATURE:
<221> NAME/KEY: MISC_FEATURE
<223> OTHER INFORMATION: X1-X27 can be modified by deletion,
      substitution (with any amino acid), or insertion (with any amino
      acid).
```

```
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(97)
<223> OTHER INFORMATION: Xaa can be any naturally occurring amino acid

<400> SEQUENCE: 78

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Xaa Ile Xaa Tyr Xaa Xaa Xaa Xaa Xaa Xaa Xaa Xaa Gln Xaa Phe
        35                  40                  45

Thr Val Pro Gly Ser Lys Ser Thr Ala Thr Ile Ser Gly Leu Xaa Xaa
    50                  55                  60

Xaa Xaa Xaa Tyr Xaa Ile Xaa Val Tyr Ala Val Thr Gly Arg Gly Asp
65                  70                  75                  80

Ser Pro Ala Ser Ser Lys Pro Ile Xaa Ile Xaa Xaa Xaa Xaa Xaa
                85                  90                  95

Xaa Lys Pro Ser Gln
            100

<210> SEQ ID NO 79
<211> LENGTH: 101
<212> TYPE: PRT
<213> ORGANISM: Artificial Sequence
<220> FEATURE:
<223> OTHER INFORMATION: Classic NP
<220> FEATURE:
<221> NAME/KEY: MISC_FEATURE
<223> OTHER INFORMATION: X1-X23 can be modified by substitution (with
      any amino acid)
<220> FEATURE:
<221> NAME/KEY: misc_feature
<222> LOCATION: (23)..(30)
<223> OTHER INFORMATION: Xaa can be any naturally occurring amino acid
<220> FEATURE:
<221> NAME/KEY: misc_feature
<222> LOCATION: (52)..(55)
<223> OTHER INFORMATION: Xaa can be any naturally occurring amino acid
```

<220> FEATURE:
<221> NAME/KEY: misc_feature
<222> LOCATION: (76)..(86)
<223> OTHER INFORMATION: Xaa can be any naturally occurring amino acid

<400> SEQUENCE: 79

Val Ser Asp Val Pro Arg Asp Leu Glu Val Val Ala Ala Thr Pro Thr
1               5                   10                  15

Ser Leu Leu Ile Ser Trp Xaa Xaa Xaa Xaa Xaa Xaa Xaa Xaa Tyr Tyr
            20                  25                  30

Arg Ile Thr Tyr Gly Glu Thr Gly Gly Asn Ser Pro Val Gln Glu Phe
        35                  40                  45

Thr Val Pro Xaa Xaa Xaa Xaa Thr Ala Thr Ile Ser Gly Leu Lys Pro
    50                  55                  60

Gly Val Asp Tyr Thr Ile Thr Val Tyr Ala Val Xaa Xaa Xaa Xaa Xaa
65                  70                  75                  80

Xaa Xaa Xaa Xaa Xaa Xaa Pro Ile Ser Ile Asn Tyr Arg Thr Glu Ile
                85                  90                  95

Asp Lys Pro Ser Gln
            100

<210> SEQ ID NO 80
<211> LENGTH: 101
<212> TYPE: PRT
<213> ORGANISM: Artificial Sequence
<220> FEATURE:
<223> OTHER INFORMATION: WS1
<220> FEATURE:
<221> NAME/KEY: MISC_FEATURE
<223> OTHER INFORMATION: X1-X33 can be modified by substitution (with
      any other amino acid)
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid -continued

```
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid

<400> SEQUENCE: 80

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Xaa Phe
        35                  40                  45

Xaa Val Pro Gly Ser Lys Ser Thr Ala Thr Ile Ser Gly Leu Lys Pro
    50                  55                  60

Gly Val Asp Tyr Xaa Ile Xaa Val Xaa Ala Xaa Xaa Xaa Xaa Xaa
65                  70                  75                  80

Xaa Xaa Xaa Xaa Xaa Xaa Xaa Ile Xaa Ile Xaa Tyr Arg Thr Glu Ile
                85                  90                  95

Asp Lys Pro Ser Gln
            100

<210> SEQ ID NO 81
<211> LENGTH: 101
<212> TYPE: PRT
<213> ORGANISM: Artificial Sequence
<220> FEATURE:
<223> OTHER INFORMATION: WS2
<220> FEATURE:
<221> NAME/KEY: MISC_FEATURE
<223> OTHER INFORMATION: X1-X4, X15-X17, X29, X30 residues can be
      modified by substitution (with any amino acid)
<220> FEATURE:
<221> NAME/KEY: MISC_FEATURE
<223> OTHER INFORMATION: Remaining  X amino acid residues can be
      modified by deletion, substitution (with any amino acid), or
      insertion (with any amino acid).
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
```

```
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid

<400> SEQUENCE: 81

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Xaa Xaa Tyr
             20                  25                  30

Xaa Ile Xaa Tyr Xaa Xaa Xaa Xaa Xaa Xaa Xaa Xaa Gln Glu Phe
         35                  40                  45

Xaa Val Pro Gly Ser Lys Ser Thr Ala Thr Ile Ser Gly Leu Lys Pro
     50                  55                  60

Gly Val Asp Tyr Xaa Ile Xaa Val Xaa Ala Val Xaa Xaa Xaa Xaa Xaa
 65                  70                  75                  80

Xaa Xaa Xaa Xaa Xaa Xaa Pro Ile Xaa Ile Xaa Tyr Arg Thr Glu Ile
                 85                  90                  95

Asp Lys Pro Ser Gln
            100

<210> SEQ ID NO 82
<211> LENGTH: 101
<212> TYPE: PRT
<213> ORGANISM: Artificial Sequence
<220> FEATURE:
<223> OTHER INFORMATION: WS3
<220> FEATURE:
<221> NAME/KEY: MISC_FEATURE
<223> OTHER INFORMATION: X1-X20 can be modified by deletion,
      substitution (with any amino acid), or insertion (with any amino
      acid)
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid

<400> SEQUENCE: 82

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
             20                  25                  30

Arg Ile Thr Tyr Xaa Xaa Xaa Xaa Xaa Xaa Xaa Xaa Gln Glu Phe
         35                  40                  45

Thr Val Pro Gly Ser Lys Ser Thr Ala Thr Ile Ser Gly Leu Lys Pro
     50                  55                  60

Gly Val Asp Tyr Thr Ile Thr Val Tyr Ala Val Xaa Xaa Xaa Xaa Xaa
 65                  70                  75                  80

Xaa Xaa Xaa Xaa Xaa Xaa Pro Ile Ser Ile Asn Tyr Arg Thr Glu Ile
                 85                  90                  95

Asp Lys Pro Ser Gln
```

```
                            100

<210> SEQ ID NO 83
<211> LENGTH: 101
<212> TYPE: PRT
<213> ORGANISM: Artificial Sequence
<220> FEATURE:
<223> OTHER INFORMATION: Front 1
<220> FEATURE:
<221> NAME/KEY: MISC_FEATURE
<223> OTHER INFORMATION: X1, X13, X20, X21 residues can be modified by
      substitution (with any amino acid)
<220> FEATURE:
<221> NAME/KEY: MISC_FEATURE
<223> OTHER INFORMATION: Remaining  X amino acid residues can be
      modified by deletion, substitution (with any amino acid), or
      insertion (with any amino acid).
<220> FEATURE:
<221> NAME/KEY: misc_feature
<222> LOCATION: (36)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(66)
<223> OTHER INFORMATION: Xaa can be any naturally occurring amino acid

<400> SEQUENCE: 83

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Xaa Xaa Xaa Xaa Xaa Xaa Xaa Xaa Xaa Xaa Xaa Xaa Phe
        35                  40                  45

Xaa Val Xaa Xaa Xaa Xaa Xaa Xaa Ala Xaa Ile Xaa Gly Leu Xaa Xaa
    50                  55                  60

Xaa Xaa Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 84
<211> LENGTH: 101
<212> TYPE: PRT
<213> ORGANISM: Artificial Sequence
<220> FEATURE:
<223> OTHER INFORMATION: Front 2
<220> FEATURE:
<221> NAME/KEY: MISC_FEATURE
<223> OTHER INFORMATION: X1-X25 can be modified by substitution (with
      any amino acid)
<220> FEATURE:
<221> NAME/KEY: misc_feature
```

```
<222> LOCATION: (36)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(66)
<223> OTHER INFORMATION: Xaa can be any naturally occurring amino acid

<400> SEQUENCE: 84

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Xaa Xaa Xaa Xaa Xaa Xaa Xaa Xaa Xaa Xaa Xaa Xaa Phe
        35                  40                  45

Xaa Val Xaa Xaa Xaa Xaa Xaa Ala Xaa Ile Xaa Gly Leu Xaa Xaa
    50                  55                  60

Xaa Xaa Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 85
<211> LENGTH: 101
<212> TYPE: PRT
<213> ORGANISM: Artificial Sequence
<220> FEATURE:
<223> OTHER INFORMATION: Back 1
<220> FEATURE:
<221> NAME/KEY: MISC_FEATURE
<223> OTHER INFORMATION: X8-X12 and X26, X27 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (64)..(67)
<223> OTHER INFORMATION: Xaa can be any naturally occurring amino acid
<220> FEATURE:
<221> NAME/KEY: misc_feature
<222> LOCATION: (81)..(87)
<223> OTHER INFORMATION: Xaa can be any naturally occurring amino acid
<220> FEATURE:
```

```
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(101)
<223> OTHER INFORMATION: Xaa can be any naturally occurring amino acid

<400> SEQUENCE: 85

Xaa Xaa Xaa Xaa Xaa Xaa Xaa Leu Xaa Xaa Xaa Xaa Xaa Xaa Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Xaa
        50                  55                  60

Xaa Xaa Xaa Tyr Thr Ile Thr Val Tyr Ala Val Thr Gly Arg Gly Glu
65                  70                  75                  80

Xaa Xaa Xaa Xaa Xaa Xaa Ile Xaa Ile Xaa Tyr Xaa Xaa Xaa Xaa
                85                  90                  95

Xaa Xaa Xaa Xaa Xaa
            100

<210> SEQ ID NO 86
<211> LENGTH: 101
<212> TYPE: PRT
<213> ORGANISM: Artificial Sequence
<220> FEATURE:
<223> OTHER INFORMATION: Back 2
<220> FEATURE:
<221> NAME/KEY: MISC_FEATURE
<223> OTHER INFORMATION: X1-X36 can be modified by substitution (with
      any amino acid)
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(15)
<223> OTHER INFORMATION: Xaa can be any naturally occurring amino acid
<220> FEATURE:
<221> NAME/KEY: misc_feature
<222> LOCATION: (64)..(67)
<223> OTHER INFORMATION: Xaa can be any naturally occurring amino acid
<220> FEATURE:
<221> NAME/KEY: misc_feature
<222> LOCATION: (81)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(101)
<223> OTHER INFORMATION: Xaa can be any naturally occurring amino acid

<400> SEQUENCE: 86

Xaa Xaa Xaa Xaa Xaa Xaa Xaa Leu Xaa Xaa Xaa Xaa Xaa Xaa Thr
1               5                   10                  15
```

-continued

```
Ser Leu Leu Ile Ser Trp Asp Ala Pro Ala Val Thr Val Arg Tyr Tyr
         20                  25                  30

Arg Ile Thr Tyr Gly Glu Thr Gly Asn Ser Pro Val Gln Glu Phe
         35                  40                  45

Thr Val Pro Gly Ser Lys Ser Thr Ala Thr Ile Ser Gly Leu Lys Xaa
 50                  55                  60

Xaa Xaa Xaa Tyr Thr Ile Thr Val Tyr Ala Val Thr Gly Arg Gly Glu
 65                  70                  75                  80

Xaa Xaa Xaa Xaa Xaa Xaa Xaa Ile Xaa Ile Xaa Tyr Xaa Xaa Xaa Xaa
                 85                  90                  95

Xaa Xaa Xaa Xaa Xaa
            100

<210> SEQ ID NO 87
<211> LENGTH: 101
<212> TYPE: PRT
<213> ORGANISM: Artificial Sequence
<220> FEATURE:
<223> OTHER INFORMATION: SP1
<220> FEATURE:
<221> NAME/KEY: MISC_FEATURE
<223> OTHER INFORMATION: X1-X7 and X18-X30 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (37)..(46)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(97)
<223> OTHER INFORMATION: Xaa can be any naturally occurring amino acid

<400> SEQUENCE: 87

Val Ser Asp Val Pro Arg Asp Leu Glu Val Xaa Xaa Ala Xaa Xaa Xaa
```

```
                1               5                   10                  15
Xaa Leu Xaa Ile Ser Trp Asp Ala Pro Ala Val Thr Val Arg Tyr Tyr
                    20                  25                  30
Arg Ile Thr Tyr Xaa Xaa Xaa Xaa Xaa Xaa Xaa Xaa Xaa Glu Phe
                    35                  40                  45
Thr Val Pro Gly Ser Lys Ser Thr Ala Thr Ile Xaa Xaa Leu Xaa Xaa
        50                  55                  60
Xaa Xaa Xaa Tyr Xaa Ile Thr Val Tyr Ala Val Thr Gly Arg Gly Glu
65                  70                  75                  80
Ser Pro Ala Ser Ser Lys Pro Ile Ser Ile Xaa Tyr Xaa Thr Xaa Xaa
                85                  90                  95
Xaa Lys Pro Ser Gln
            100

<210> SEQ ID NO 88
<211> LENGTH: 101
<212> TYPE: PRT
<213> ORGANISM: Artificial Sequence
<220> FEATURE:
<223> OTHER INFORMATION: SP2
<220> FEATURE:
<221> NAME/KEY: MISC_FEATURE
<223> OTHER INFORMATION: X1-X7 and X19-X31 Highlighted residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (37)..(47)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(97)
<223> OTHER INFORMATION: Xaa can be any naturally occurring amino acid

<400> SEQUENCE: 88
```

```
Val Ser Asp Val Pro Arg Asp Leu Glu Val Xaa Xaa Ala Xaa Xaa Xaa
1               5                   10                  15

Xaa Leu Xaa Ile Ser Trp Asp Ala Pro Ala Val Thr Val Arg Tyr Tyr
            20                  25                  30

Arg Ile Thr Tyr Xaa Xaa Xaa Xaa Xaa Xaa Xaa Xaa Xaa Phe
                35                  40                  45

Thr Val Pro Gly Ser Lys Ser Thr Ala Thr Ile Xaa Xaa Leu Xaa Xaa
    50                  55                  60

Xaa Xaa Xaa Tyr Xaa Ile Thr Val Tyr Ala Val Thr Gly Arg Gly Glu
65                  70                  75                  80

Ser Pro Ala Ser Ser Lys Pro Ile Ser Ile Xaa Tyr Xaa Thr Xaa Xaa
                85                  90                  95

Xaa Lys Pro Ser Gln
            100
```

<210> SEQ ID NO 89
<211> LENGTH: 101
<212> TYPE: PRT
<213> ORGANISM: Artificial Sequence
<220> FEATURE:
<223> OTHER INFORMATION: SP3
<220> FEATURE:
<221> NAME/KEY: MISC_FEATURE
<223> OTHER INFORMATION: X1-X7 and X17-X29 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (95)..(97)
<223> OTHER INFORMATION: Xaa can be any naturally occurring amino acid

<400> SEQUENCE: 89

```
Val Ser Asp Val Pro Arg Asp Leu Glu Val Xaa Xaa Ala Xaa Xaa Xaa
1               5                   10                  15

Xaa Leu Xaa Ile Ser Trp Asp Ala Pro Ala Val Thr Val Arg Tyr Tyr
            20                  25                  30

Arg Ile Thr Tyr Xaa Xaa Xaa Xaa Xaa Xaa Xaa Xaa Gln Glu Phe
            35                  40                  45

Thr Val Pro Gly Ser Lys Ser Thr Ala Thr Ile Xaa Xaa Leu Xaa Xaa
50                      55                  60

Xaa Xaa Xaa Tyr Xaa Ile Thr Val Tyr Ala Val Thr Gly Arg Gly Glu
65              70                  75                  80

Ser Pro Ala Ser Ser Lys Pro Ile Ser Ile Xaa Tyr Xaa Thr Xaa Xaa
                85                  90                  95

Xaa Lys Pro Ser Gln
            100
```

<210> SEQ ID NO 90
<211> LENGTH: 101
<212> TYPE: PRT
<213> ORGANISM: Artificial Sequence
<220> FEATURE:
<223> OTHER INFORMATION: LI-3 (a)
<220> FEATURE:
<221> NAME/KEY: MISC_FEATURE
<223> OTHER INFORMATION: X1-X7 can be modified by deletion, substitution
      (with any amino acid), or insertion (with any amino acid)
<220> FEATURE:
<221> NAME/KEY: misc_feature
<222> LOCATION: (77)..(83)
<223> OTHER INFORMATION: Xaa can be any naturally occurring amino acid

<400> SEQUENCE: 90

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
50                      55                  60

Gly Val Asp Tyr Thr Ile Thr Val Tyr Ala Val Thr Xaa Xaa Xaa Xaa
65              70                  75                  80

Xaa Xaa Xaa Ser Ser Lys Pro Ile Ser Ile Asn Tyr Arg Thr Glu Ile
                85                  90                  95

Asp Lys Pro Ser Gln
            100
```

<210> SEQ ID NO 91
<211> LENGTH: 101
<212> TYPE: PRT
<213> ORGANISM: Artificial Sequence
<220> FEATURE:
<223> OTHER INFORMATION: WS-LI1
<220> FEATURE:
<221> NAME/KEY: MISC_FEATURE
<223> OTHER INFORMATION: X1-X14 can be modified by deletion,
      substitution (with any amino acid), or insertion (with any amino
      acid)
<220> FEATURE:
<221> NAME/KEY: misc_feature
<222> LOCATION: (39)..(45)
<223> OTHER INFORMATION: Xaa can be any naturally occurring amino acid
<220> FEATURE:
<221> NAME/KEY: misc_feature

```
<222> LOCATION: (77)..(83)
<223> OTHER INFORMATION: Xaa can be any naturally occurring amino acid

<400> SEQUENCE: 91

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Xaa Xaa Xaa Xaa Xaa Xaa Xaa Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Xaa Xaa Xaa Xaa
65                  70                  75                  80

Xaa Xaa Xaa Ser Ser Lys Pro Ile Ser Ile Asn Tyr Arg Thr Glu Ile
            85                  90                  95

Asp Lys Pro Ser Gln
            100

<210> SEQ ID NO 92
<211> LENGTH: 101
<212> TYPE: PRT
<213> ORGANISM: Artificial Sequence
<220> FEATURE:
<223> OTHER INFORMATION: LI-S9
<220> FEATURE:
<221> NAME/KEY: MISC_FEATURE
<223> OTHER INFORMATION: X1-X12 can be modified by deletion,
      substitution (with any amino acid), or insertion (with any amino
      acid)
<220> FEATURE:
<221> NAME/KEY: misc_feature
<222> LOCATION: (39)..(45)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid

<400> SEQUENCE: 92

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Xaa Xaa Xaa Xaa Xaa Xaa Xaa Gln Glu Phe
        35                  40                  45

Thr Val Pro Gly Ser Lys Ser Thr Ala Thr Ile Ser Gly Leu Xaa Xaa
    50                  55                  60

Xaa Xaa Xaa Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
            85                  90                  95

Asp Lys Pro Ser Gln
            100

<210> SEQ ID NO 93
<211> LENGTH: 101
<212> TYPE: PRT
<213> ORGANISM: Artificial Sequence
<220> FEATURE:
<223> OTHER INFORMATION: SouthFront
<220> FEATURE:
<221> NAME/KEY: MISC_FEATURE
```

```
<223> OTHER INFORMATION: X5 and X14-X19 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (14)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (40)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(61)
<223> OTHER INFORMATION: Xaa can be any naturally occurring amino acid
<220> FEATURE:
<221> NAME/KEY: misc_feature
<222> LOCATION: (63)..(66)
<223> OTHER INFORMATION: Xaa can be any naturally occurring amino acid

<400> SEQUENCE: 93

Val Ser Asp Val Pro Arg Asp Leu Glu Val Val Ala Ala Xaa Xaa Xaa
1               5                   10                  15

Xaa Leu Xaa Ile Ser Trp Asp Ala Pro Ala Val Thr Val Arg Tyr Tyr
            20                  25                  30

Arg Ile Thr Tyr Gly Glu Thr Xaa Xaa Xaa Xaa Xaa Xaa Xaa Xaa Phe
        35                  40                  45

Xaa Val Xaa Gly Ser Lys Ser Xaa Ala Xaa Ile Xaa Xaa Leu Xaa Xaa
    50                  55                  60

Xaa Xaa Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 94
<211> LENGTH: 101
<212> TYPE: PRT
<213> ORGANISM: Artificial Sequence
<220> FEATURE:
<223> OTHER INFORMATION: AG Strand
<220> FEATURE:
<221> NAME/KEY: MISC_FEATURE
<223> OTHER INFORMATION: X8-X13, X16, and X21-X24 residues can be
      modified by substitution (with any amino acid)
<220> FEATURE:
```

```
<221> NAME/KEY: MISC_FEATURE
<223> OTHER INFORMATION: Non-highlighted X amino acid residues can be
      modified by deletion, substitution (with any amino acid), or
      insertion (with any amino acid)
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(17)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (84)..(89)
<223> OTHER INFORMATION: Xaa can be any naturally occurring amino acid
<220> FEATURE:
<221> NAME/KEY: misc_feature
<222> LOCATION: (91)..(101)
<223> OTHER INFORMATION: Xaa can be any naturally occurring amino acid

<400> SEQUENCE: 94

Xaa Xaa Xaa Xaa Xaa Xaa Xaa Leu Xaa Val Xaa Xaa Xaa Xaa Xaa
1               5                   10                  15

Xaa Leu Xaa Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Glu
65                  70                  75                  80

Ser Pro Ala Xaa Xaa Xaa Xaa Xaa Ile Xaa Xaa Xaa Xaa Xaa
                85                  90                  95

Xaa Xaa Xaa Xaa Xaa
            100

<210> SEQ ID NO 95
<211> LENGTH: 101
<212> TYPE: PRT
<213> ORGANISM: Artificial Sequence
<220> FEATURE:
<223> OTHER INFORMATION: SouthWest
<220> FEATURE:
<221> NAME/KEY: MISC_FEATURE
<223> OTHER INFORMATION: X1, X2, X12, X18, X19, and X29 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
```

<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (63)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(101)
<223> OTHER INFORMATION: Xaa can be any naturally occurring amino acid

<400> SEQUENCE: 95

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Xaa Ile Xaa Tyr Xaa Xaa Xaa Xaa Xaa Xaa Xaa Xaa Gln Xaa Phe
        35                  40                  45

Thr Val Pro Gly Ser Lys Ser Thr Ala Thr Ile Ser Gly Leu Xaa Xaa
    50                  55                  60

Xaa Xaa Xaa Tyr Xaa Ile Xaa Val Tyr Ala Val Thr Gly Arg Gly Glu
65                  70                  75                  80

Ser Pro Ala Ser Ser Lys Pro Ile Xaa Ile Xaa Xaa Xaa Xaa Xaa
                85                  90                  95

Xaa Xaa Xaa Xaa Xaa
            100

<210> SEQ ID NO 96
<211> LENGTH: 101
<212> TYPE: PRT
<213> ORGANISM: Artificial Sequence
<220> FEATURE:
<223> OTHER INFORMATION: WS2'
<220> FEATURE:
<221> NAME/KEY: MISC_FEATURE
<223> OTHER INFORMATION: X1-X4, X15-X17, and X31 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature

```
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 96

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Xaa Phe
        35                  40                  45

Xaa Val Pro Gly Ser Lys Ser Thr Ala Thr Ile Ser Gly Leu Lys Pro
    50                  55                  60

Gly Val Asp Tyr Thr Ile Xaa Val Xaa Ala Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 97
<211> LENGTH: 101
<212> TYPE: PRT
<213> ORGANISM: Artificial Sequence
<220> FEATURE:
<223> OTHER INFORMATION: WS2'-CD
<220> FEATURE:
<221> NAME/KEY: MISC_FEATURE
<223> OTHER INFORMATION: X1-X3 and X14 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
```

```
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid

<400> SEQUENCE: 97

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Xaa Tyr
             20                  25                  30

Xaa Ile Xaa Tyr Xaa Xaa Xaa Xaa Xaa Xaa Xaa Xaa Gln Xaa Phe
         35                  40                  45

Xaa Val Pro Gly Ser Lys Ser Thr Ala Thr Ile Ser Gly Leu Lys Pro
     50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                 85                  90                  95

Asp Lys Pro Ser Gln
            100

<210> SEQ ID NO 98
<211> LENGTH: 101
<212> TYPE: PRT
<213> ORGANISM: Artificial Sequence
<220> FEATURE:
<223> OTHER INFORMATION: Front3
<220> FEATURE:
<221> NAME/KEY: MISC_FEATURE
<223> OTHER INFORMATION: X1 and X12-X18 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (36)..(38)
<223> OTHER INFORMATION: Xaa can be any naturally occurring amino acid
<220> FEATURE:
<221> NAME/KEY: misc_feature
<222> LOCATION: (40)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (63)..(66)
<223> OTHER INFORMATION: Xaa can be any naturally occurring amino acid

<400> SEQUENCE: 98

Val Ser Asp Val Pro Arg Asp Leu Glu Val Val Ala Ala Thr Pro Thr
```

```
                1               5                  10                 15
Ser Leu Leu Ile Ser Trp Asp Ala Pro Ala Val

```
<210> SEQ ID NO 100
<211> LENGTH: 101
<212> TYPE: PRT
<213> ORGANISM: Artificial Sequence
<220> FEATURE:
<223> OTHER INFORMATION: LI-S8
<220> FEATURE:
<221> NAME/KEY: MISC_FEATURE
<223> OTHER INFORMATION: X1-X7 can be modified by substitution (with any
      amino acid)
<220> FEATURE:
<221> NAME/KEY: misc_feature
<222> LOCATION: (39)..(45)
<223> OTHER INFORMATION: Xaa can be any naturally occurring amino acid

<400> SEQUENCE: 100

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Xaa Xaa Xaa Xaa Xaa Xaa Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Glu
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 101
<211> LENGTH: 101
<212> TYPE: PRT
<213> ORGANISM: Artificial Sequence
<220> FEATURE:
<223> OTHER INFORMATION: CD1-Loop
<220> FEATURE:
<221> NAME/KEY: MISC_FEATURE
<223> OTHER INFORMATION: X1-X10 can be modified by deletion,
      substitution (with any amino acid), or insertion (with any amino
      acid)
<220> FEATURE:
<221> NAME/KEY: misc_feature
<222> LOCATION: (37)..(46)
<223> OTHER INFORMATION: Xaa can be any naturally occurring amino acid

<400> SEQUENCE: 101

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Xaa Xaa Xaa Xaa Xaa Xaa Xaa Xaa Xa

```
<210> SEQ ID NO 102
<211> LENGTH: 101
<212> TYPE: PRT
<213> ORGANISM: Artificial Sequence
<220> FEATURE:
<223> OTHER INFORMATION: LI-3 (b)
<220> FEATURE:
<221> NAME/KEY: MISC_FEATURE
<223> OTHER INFORMATION: X1 and X2 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (28)..(29)
<223> OTHER INFORMATION: Xaa can be any naturally occurring amino acid
<220> FEATURE:
<221> NAME/KEY: misc_feature
<222> LOCATION: (77)..(83)
<223> OTHER INFORMATION: Xaa can be any naturally occurring amino acid

<400> SEQUENCE: 102

Val Ser Asp Val Pro Arg Asp Leu Glu Val Val Ala Ala Thr Pro Thr
1               5                   10                  15

Ser Leu Leu Ile Ser Trp Asp Ala Pro Ala Val Xaa Xaa Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Xaa Xaa Xaa Xaa
65                  70                  75                  80

Xaa Xaa Xaa Ser Ser Lys Pro Ile Ser Ile Asn Tyr Arg Thr Glu Ile
                85                  90                  95

Asp Lys Pro Ser Gln
            100

<210> SEQ ID NO 103
<211> LENGTH: 101
<212> TYPE: PRT
<213> ORGANISM: Artificial Sequence
<220> FEATURE:
<223> OTHER INFORMATION: LI-1 (a)
<220> FEATURE:
<221> NAME/KEY: MISC_FEATURE
<223> OTHER INFORMATION: X1-X9 can be modified by substitution (with any
      amino acid)
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (77)..(82)
<223> OTHER INFORMATION: Xaa can be any naturally occurring amino acid

<400> SEQUENCE: 103

Val Ser Asp Val Pro Arg Asp Leu Glu Val Val Ala Ala Thr Pro Thr
1               5                   10                  15

Ser Leu Leu Ile Ser Trp Asp Ala Pro Ala Xaa Xaa Xaa Arg Tyr Tyr
            20                  25                  30

Arg Ile Thr Tyr Gly Glu Thr Gly Gly Asn Ser Pro Val Gln Glu Phe
        35                  40                  45
```

```
Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Xaa Xaa Xaa Xaa
 65                  70                  75                  80

Xaa Xaa Ala Ser Ser Lys Pro Ile Ser Ile Asn Tyr Arg Thr Glu Ile
                85                  90                  95

Asp Lys Pro Ser Gln
            100

<210> SEQ ID NO 104
<211> LENGTH: 101
<212> TYPE: PRT
<213> ORGANISM: Artificial Sequence
<220> FEATURE:
<223> OTHER INFORMATION: LI-1 (b)
<220> FEATURE:
<221> NAME/KEY: MISC_FEATURE
<223> OTHER INFORMATION: X1-X10 can be modified by substitution (with
      any amino acid)
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (77)..(83)
<223> OTHER INFORMATION: Xaa can be any naturally occurring amino acid

<400> SEQUENCE: 104

Val Ser Asp Val Pro Arg Asp Leu Glu Val Val Ala Ala Thr Pro Thr
 1               5                  10                  15

Ser Leu Leu Ile Ser Trp Asp Ala Pro Ala Xaa Xaa Xaa Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Xaa Xaa Xaa Xaa
 65                  70                  75                  80

Xaa Xaa Xaa Ser Ser Lys Pro Ile Ser Ile Asn Tyr Arg Thr Glu Ile
                85                  90                  95

Asp Lys Pro Ser Gln
            100

<210> SEQ ID NO 105
<211> LENGTH: 101
<212> TYPE: PRT
<213> ORGANISM: Artificial Sequence
<220> FEATURE:
<223> OTHER INFORMATION: LI-1 (c)
<220> FEATURE:
<221> NAME/KEY: MISC_FEATURE
<223> OTHER INFORMATION: X1-X13 can be modified by substitution (with
      any amino acid)
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (77)..(86)
<223> OTHER INFORMATION: Xaa can be any naturally occurring amino acid

<400> SEQUENCE: 105

Val Ser Asp Val Pro Arg Asp Leu Glu Val Val Ala Ala Thr Pro Thr
```

```
                1               5                  10                  15
Ser Leu Leu Ile Ser Trp Asp Ala Pro Ala Xaa Xaa Xaa Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
                50                  55                  60

Gly Val Asp Tyr Thr Ile Thr Val Tyr Ala Val Thr Xaa Xaa Xaa Xaa
 65                 70                  75                  80

Xaa Xaa Xaa Xaa Xaa Xaa Pro Ile Ser Ile Asn Tyr Arg Thr Glu Ile
                85                  90                  95

Asp Lys Pro Ser Gln
                100

<210> SEQ ID NO 106
<211> LENGTH: 101
<212> TYPE: PRT
<213> ORGANISM: Artificial Sequence
<220> FEATURE:
<223> OTHER INFORMATION: LI-2 (a)
<220> FEATURE:
<221> NAME/KEY: MISC_FEATURE
<223> OTHER INFORMATION: X1-X9 can be modified by substitution (with any
      amino acid)
<220> FEATURE:
<221> NAME/KEY: misc_feature
<222> LOCATION: (24)..(29)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 106

Val Ser Asp Val Pro Arg Asp Leu Glu Val Val Ala Ala Thr Pro Thr
 1               5                  10                  15

Ser Leu Leu Ile Ser Trp Asp Xaa Xaa Xaa Xaa Xaa Xaa Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
                50                  55                  60

Gly Val Asp Tyr Thr Ile Thr Val Tyr Ala Val Thr Xaa Xaa Xaa Asp
 65                 70                  75                  80

Ser Pro Ala Ser Ser Lys Pro Ile Ser Ile Asn Tyr Arg Thr Glu Ile
                85                  90                  95

Asp Lys Pro Ser Gln
                100

<210> SEQ ID NO 107
<211> LENGTH: 101
<212> TYPE: PRT
<213> ORGANISM: Artificial Sequence
<220> FEATURE:
<223> OTHER INFORMATION: LI-2 (b)
<220> FEATURE:
<221> NAME/KEY: MISC_FEATURE
<223> OTHER INFORMATION: X1-X11 can be modified by substitution (with
      any amino acid)
<220> FEATURE:
<221> NAME/KEY: misc_feature
<222> LOCATION: (24)..(29)
<223> OTHER INFORMATION: Xaa can be any naturally occurring amino acid
<220> FEATURE:
```

```
<221> NAME/KEY: misc_feature
<222> LOCATION: (52)..(53)
<223> OTHER INFORMATION: Xaa can be any naturally occurring amino acid
<220> FEATURE:
<221> NAME/KEY: misc_feature
<222> LOCATION: (77)..(79)
<223> OTHER INFORMATION: Xaa can be any naturally occurring amino acid

<400> SEQUENCE: 107

Val Ser Asp Val Pro Arg Asp Leu Glu Val Val Ala Ala Thr Pro Thr
 1               5                  10                  15

Ser Leu Leu Ile Ser Trp Asp Xaa Xaa Xaa Xaa Xaa Arg Tyr Tyr
            20                  25                  30

Arg Ile Thr Tyr Gly Glu Thr Gly Gly Asn Ser Pro Val Gln Glu Phe
             35                  40                  45

Thr Val Pro Xaa Xaa Lys Ser Thr Ala Thr Ile Ser Gly Leu Lys Pro
         50                  55                  60

Gly Val Asp Tyr Thr Ile Thr Val Tyr Ala Val Thr Xaa Xaa Xaa Asp
 65                  70                  75                  80

Ser Pro Ala Ser Ser Lys Pro Ile Ser Ile Asn Tyr Arg Thr Glu Ile
                 85                  90                  95

Asp Lys Pro Ser Gln
            100

<210> SEQ ID NO 108
<211> LENGTH: 101
<212> TYPE: PRT
<213> ORGANISM: Artificial Sequence
<220> FEATURE:
<223> OTHER INFORMATION: NW3
<220> FEATURE:
<221> NAME/KEY: MISC_FEATURE
<223> OTHER INFORMATION: X13, X14, X20, and X34 residues can be modified
      by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (27)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
```

<400> SEQUENCE: 108

Xaa Xaa Xaa Xaa Xaa Xaa Xaa Leu Glu Val Val Ala Ala Thr Pro Thr
1               5                   10                  15

Ser Leu Leu Ile Ser Trp Asp Ala Pro Ala Xaa Xaa Xaa Xaa Xaa Tyr
            20                  25                  30

Xaa Ile Thr Tyr Gly Glu Thr Gly Gly Asn Ser Pro Val Gln Glu Phe
            35                  40                  45

Xaa Val Xaa Xaa Xaa Xaa Thr Ala Thr Ile Ser Gly Leu Lys Pro
        50                  55                  60

Gly Val Asp Tyr Thr Ile Thr Val Xaa Ala Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 109
<211> LENGTH: 101
<212> TYPE: PRT
<213> ORGANISM: Artificial Sequence
<220> FEATURE:
<223> OTHER INFORMATION: NP6-2
<220> FEATURE:
<221> NAME/KEY: MISC_FEATURE
<223> OTHER INFORMATION: X1, X2, X3 residues can be modified by
      substitution (with any amino acid)
<220> FEATURE:
<221> NAME/KEY: MISC_FEATURE
<223> OTHER INFORMATION: Remaining X amino acid residues can be
      modified by deletion, substitution (with any amino acid), or
      insertion (with any amino acid).
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (75)..(86)
<223> OTHER INFORMATION: Xaa can be any naturally occurring amino acid

<400> SEQUENCE: 109

Val Ser Asp Val Pro Arg Asp Leu Glu Val Val Ala Ala Thr Pro Thr
1               5                   10                  15

Ser Leu Leu Ile Ser Trp Asp Ala Pro Ala Val Xaa Val Xaa Xaa Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Xaa Xaa Xaa Xaa Xaa
65                  70                  75                  80

Xaa Xaa Xaa Xaa Xaa Xaa Pro Ile Ser Ile Asn Tyr Arg Thr Glu Ile
                85                  90                  95

Asp Lys Pro Ser Gln
            100

<210> SEQ ID NO 110
<211> LENGTH: 101

```
<212> TYPE: PRT
<213> ORGANISM: Artificial Sequence
<220> FEATURE:
<223> OTHER INFORMATION: NP1
<220> FEATURE:
<221> NAME/KEY: MISC_FEATURE
<223> OTHER INFORMATION: X17 residues can be modified by substitution
      (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid

<400> SEQUENCE: 110

Xaa Xaa Xaa Xaa Xaa Xaa Xaa Leu Glu Val Val Ala Ala Thr Pro Thr
1               5                   10                  15

Ser Leu Leu Ile Ser Trp Xaa Xaa Xaa Xaa Xaa Xaa Xaa Xaa Xaa Tyr
            20                  25                  30

Xaa Ile Thr Tyr Gly Glu Thr Gly Gly Asn Ser Pro Val Gln Glu Phe
        35                  40                  45

Thr Val Xaa Xaa Xaa Xaa Xaa Xaa Ala Thr Ile Ser Gly Leu Lys Pro
    50                  55                  60

Gly Val Asp Tyr Thr Ile Thr Val Tyr Ala Xaa Xaa Xaa Xaa Xaa Xaa
65                  70                  75                  80

Xaa Xaa Xaa Xaa Xaa Xaa Xaa Ile Ser Ile Asn Tyr Arg Thr Glu Ile
                85                  90                  95

Asp Lys Pro Ser Gln
            100

<210> SEQ ID NO 111
<211> LENGTH: 101
<212> TYPE: PRT
<213> ORGANISM: Artificial Sequence
<220> FEATURE:
<223> OTHER INFORMATION: NE1
<220> FEATURE:
<221> NAME/KEY: MISC_FEATURE
<223> OTHER INFORMATION: X8, X9, X25 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
```

-continued

```
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid

<400> SEQUENCE: 111

Xaa Xaa Xaa Xaa Xaa Xaa Xaa Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Arg Ile Thr Tyr Gly Glu Thr Gly Gly Asn Ser Pro Val Gln Glu Phe
            35                  40                  45

Thr Val Xaa Xaa Xaa Xaa Xaa Ala Xaa Ile Ser Gly Leu Lys Pro
        50                  55                  60

Gly Val Asp Tyr Thr Ile Thr Val Tyr Ala Xaa Xaa Xaa Xaa Xaa
65                  70                  75                  80

Xaa Xaa Xaa Xaa Xaa Xaa Xaa Ile Ser Ile Asn Tyr Arg Thr Glu Ile
                85                  90                  95

Asp Lys Pro Ser Gln
            100

<210> SEQ ID NO 112
<211> LENGTH: 101
<212> TYPE: PRT
<213> ORGANISM: Artificial Sequence
<220> FEATURE:
<223> OTHER INFORMATION: NP4-5
<220> FEATURE:
<221> NAME/KEY: MISC_FEATURE
<223> OTHER INFORMATION: X8, X9, X19-X31, and X45 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
```

```
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 112

Xaa Xaa Xaa Xaa Xaa Xaa Xaa Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Xaa Ala Xaa Ile Xaa Gly Leu Lys Pro
    50                  55                  60

Gly Val Asp Tyr Thr Ile Xaa Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 113
<211> LENGTH: 101
<212> TYPE: PRT
<213> ORGANISM: Artificial Sequence
<220> FEATURE:
<223> OTHER INFORMATION: NP6-1
<220> FEATURE:
<221> NAME/KEY: MISC_FEATURE
<223> OTHER INFORMATION: X8, X9, X19-X21, X28-X31, and X45 residues can
      be modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
```

```
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 113

Xaa Xaa Xaa Xaa Xaa Xaa Xaa Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Xaa Ala Xaa Ile Xaa Gly Leu Lys Pro
    50                  55                  60

Gly Val Asp Tyr Thr Ile Xaa Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
                100
```

```
<210> SEQ ID NO 114
<211> LENGTH: 101
<212> TYPE: PRT
<213> ORGANISM: Artificial Sequence
<220> FEATURE:
<223> OTHER INFORMATION: NW2
<220> FEATURE:
<221> NAME/KEY: MISC_FEATURE
<223> OTHER INFORMATION: X17-X19, X25, X26, and X40 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(55)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 114

Xaa Xaa Xaa Xaa Xaa Xaa Xaa Leu Glu Val Val Ala Ala Thr Pro Thr
1               5                   10                  15

Ser Leu Leu Ile Ser Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Thr Ala Thr Ile Ser Gly Leu Lys Pro
    50                  55                  60

Gly Val Asp Tyr Thr Ile Xaa Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
```

<210> SEQ ID NO 115
<211> LENGTH: 101
<212> TYPE: PRT
<213> ORGANISM: Artificial Sequence
<220> FEATURE:
<223> OTHER INFORMATION: NP1'
<220> FEATURE:
<221> NAME/KEY: MISC_FEATURE
<223> OTHER INFORMATION: X1-X7, and X17 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid)
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid

<400> SEQUENCE: 115

Xaa Xaa Xaa Xaa Xaa Xaa Xaa Leu Glu Val Val Ala Ala Thr Pro Thr
 1               5                  10                  15

Ser Leu Leu Ile Ser Trp Xaa Xaa Xaa Xaa Xaa Xaa Xaa Xaa Xaa Tyr
             20                  25                  30

Xaa Ile Thr Tyr Gly Glu Thr Gly Gly Asn Ser Pro Val Gln Glu Phe
         35                  40                  45

Thr Val Xaa Xaa Xaa Xaa Xaa Xaa Ala Thr Ile Ser Gly Leu Lys Pro
     50                  55                  60

Gly Val Asp Tyr Thr Ile Thr Val Tyr Ala Xaa Xaa Xaa Xaa Xaa Xaa
 65                  70                  75                  80

Xaa Xaa Xaa Xaa Xaa Xaa Xaa Ile Ser

<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid

<400> SEQUENCE: 116

Xaa Xaa Xaa Xaa Xaa Xaa Xaa Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Arg Ile Thr Tyr Gly Glu Thr Gly Gly Asn Ser Pro Val Gln Glu Phe
        35                  40                  45

Thr Val Xaa Xaa Xaa Xaa Xaa Xaa Ala Xaa Ile Ser Gly Leu Lys Pro
    50                  55                  60

Gly Val Asp Tyr Thr Ile Thr Val Tyr Ala Xaa Xaa Xaa Xaa Xaa Xaa
65                  70                  75                  80

Xaa Xaa Xaa Xaa Xaa Xaa Xaa Ile Ser Ile Asn Tyr Arg Thr Glu Ile
                85                  90                  95

Asp Lys Pro Ser Gln
            100

<210> SEQ ID NO 117
<211> LENGTH: 101
<212> TYPE: PRT
<213> ORGANISM: Artificial Sequence
<220> FEATURE:
<223> OTHER INFORMATION: NP4
<220> FEATURE:
<221> NAME/KEY: MISC_FEATURE
<223> OTHER INFORMATION: X1, X2, X9-X23, and X37 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid

```
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 117

Val Ser Asp Val Pro Arg Asp Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Xaa Ala Xaa Ile Ser Gly Leu Lys Pro
    50                  55                  60

Gly Val Asp Tyr Thr Ile Xaa Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 118
<211> LENGTH: 101
<212> TYPE: PRT
<213> ORGANISM: Artificial Sequence
<220> FEATURE:
<223> OTHER INFORMATION: NP4-FG
<220> FEATURE:
<221> NAME/KEY: MISC_FEATURE
<223> OTHER INFORMATION: X1, X2, X16 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (71)..(71)

```
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 118

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
         35                  40                  45

Thr Val Pro Gly Ser Lys Ser Thr Ala Thr Ile Ser Gly Leu Lys Pro
     50                  55                  60

Gly Val Asp Tyr Thr Ile Xaa Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                 85                  90                  95

Asp Lys Pro Ser Gln
            100

<210> SEQ ID NO 119
<211> LENGTH: 101
<212> TYPE: PRT
<213> ORGANISM: Artificial Sequence
<220> FEATURE:
<223> OTHER INFORMATION: NP5
<220> FEATURE:
<221> NAME/KEY: MISC_FEATURE
<223> OTHER INFORMATION: X1-X9, X19-X30, and X44 residues can be
      modified by substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
```

```
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 119

Xaa Xaa Xaa Xaa Xaa Xaa Xaa Leu Glu Val Val Ala Ala Thr Pro Thr
1               5                   10                  15

Ser Leu Xaa Ile Xaa Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Xaa Ala Xaa Ile Xaa Gly Leu Lys Pro
    50                  55                  60

Gly Val Asp Tyr Thr Ile Thr Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 120
<211> LENGTH: 101
<212> TYPE: PRT
<213> ORGANISM: Artificial Sequence
<220> FEATURE:
<223> OTHER INFORMATION: NP6-3
<220> FEATURE:
<221> NAME/KEY: MISC_FEATURE
<223> OTHER INFORMATION: X1-X22, and X36 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
```

<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 120

Val Ser Asp Val Pro Arg Asp Leu Glu Val Val Ala Ala Thr Pro Thr
1               5                   10                  15

Ser Leu Leu Ile Xaa Trp Xaa Xaa Xaa Xaa Xaa Xaa Xaa Xaa Xaa Tyr
            20                  25                  30

Xaa Ile Xaa Tyr Gly Glu Thr Gly Gly Asn Ser Pro Val Gln Glu Phe
        35                  40                  45

Xaa Val Xaa Xaa Xaa Xaa Xaa Xaa Ala Xaa Ile Xaa Gly Leu Lys Pro
    50                  55                  60

Gly Val Asp Tyr Thr Ile Thr Val Xaa Ala Xaa Xaa Xaa Xaa Xaa Xaa
65                  70                  75                  80

Xaa Xaa Xaa Xaa Xaa Xaa Xaa Ile Xaa Ile Asn Tyr Arg Thr Glu Ile
                85                  90                  95

Asp Lys Pro Ser Gln
            100

<210> SEQ ID NO 121
<211> LENGTH: 94
<212> TYPE: PRT
<213> ORGANISM: Artificial Sequence
<220> FEATURE:
<223> OTHER INFORMATION: WS4
<220> FEATURE:
<221> NAME/KEY: MISC_FEATURE
<223> OTHER INFORMATION: X1-X4 and X15-X19 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid -continued

```
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid

<400> SEQUENCE: 121

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Xaa Phe
        35                  40                  45

Xaa Val Pro Gly Ser Lys Ser Thr Ala Thr Ile Ser Gly Leu Lys Pro
    50                  55                  60

Gly Val Xaa Tyr Xaa Ile Xaa Val Xaa Ala Val Xaa Xaa Xaa Xaa Xaa
65                  70                  75                  80

Xaa Xaa Xaa Xaa Xaa Xaa Pro Ile Ser Ile Asn Tyr Arg Thr
                85                  90

<210> SEQ ID NO 122
<211> LENGTH: 94
<212> TYPE: PRT
<213> ORGANISM: Artificial Sequence
<220> FEATURE:
<223> OTHER INFORMATION: WS5
<220> FEATURE:
<221> NAME/KEY: MISC_FEATURE
<223> OTHER INFORMATION: X1-X4 and X14-X17 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
```

-continued

```
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid

<400> SEQUENCE: 122

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Glu Phe
        35                  40                  45

Thr Val Pro Gly Ser Lys Ser Thr Ala Thr Ile Ser Gly Leu Lys Pro
    50                  55                  60

Gly Val Xaa Tyr Xaa Ile Xaa Val Xaa Ala Val Xaa Xaa Xaa Xaa Xaa
65                  70                  75                  80

Xaa Xaa Xaa Xaa Xaa Xaa Pro Ile Ser Ile Asn Tyr Arg Thr
                85                  90

<210> SEQ ID NO 123
<211> LENGTH: 94
<212> TYPE: PRT
<213> ORGANISM: Artificial Sequence
<220> FEATURE:
<223> OTHER INFORMATION: WS6
<220> FEATURE:
<221> NAME/KEY: MISC_FEATURE
<223> OTHER INFORMATION: X1-X3 and X13-X16 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
```

```
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (76)..(86)
<223> OTHER INFORMATION: Xaa can be any naturally occurring amino acid

<400> SEQUENCE: 123

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Xaa Tyr
            20                  25                  30

Xaa Ile Xaa Tyr Xaa Xaa Xaa Xaa Xaa Xaa Xaa Xaa Gln Glu Phe
        35                  40                  45

Thr Val Pro Gly Ser Lys Ser Thr Ala Thr Ile Ser Gly Leu Lys Pro
50                  55                  60

Gly Val Xaa Tyr Xaa Ile Xaa Val Xaa Ala Val Xaa Xaa Xaa Xaa Xaa
65                  70                  75                  80

Xaa Xaa Xaa Xaa Xaa Xaa Pro Ile Ser Ile Asn Tyr Arg Thr
                85                  90

<210> SEQ ID NO 124
<211> LENGTH: 94
<212> TYPE: PRT
<213> ORGANISM: Artificial Sequence
<220> FEATURE:
<223> OTHER INFORMATION: WS7
<220> FEATURE:
<221> NAME/KEY: MISC_FEATURE
<223> OTHER INFORMATION: X1-X4 and X15-X20 residues can be modified by
      substitution (with any amino acid)
<220> FEATURE:
<221> NAME/KEY: MISC_FEATURE
<223> OTHER INFORMATION: Remaining X amino acid residues can be modified
      by deletion, substitution (with any amino acid), or insertion
      (with any amino acid).
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(45)
<223> OTHER INFORMATION: Xaa can be any naturally occurring amino acid
<220> FEATURE:
<221> NAME/KEY: misc_feature
```

```
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (75)..(87)
<223> OTHER INFORMATION: Xaa can be any naturally occurring amino acid

<400> SEQUENCE: 124

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Xaa Tyr Xaa Xaa Xaa Xaa Xaa Xaa Xaa Xaa Gln Xaa Phe
        35                  40                  45

Xaa Xaa Pro Gly Ser Lys Ser Thr Ala Thr Ile Ser Gly Leu Lys Pro
    50                  55                  60

Gly Val Xaa Tyr Xaa Ile Xaa Val Xaa Ala Xaa Xaa Xaa Xaa Xaa Xaa
65                  70                  75                  80

Xaa Xaa Xaa Xaa Xaa Xaa Xaa Ile Ser Ile Asn Tyr Arg Thr
                85                  90
```

What is claimed:

1. A polypeptide comprising a human fibronectin type 3 tenth ($^{10}$Fn3) domain, which comprises AB, BC, CD, DE, EF, and FG loops and β-strands A, B, C, D, E, F, and G, wherein: (i) the BC loop has the amino acid sequence of the corresponding loop of a wild-type human $^{10}$Fn3 domain (SEQ ID NO: 1 or 6), (ii) the amino acid sequences of the CD and FG loops are modified relative to the corresponding loops of the wild-type human $^{10}$Fn3 domain (SEQ ID NO: 1 or 6), and (iii) the amino acid sequence of at least one of the β-strands is modified relative to the corresponding β-strand of the wild-type human $^{10}$Fn3 domain (SEQ ID NO: 1 or 6).

2. The polypeptide of claim 1, wherein the at least one modified β-strand is adjacent to the modified CD loop or the modified FG loop in a linear sequence of the $^{10}$Fn3 domain.

3. The polypeptide of claim 1, wherein the amino acid sequences of at least two of the β-strands have been modified relative to the corresponding β-strands of the wild-type human $^{10}$Fn3 domain (SEQ ID NO: 1 or 6).

4. The polypeptide of claim 3, wherein each of the at least two modified β-strands is adjacent to each side of the modified CD loop or the modified FG loop in the linear sequence of the $^{10}$Fn3 domain.

5. The polypeptide of claim 3, wherein the modified CD loop, the modified FG loop, and each of the at least two modified β-strands contribute to binding to a target.

6. The polypeptide of claim 3, wherein the amino acid sequences of the β-strand C, the β-strand D, the β-strand F, and the β-strand G are modified relative to the corresponding β-strands of the wild-type human $^{10}$Fn3 domain (SEQ ID NO: 1 or 6).

7. The polypeptide of claim 1, wherein the AB loop, the DE loop, the EF loop, or a combination thereof has the amino acid sequence of the corresponding loop of the wild-type human $^{10}$Fn3 domain (SEQ ID NO: 1 or 6).

8. The polypeptide of claim 1, which has reduced immunogenicity relative to a corresponding polypeptide comprising the wild-type human $^{10}$Fn3 domain (SEQ ID NO: 1 or 6).

9. The polypeptide of claim 1, wherein the amino acid sequence of the modified CD loop, the modified FG loop, or both have been extended in length relative to the amino acid sequence of the corresponding loop of the wild-type human $^{10}$Fn3 domain (SEQ ID NO: 1 or 6).

10. The polypeptide of claim 1, wherein the amino acid sequence of the modified CD loop, the modified FG loop, or both have been reduced in length relative to the amino acid sequence of the corresponding loop of the wild-type human $^{10}$Fn3 domain (SEQ ID NO: 1 or 6).

11. The polypeptide of claim 1, which has at least 50% sequence identity to the amino acid sequence of the wild-type human $^{10}$Fn3 domain (SEQ ID NO: 1 or 6).

12. The polypeptide of claim 1, wherein the polypeptide which has at least 65% sequence identity to the amino acid sequence of the wild-type human $^{10}$Fn3 domain (SEQ ID NO: 1 or 6).

13. A library comprising a plurality of polypeptides comprising a human fibronectin type 3 tenth ($^{10}$Fn3) domain, which comprises AB, BC, CD, DE, EF, and FG loops and β strands A, B, C, D, E, F, and G, wherein: (i) the BC loop has the amino acid sequence of the corresponding loop of a wild-type human $^{10}$Fn3 domain (SEQ ID NO: 1 or 6), (ii) the amino acid sequences of the CD and FG loops are modified relative to the corresponding loops of the wild-type human $^{10}$Fn3 domain (SEQ ID NO: 1 or 6), and (iii) the amino acid sequence of at least one of the β-strands is modified relative to the corresponding β-strand of the wild-type human $^{10}$Fn3 domain (SEQ ID NO: 1 or 6).

14. The library of claim 13, which comprises at least $10^5$ polypeptides each comprising a different $^{10}$Fn3 domain sequence.

15. The polypeptide of claim 1, wherein at least four of the amino acid residues of the CD loop are modified relative to the corresponding amino acid residues of the CD loop of the wild-type human $^{10}$Fn3 domain (SEQ ID NO: 1 or 6).

16. The polypeptide of claim 1, wherein at least one amino acid residue of the CD loop is the same as the wild type amino acids at those corresponding amino acid residue of the CD loop of the wild-type human $^{10}$Fn3 domain (SEQ ID NO: 1 or 6).

17. The polypeptide of claim 16, wherein the at least one amino acid residue of the CD loop that is the same as the wild-type amino acid residue corresponds to amino acid residue 46 of the wild-type human $^{10}$Fn3 domain (SEQ ID NO: 1 or 6).

18. The polypeptide of claim 16, wherein the at least one amino acid residue of the CD loop that is the same as the wild-type amino acid residue corresponds to amino acid residue 47 of the wild-type human $^{10}$Fn3 domain (SEQ ID NO: 1 or 6).

19. The polypeptide of claim 6, wherein each of modified β-strands C, D, F, and G comprises a hydrophobic core amino acid residue, and wherein one or more of the hydrophobic core amino acid residues are not modified relative to the corresponding amino acid residues of the wild-type human $^{10}$Fn3 domain (SEQ ID NO: 1 or 6).

20. The polypeptide of claim 6, wherein: (i) two of the amino acid residues of the β-strand C are modified relative to the corresponding amino acid residues of β-strand C of the wild-type human $^{10}$Fn3 domain (SEQ ID NO: 1 or 6), (ii) one of the amino acid residues of the β-strand D is modified relative to the corresponding amino acid residue of β-strand D of the wild-type human $^{10}$Fn3 domain (SEQ ID NO: 1 or 6), (iii) three of the amino acid residues of the β-strand F are modified relative to the corresponding amino acid residues of the β-strand F of the wild-type human $^{10}$Fn3 domain (SEQ ID NO: 1 or 6), (iv) two of the amino acid residues of the β-strand G are modified relative to the corresponding amino acid residues of the β-strand G of the wild-type human $^{10}$Fn3 domain (SEQ ID NO: 1 or 6), or (v) any combination thereof.

* * * * *

UNITED STATES PATENT AND TRADEMARK OFFICE
CERTIFICATE OF CORRECTION

PATENT NO. : 11,279,751 B2
APPLICATION NO. : 16/581877
DATED : March 22, 2022
INVENTOR(S) : Jonathan Davis, Dasa Lipovsek and Ray Camphausen Page 1 of 1

It is certified that error appears in the above-identified patent and that said Letters Patent is hereby corrected as shown below:

In the Claims

In Claim 7, at Column 190, Line 50, please delete "1 or 6)." and insert --1 or 6).--;

In Claim 12, at Column 191, Line 1, please delete "wherein the polypeptide";

In Claim 13, at Column 191, Lines 7-8, please delete "β strands" and insert --β-strands--; and In Claim 16, at Column 191, Lines 25-26, please delete "wild type amino acids at those".

Signed and Sealed this
Twenty-sixth Day of December, 2023

Katherine Kelly Vidal
Director of the United States Patent and Trademark Office